US010618864B2

(12) United States Patent
Mullen et al.

(10) Patent No.: US 10,618,864 B2
(45) Date of Patent: Apr. 14, 2020

(54) PROCESS TO PREPARE LEVULINIC ACID

(71) Applicant: GFBiochemicals IP Assets B.V., Geleen (NL)

(72) Inventors: Brian D. Mullen, Delano, MN (US); Cora M. Leibig, Maple Grove, MN (US); Louis A. Kapicak, Cross Lanes, WV (US); Donald L. Bunning, South Charleston, WV (US); Steven R. Strand, San Diego, CA (US); Daniel Joseph Brunelle, Burnt Hill, NY (US); Marc David Rodwogin, Minneapolis, MN (US); Robert Page Shirtum, Sonora, TX (US); Andrew J. Louwagie, Golden Valley, MN (US); Dorie Janine Yontz, Bloomington, MN (US); Matthew John Tjosaas, Minneapolis, MN (US)

(73) Assignee: GFBiochemicals IP Assets B.V., Geleen (NL)

( * ) Notice: Subject to any disclaimer, the term of this patent is extended or adjusted under 35 U.S.C. 154(b) by 0 days.

(21) Appl. No.: 16/051,013

(22) Filed: Jul. 31, 2018

(65) Prior Publication Data
US 2019/0016658 A1 Jan. 17, 2019

Related U.S. Application Data

(63) Continuation of application No. 14/359,124, filed as application No. PCT/US2012/066368 on Nov. 21, 2012, now abandoned.

(60) Provisional application No. 61/722,766, filed on Nov. 5, 2012, provisional application No. 61/581,006, filed on Dec. 28, 2011, provisional application No. 61/576,818, filed on Dec. 16, 2011, provisional application No. 61/563,276, filed on Nov. 23, 2011.

(51) Int. Cl.
*C07C 51/00* (2006.01)
*C07C 59/185* (2006.01)

(52) U.S. Cl.
CPC .................................. *C07C 51/00* (2013.01)

(58) Field of Classification Search
CPC .............................. C07C 51/00; C07C 59/185
USPC ........................................................ 562/577
See application file for complete search history.

(56) References Cited

U.S. PATENT DOCUMENTS

| | | |
|---|---|---|
| 1,861,200 A | 5/1932 | Webber et al. |
| 2,008,720 A | 7/1935 | Lawson et al. |
| 2,029,412 A | 2/1936 | Cox et al. |
| 2,040,849 A | 5/1936 | Holt |
| 2,257,389 A | 9/1941 | Macallum |
| 2,270,328 A | 1/1942 | Moyer |
| 2,293,724 A | 8/1942 | Faerber |
| 2,305,738 A | 12/1942 | Scheuing et al. |
| 2,382,572 A | 8/1945 | Meyer |
| 2,684,981 A | 7/1954 | Sherman |
| 2,738,367 A | 3/1956 | Redmon |
| 2,780,588 A | 2/1957 | Dunlop |
| 2,813,900 A | 11/1957 | Dunlop et al. |
| 2,840,605 A | 6/1958 | Leonard |
| 2,917,537 A | 12/1959 | Haury |
| 3,065,263 A | 11/1962 | Carlson |
| 3,258,481 A | 6/1966 | Sassenrath et al. |
| 3,267,136 A | 8/1966 | Vincenty et al. |
| 3,275,505 A | 9/1966 | Herschler et al. |
| 3,580,906 A | 5/1971 | Bernasek |
| 3,663,612 A | 5/1972 | Ramos-Rodriguez |
| 3,701,789 A | 10/1972 | Ramos-Rodriguez |
| 4,236,021 A | 11/1980 | Hsu et al. |
| 4,342,831 A | 8/1982 | Faber et al. |
| 4,590,283 A | 5/1986 | Gaset et al. |
| 4,615,742 A | 10/1986 | Wright |
| 5,175,358 A | 12/1992 | Capai et al. |
| 5,188,673 A | 2/1993 | Clausen et al. |
| 5,608,105 A | 3/1997 | Fitzpatrick |
| 5,859,263 A | 1/1999 | Gharpade et al. |
| 5,892,107 A | 4/1999 | Farone et al. |
| 6,054,611 A * | 4/2000 | Farone ................... C07C 51/00 549/429 |
| 7,317,116 B2 * | 1/2008 | Sanborn ................. C07C 51/00 549/483 |
| 7,393,963 B2 | 7/2008 | Sanborn et al. |
| 7,432,382 B2 | 10/2008 | Sanborn et al. |
| 7,520,905 B1 | 4/2009 | Lightner |
| 7,579,489 B2 | 8/2009 | Sanborn |
| 7,579,490 B2 | 8/2009 | Sanborn et al. |
| 7,829,732 B2 | 11/2010 | Mascal |
| 7,939,681 B2 | 5/2011 | Zhao et al. |
| 7,959,765 B2 | 6/2011 | Argyropoulos |
| 8,058,458 B2 | 11/2011 | Sanborn |
| 8,115,020 B2 | 2/2012 | Sanborn |
| 8,389,761 B2 | 3/2013 | Dumesic et al. |
| 2006/0047139 A1 * | 3/2006 | Ayoub ..................... C07C 67/08 560/155 |
| 2008/0241902 A1 | 10/2008 | Berry et al. |
| 2008/0311637 A1 | 12/2008 | Navapanich et al. |
| 2009/0156841 A1 | 6/2009 | Sanborn et al. |
| 2009/0234142 A1 | 9/2009 | Mascal |

(Continued)

FOREIGN PATENT DOCUMENTS

| | | |
|---|---|---|
| AU | 2011/205116 | 8/2011 |
| AU | 2011/205117 | 8/2011 |

(Continued)

OTHER PUBLICATIONS

Roman-Leshkov et al. Angew. Chem. Int. Ed. 2010, 49, 8954-8957. (Year: 2010).*

(Continued)

*Primary Examiner* — Yong L Chu
(74) *Attorney, Agent, or Firm* — Norton Rose Fulbright US LLP

(57) ABSTRACT

The invention describes processes to prepare levulinic acid, formic acid and/or hydroxymethyl furfural from various biomass materials.

17 Claims, 17 Drawing Sheets

(56) References Cited

U.S. PATENT DOCUMENTS

| | | |
|---|---|---|
| 2010/0024806 A1 | 2/2010 | Burke et al. |
| 2010/0024807 A1 | 2/2010 | Burke et al. |
| 2010/0024808 A1 | 2/2010 | Burke et al. |
| 2010/0024809 A1 | 2/2010 | Burke et al. |
| 2010/0028089 A1 | 2/2010 | Burke et al. |
| 2010/0044210 A1 | 2/2010 | Robinson |
| 2010/0186735 A1 | 7/2010 | Burke et al. |
| 2010/0186736 A1 | 7/2010 | Burke et al. |
| 2010/0284900 A1 | 11/2010 | Chen |
| 2010/0312006 A1 | 12/2010 | Lake et al. |
| 2010/0324310 A1 | 12/2010 | Dumesic et al. |
| 2011/0011391 A1 | 1/2011 | Burke et al. |
| 2011/0071306 A1 | 3/2011 | Robinson |
| 2011/0105770 A1 | 5/2011 | Liu et al. |
| 2011/0144396 A1 | 6/2011 | Lotero et al. |
| 2011/0207922 A1 | 8/2011 | Kubo et al. |

FOREIGN PATENT DOCUMENTS

| | | |
|---|---|---|
| AU | 2011/205118 | 8/2011 |
| CN | 1680257 | 10/2005 |
| CN | 101148458 | 3/2008 |
| CN | 101381351 | 3/2009 |
| CN | 101648863 | 2/2010 |
| CN | 101691326 | 4/2010 |
| CN | 101781210 | 7/2010 |
| CN | 102093206 | 6/2011 |
| DE | 3621517 | 1/1988 |
| EP | 1860201 | 11/2007 |
| EP | 1878695 | 1/2008 |
| EP | 2033973 | 3/2009 |
| EP | 2033974 | 3/2009 |
| EP | 2336195 | 6/2011 |
| EP | 2336196 | 6/2011 |
| EP | 2336222 | 6/2011 |
| GB | 529262 | 11/1940 |
| GB | 583533 | 12/1946 |
| GB | 591858 | 9/1947 |
| GB | 600871 | 4/1948 |
| GB | 842743 | 7/1960 |
| GB | 1282926 | 7/1972 |
| GB | 13252 | 1/2009 |
| JP | 55087741 | 7/1980 |
| JP | 2006206579 | 8/2006 |
| JP | 2010143861 | 7/2010 |
| JP | 2010202548 | 9/2010 |
| RU | 2119427 | 9/1998 |
| RU | 2158192 | 10/2000 |
| RU | 2176998 | 12/2001 |
| RU | 2203266 | 4/2003 |
| RU | 2319690 | 3/2008 |
| WO | WO 84/03304 | 8/1984 |
| WO | WO 87/00205 | 1/1987 |
| WO | WO 98/19986 | 5/1988 |
| WO | WO 89/10362 | 11/1989 |
| WO | WO 96/40609 | 12/1996 |
| WO | WO 97/47579 | 12/1997 |
| WO | WO 99/67409 | 12/1999 |
| WO | WO 02/04084 | 1/2002 |
| WO | WO 03/085071 | 10/2003 |
| WO | WO 2005/058856 | 6/2005 |
| WO | WO 2005/070867 | 8/2005 |
| WO | WO 2006/063220 | 6/2006 |
| WO | WO 2007/023173 | 3/2007 |
| WO | WO 2008/137639 | 11/2008 |
| WO | WO 2009/012445 | 1/2009 |
| WO | WO 2009/046537 | 4/2009 |
| WO | WO 2009/046538 | 4/2009 |
| WO | WO 2009046524 | 4/2009 |
| WO | WO 2009/130386 | 10/2009 |
| WO | WO 2009/156842 | 12/2009 |
| WO | WO 2010/009548 | 1/2010 |
| WO | WO 2010/009549 | 1/2010 |
| WO | WO 2010/009551 | 1/2010 |
| WO | WO 2010/030617 | 3/2010 |
| WO | WO 2010/083600 | 7/2010 |
| WO | WO 2010/083601 | 7/2010 |
| WO | WO 2010/104722 | 9/2010 |
| WO | WO 2010/0124381 | 11/2010 |
| WO | WO 2010/138957 | 12/2010 |
| WO | WO 2010/141950 | 12/2010 |
| WO | WO 2011/000030 | 1/2011 |
| WO | WO 2011/002660 | 1/2011 |
| WO | WO 2011/019403 | 2/2011 |
| WO | WO 2011/020082 | 2/2011 |
| WO | WO 2011/022811 | 3/2011 |
| WO | WO 2011/022812 | 3/2011 |
| WO | WO 2011/022840 | 3/2011 |
| WO | WO 2011/124639 | 10/2011 |
| WO | WO 2011/154967 | 12/2011 |
| WO | WO 2011/161141 | 12/2011 |
| WO | WO 2011/163348 | 12/2011 |
| WO | WO 2012/015616 | 2/2012 |
| WO | WO 2012/031356 | 3/2012 |
| WO | WO 2013/106137 | 7/2013 |

OTHER PUBLICATIONS

Aida, et al. "Dehydration of d-glucose in high temperature water at pressures up to 80MPa", J. of Supercritical Fluids, No. 40, 2007, pp. 381-388.

Assary, et al., "Computational Studies of the Thermochemistry for Conversion of Glucose to Levulinic Acid", J. Phys. Chem. B. No. 114, 2010, pp. 9002-9009.

Bart, et al., "Kinetics of Esterification of Levulinic Acid With N-Butanol by Homogeneous Catalysis", Ind. Eng. Chem. Res. No. 33, 1994, pp. 21-25.

Baugh, et al., "Thermochemical Pretreatment of Lignocellulose to Enhance Methane Fermentation: I. Monosaccharide and Furfurals Hydrothermal Decomposition and Product Formation Rates", Biotechnology and Bioengineering, vol. 31, 1988, pp. 50-61.

Beale, et al., "Biosynthesis of o-aminolevulinic acid from the intact carbon skeleton of glutamic acid in greening barley", Proc. Nat. Acad. Sci. USA, vol. 72, No. 7, 1975, pp. 2719-2723.

Bozell, et al., "Production of levulinic acid and use as a platform chemical for derived products", Resources, Conservation, and Recycling, No. 28, 2000, pp. 227-239.

Cha, et al., "Levulinic acid production based on extrusion and pressurized batch reaction", Industrial Crops and Products, No. 16, 2002, pp. 109-118.

Chang, et al., "Levulinic acid production from wheat straw", Biosource Technology, No. 98, 2007, pp. 1448-1453.

Chun, et al., "Kinetic Studies on Wheat Straw Hydrolysis to Levulinic Acid", Chinese J. Chem, Eng., No. 17(5), 2009, pp. 835-839.

Chun, et al., "Kinetics of Levulinic Acid Formation from Glucose Decomposition at High Temperature", Chinese J. Chem, Eng., No. 14(5), 2006, pp. 708-712.

Cox, et al., "Industrial Uses for Cane Sugar", Industrial and Engineering Chemistry, vol. 25, No. 9, 1933, pp. 967-968.

Dautzenberg, et al., "Bio Based Fuels and fuel additives from lignocellulose feedstock via the production of levulinic acid and furfural", Holzforschung, vol. 65, 2011, pp. 439-451.

Doll, et al., "Synthesis of Branched Methyl Hydroxy Stearates Including an Ester from Bio-Based Levulinic Acid", Ind. Eng. Chem. Res. No. 46, 2007, pp. 3513-3519.

Elliot, "Conversion of Biomass Wastes to Levulinic Acid and Derivatives", Success Story, Jan. 8, 1999, 1 page.

Fang, et al., "Experimental studies for levulinic acid production from whole kernel grain sorghum", Biosource Technology, No. 81, 2002, pp. 187-192.

Ganjyal, et al., "Freezing points and small scale deicing tests for salts of levulinic acid made from grain sorghum", Biosource Technology, No. 98, 2007, pp. 2814-2818.

Girisuta, et al., "A kinetic study on the decomposition of 5-hydroxymethylfurfural into levulinic acid", Green Chum, No. 8, 2006, pp. 701-709.

(56) References Cited

OTHER PUBLICATIONS

Girisuta, et al., "Experimental and kinetic modeling studies on the acid-catalysed hydrolysis of the water hyacinth plant to levulinic acid", Biosource Technology, No. 99, 2008, pp. 8367-8375.
Girisuta, et al., "Kinetic Study on the Acid-Catalyzed Hydrolysis of Cellulose to Levulinic Acid", Ind. Eng. Chem. Res. No. 46, 2007, 1696-1708.
Girisuta, Levulinic "Acid from Lignocellulosic Biomass", Nov. 5, 2007, 160 pages.
Grote, et al. "On Levulinic Acid", reports from Annalen der Chemie, 1876, 6 pages.
Hegner, et al., "Conversion of cellulose to glucose and levulinic acid via solid-supported acid catalysis", Tetrahedron Letters, No. 51, 2010, pp. 2356-2358.
Horvat, et al., "Mechanism of levulinic acid formation" Tetrahedron Letters, No. 17, vol. 26, 1985, pp. 2111-2114.
International Preliminary Report on Patentability from related PCT Application No. PCT/US2012/066368, dated May 27, 2014.
International Search Report from related PCT Application No. PCT/US2012/066368, dated Mar. 22, 2013, 4 pages.
Jeong, et al. "Production of Sugars and Levulinic Acid from Marine Biomass Gelidium amansii", Appl. Biochem Biotechnol, No. 161, 2010, pp. 41-52.
Jow, et al., "Dehydration of d-fructose to levulinic acid over LZY zeolite catalyst", Biomass No. 14, 1987, pp. 185-194.
Kobayashi, et al., "Analysis on residue formation during wood liquefaction with polyhydric alcohol", J. Wood Sci., No. 50, 2004, pp. 407-414.
Kuster, 5-Hyrdoxymethylfurfural (HMF), A Review Focusing on its Manufacture, Starch, No. 42(8), 1990, pp. 314-321.
Langlois, et al., Pseudo Esters of Levulinic Acid, vol. 70, 1948, pp. 2624-2626.
Leonard, "Levulinic Acid As a Basic Chemical Raw Material", Industrial and Engineering Chemistry, vol. 48, No. 8, 1956, pp. 1330-1341.
Office of Industrial Technologies, Commercialization of the Biofine Technology for Levulinic Acid Production From Paper Sludge, 1998, 2 pages.
Office of Industrial Technologies, Manufacture of Industrial Chemicals from Levulinic Acid: A New Feedstock for the Chemicals Industry, 1999, 2 pages.
Olson, "Final Report—Subtask 4.1—Conversion of Lignocellulosic Material to Chemicals and Fuels", Jun. 2001, 16 pages.
Park, et al., "Enzymatic Synthesis of Rubber From Mevalonic Acid", Mar. 18, 1958, 4 pages.
Peng, et al., "Catalytic Conversion of Cellulose to Levulinic Acid by Metal Chlorides", Molecules No. 15, 2010, pp. 5258-5272.
Qi, et al., "Sulfated Zirconia As a Solid Acid Catalyst for the Dehydration of Fructose to 5-Hydroxymethylfurfural", Catalysis Communications, No. 10, 2009, pp. 1771-1775.
Rackermann, et al., "The conversion of lignocellulosics to levulinic acid", Biofuels, Bioproducts and Biorefining, No. 5(2), 2011, pp. 115-126.
Roman-Leshkov et al., "Mechanism of Glucose Isomerization Using a Solid Lewis Acid Catalyst in Water," *Angew. Chem. Int. Ed.*, 2010, 49:8954-8957.
Salak, et al., "Kinetics of the Decomposition of Fructose Catalyzed by Hydrochloric Acid in Subcritical Water: Formation of 5-Hydroxymethylfurfural, Levulinic, and Formic Acids", Ind. Eng. Chem. Res. No. 46, 2007, pp. 7703-7710.
Schuette, et al., "Normal Valerolactone. III. Its Preparation by the Catalytic Reduction of Levulinic Acid With Hydrogen in the Presence of Platinum Oxide", Preparation of n-Valerolactone, vol. 52, Jul. 1930, pp. 3010-3012.
Shaw, et al., "Acid catalyzed degradation of d-fructose", Carbohydrate Research, No. 5, 1967, pp. 266-273.
Sriram, et al., "Identification of hexose hydrolysis products in metabolic flux analytes: A case study of levulinic acid in plant protein hydrolysate", Metabolic Engineering, No. 9, 2007, pp. 442-451.
Taherzadeh, et al., "Characterization and Fermentation of Dilute-Acid Hydrolyzates From Wood", Ind. Eng. Chem. Res., No. 36, 1997, pp. 4659-4665.
Thomas, et al., "Studies on Levulinic Acid. I. Its Preparation From Carbohydrates by Digestion with Hydrochloric Acid Under Pressure", Preparation of Levulinic Acid, vol. 53, 1931, pp. 2324-2328.
Uslu, et al., "Equilibrium Studies of Extraction of Levulinic Acid by (Trioctylamine (TOA) = Ester) Solvents", J. Chem. Eng. Data, No. 53, 2008, pp. 1557-1563.
Uslu, et al., "Reactive Extraction of Levulinic Acid by Amberlite LA-2 Extractant", J. Chem. Eng. Data, No. 54, 2009, pp. 712-718.
Van Dam, et al ."The Conversion of Fructose and Glucose in Acidic Media-Formation of Hydroxymethylfurfural", Starch 38, Nr. 3, S, 1986, pp. 95-101.
Watts, "A Dictionary of Chemistry and the Allied Branches of Other Sciences", 1881, pp. 1181-1182.
Weiss, et al., "The Enzymatic Synthesis of Triglycerides", Communications to the Editor, vol. 78, 1956, p. 3550
Yamada, et al., "Characterization of the products resulting from ethylene glycol liquefaction of cellulose", J. Wood. Sci., No. 47, 2001, pp. 458-464.
Yanada, et al., "Rapid liquefaction of lignocellulosic waste by using ethylene carbonate", Biosource Technology, No. 70, 1999, pp. 61-67.
Zhao, et al., "Effects of Crystallinity on Dilute Acid Hydrolysis of Cellulose by Cellulose Ball-Mining Study", Energy & Fuels, No. 20, 2006, pp. 807-811.
Zhao, et al., "Metal Chlorides in Ionic Liquid Solvents Convert Sugars to 5-Hydroxymethylfurfural" Science, vol. 316, Jun. 15, 2007, pp. 1597-1600.
Brasholz et al., "Highly efficient dehydration of carbohydrates to 5-(chloromethyl)furfural (CMF), 5-(hydroxymethyl)furfural (HMF) and levulinic acid by biphasic continuous flow processing," *Green Chem.*, 2011, 13:1114-1117.

* cited by examiner

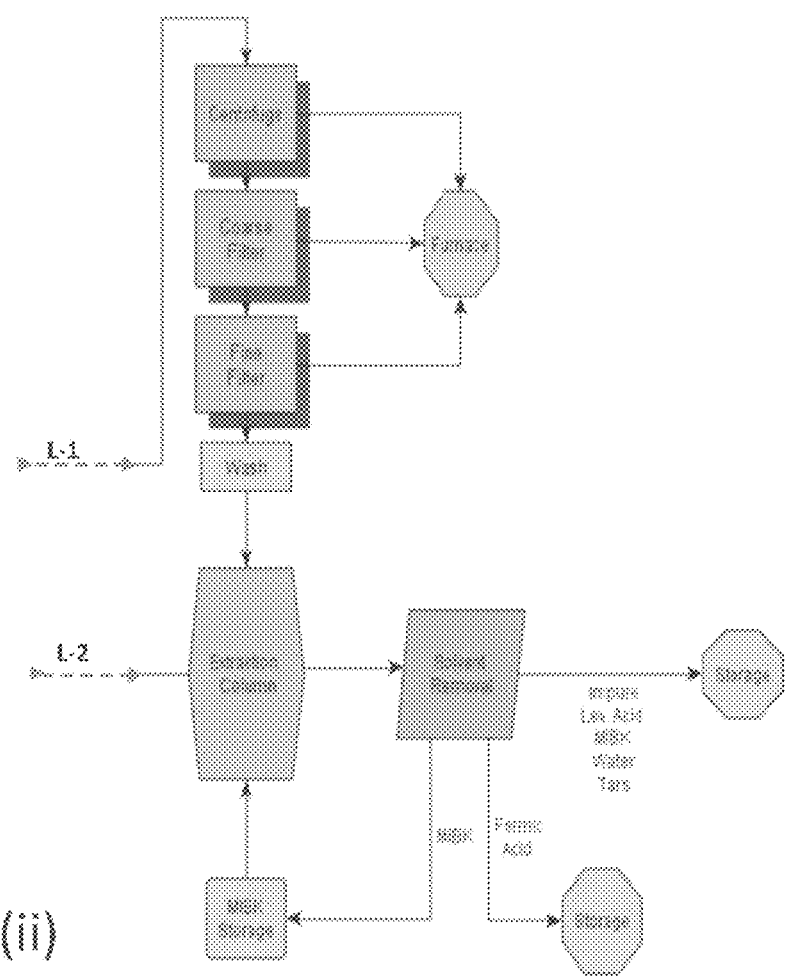
Figure 1b(ii)

Sample Prep

- Solvent Extraction
  - Add approx. 250 mg to scintillation vial + 5-10mL "good" solvent
  - Remove soluble fraction and dry insoluble fraction

- $^1$H NMR analysis for soluble fraction
  - TGA of insoluble fraction

Figure 2a

Char – Soluble and Insoluble Fractions

| Sample | Mass Char (g) | Solvent | Mass Solvent (g) | Insoluble Mass (g) | Insol. % | Sol. %* |
|---|---|---|---|---|---|---|
| A | 0.2974 | DMF | 13.2 g | 0.1690 g | 56.8 % | 43.2 % |
| B | 0.3256 | DMSO | 13.3 g | 0.2177 | 66.9 % | 33.1 % |
| C† | 0.2799 | MIBK | 6.4 g | 0.1977 | 70.6 % | 29.4 % |
| D | 0.2798 | Cyclohexanone | 6.4 | 0.2243 | 80.2 % | 19.8 % |

*Calculated values. Not measured directly
† Second extraction with DMSO extracted an additional 5 % (based on original mass)

Figure 2b

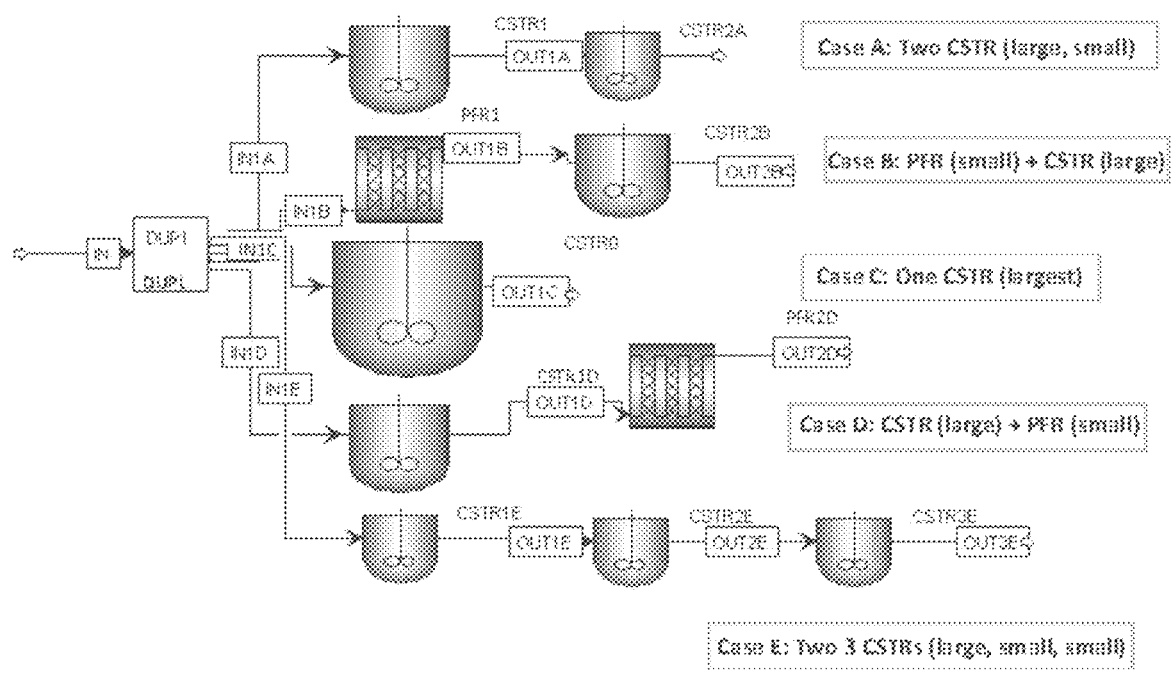
Figure 3-Aspen Flowsheet used for the modeling study

PROCESS TO PREPARE LEVULINIC ACID

CROSS REFERENCE TO RELATED APPLICATIONS

This application is a continuation of U.S. patent application Ser. No. 14/359,124, filed May 19, 2014, which is a national phase application under 35 U.S.C. 371 of International Application No. PCT/US2012/066368, filed Nov. 21, 2012, which claims the benefit of U.S. Provisional Patent Application No. 61/722,766, filed Nov. 5, 2012. U.S. Provisional Patent Application No. 61/581,006, filed Dec. 28, 2011, U.S. Provisional Patent Application No. 61/576,818, filed Dec. 16, 2011, and U.S. Provisional Patent Application No. 61/563,276, filed Nov. 23, 2011. The entire contents of each of the referenced applications are incorporated into the present application by reference in their entirety.

FIELD OF THE INVENTION

The invention relates generally to the preparation and purification of levulinic acid.

BACKGROUND OF THE INVENTION

Levulinic acid can be used to make resins, plasticizers, specialty chemicals, herbicides and as a flavor substance. Levulinic acid is useful as a solvent, and as a starting material in the preparation of a variety of industrial and pharmaceutical compounds such as diphenolic acid (useful as a component of protective and decorative finishes), calcium levulinate (a form of calcium for intravenous injection used for calcium replenishment and for treating hypocalcemia). The use of the sodium salt of levulinic acid as a replacement for ethylene glycols as an antifreeze has also been proposed.

Esters of levulinic acid are known to be useful as plasticizers and solvents, and have been suggested as fuel additives. Acid catalyzed dehydration of levulinic acid yields alpha-angelica lactone.

Levulinic acid has been synthesized by a variety of chemical methods. But levulinic acid has not attained much commercial significance due in part to the high cost of the raw materials needed for synthesis. Another reason is the low yields of levulinic acid obtained from most synthetic methods. Yet, another reason is the formation of a formic acid byproduct during synthesis and its separation from the levulinic acid. Therefore, the production of levulinic acid has had high associated equipment costs. Despite the inherent problems in the production of levulinic acid, however, the reactive nature of levulinic acid makes it an ideal intermediate leading to the production of numerous useful derivatives.

Cellulose-based biomass, which is an inexpensive feedstock, can be used as a raw material for making levulinic acid. The supply of sugars from cellulose-containing plant biomass is immense and replenishable. Most plants contain cellulose in their cell walls. For example, cotton comprises 90% cellulose. Furthermore, it has been estimated that roughly 75% of the approximate 24 million tons of biomass generated on cultivated lands and grasslands are waste. The cellulose derived from plant biomass can be a suitable source of sugars to be used in the process of obtaining levulinic acid. Thus, the conversion of such waste material into a useful chemical, such as levulinic acid, is desirable.

BRIEF SUMMARY OF THE INVENTION

A major issue in producing levulinic acid is the separation of pure levulinic acid from the byproducts, especially from formic acid and char. Current processes generally require high temperature reaction conditions, generally long digestion periods of biomass, specialized equipment to withstand hydrolysis conditions, and as a result, the yield of the levulinic acid is quite low, generally in yields of 10 percent or less.

Therefore, a need exists for a new approach that overcomes one or more of the current disadvantages noted above.

The present invention surprisingly provides novel approaches to more efficiently prepare levulinic acid in commercial quantities with high yields and high purities. Additionally, the production of hydroxymethylfurfural is also described, which is an important intermediate to the product of levulinic acid.

In one aspect, the use of a water insoluble cosolvent in the processes improves the yields of the hydroxymethylfurfural or levulinic acid and helps to reduce undesired byproducts. In another aspect, the use of high concentration of acid, e.g., about 20-50 weight percent based on the total weight of reaction components and low reaction temperature (approximately 50-100° C.) helps to improve yield of desired products with reduction of undesired byproducts.

In one aspect, HMF can be prepared first followed by a second step to prepare the levulinic acid.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIGS. 2a through 2e provide information regarding recovery of levulinic acid from Char, soluble and insoluble fractions. It was surprisingly found that extraction of the char provided levulinic acid almost exclusively, helping to further improve the production of levulinic acid.

FIG. 3 provides an aspen flowsheet diagram depicting various reactor configurations.

DETAILED DESCRIPTION

Figure 1A:
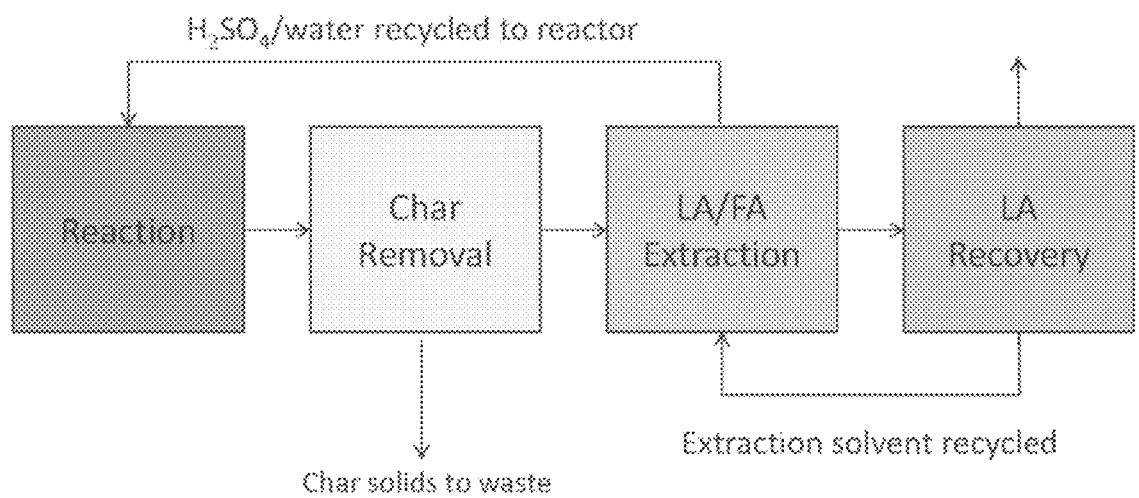
FIG. 1a is a flow diagram of one embodiment for a process to prepare and/or purify levulinic acid.

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention provides various advantages in the preparation of levulinic acid, hydroxymethyl furfural and/or formic acid. The following list of advantages is not meant to be limiting but highlights some of the discoveries contained herein.

First, a biomass material can be used as the initial feedstock to prepare the levulinic acid, hydroxymethyl furfural and/or formic acid. This ability provides great flexibility in obtaining a constant source of starting material and is not limiting.

Second, the biomass can be a refined material, such as fructose, glucose, sucrose, mixtures of those materials and the like. As such, there is a plentiful supply of materials that can be converted into the ultimate product(s). For example, sugar beets or sugar cane can be used as one source. Fructose-corn syrup is another readily available material. Use of such materials thus helps to reduce the costs to prepare the desired products.

Third, it has been discovered that use of high concentrations of acid(s), generally about 20 weight percent or more (based on the total mass of the reaction medium) provides a cleaner reaction product with less char and unwanted byproducts. It has also been found that use of high concentrations of acid(s), generally up to 75 weight percent or more, (based on the total mass of the reaction medium) provides faster reaction times than lower acid concentrations used with the same reaction conditions.

Fourth, it has also been discovered that with the use of higher concentrations of acid, the reaction conditions can be conducted at much lower temperatures than are currently utilized in the literature. Again, this lessens the amount of char and byproducts from the reaction(s) that take place and increases the yield of the desired product(s).

Figure 5A:
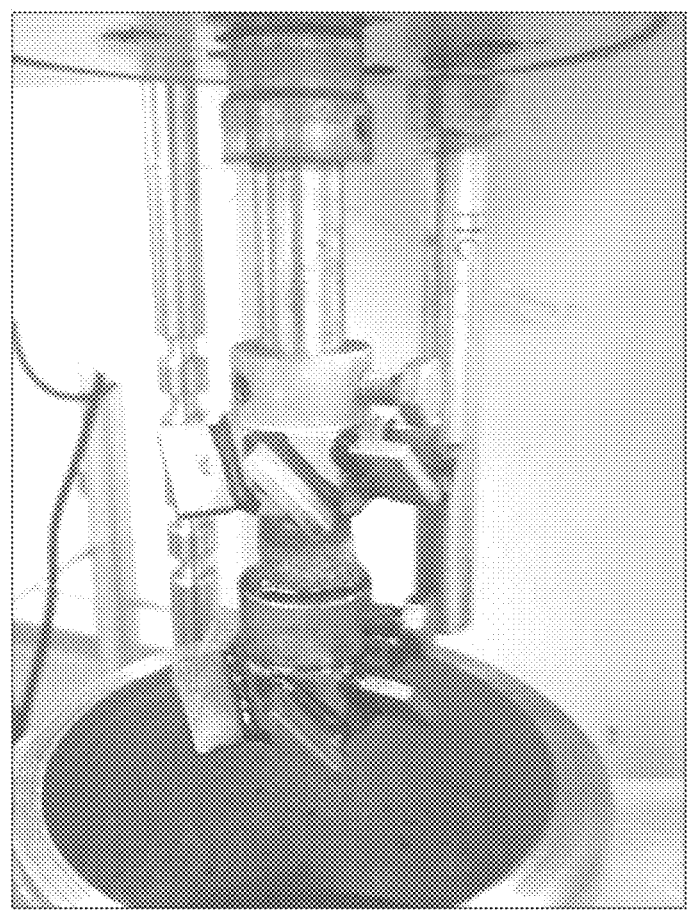
FIGS. 5a through 5c are pictures showing reactor components after production of levulinic acid in accordance with the present invention.
Figure 5B:
Figure 5C:
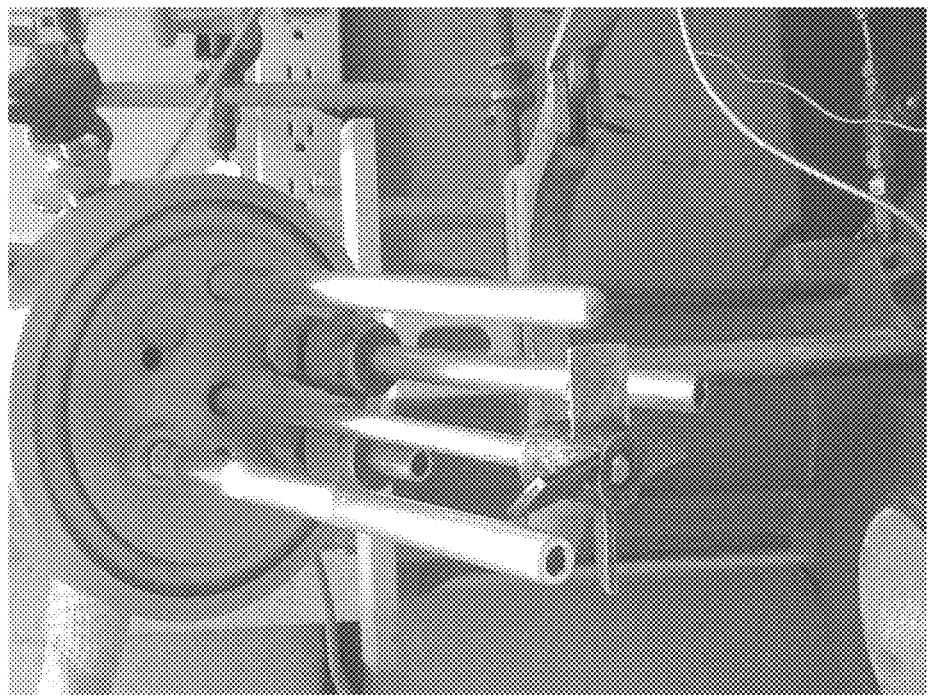
Figure 5D:
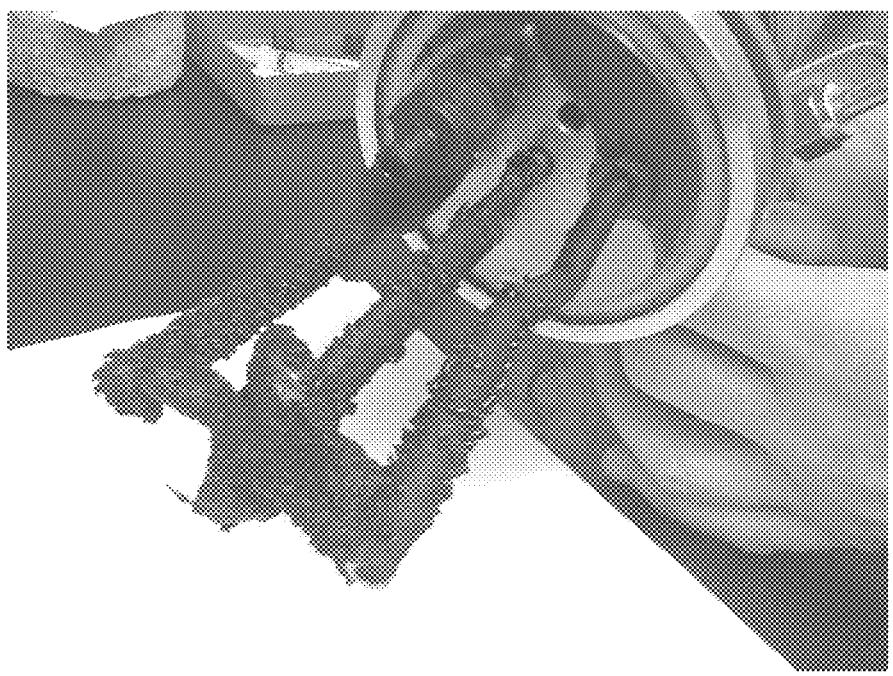
FIGS. 5d through 5g are pictures showing reactor components after production of levulinic acid in accordance with the prior art.
Figure 5E:
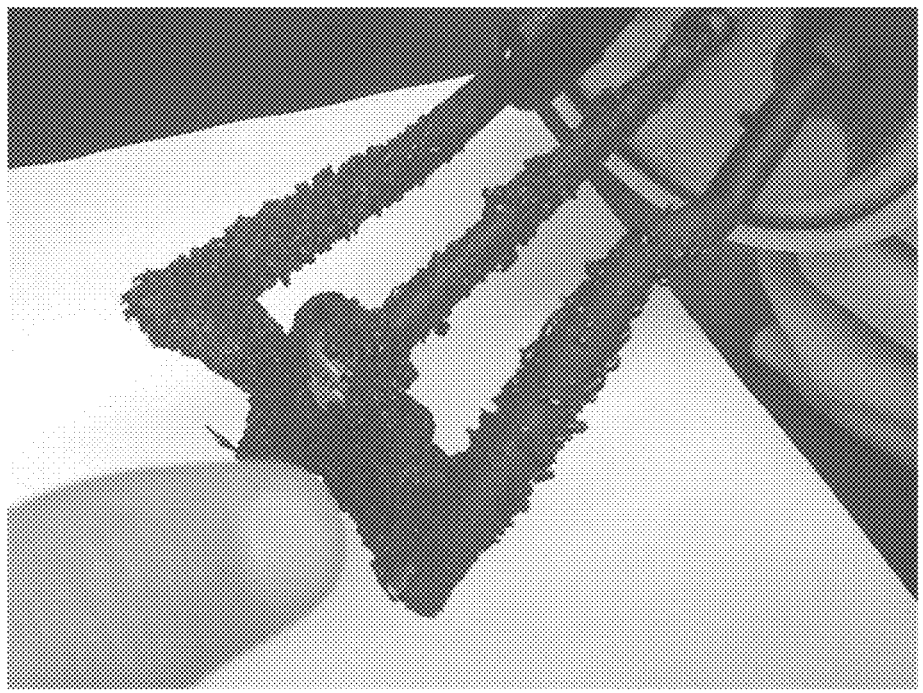
Figure 5F:
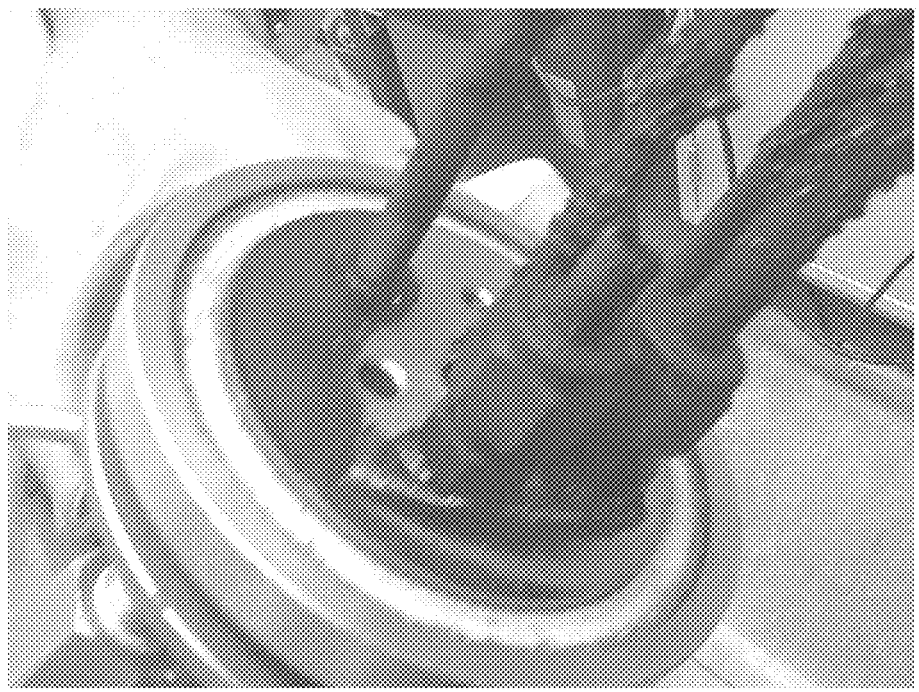
Figure 5G:

Fifth, it has also been discovered that with the methods of the present invention, the char that is created is much easier to remove from the reactor. For example, FIGS. 5a, 5b and 5c depict internal PARR reactor components after carrying out methods according to the present invention with no additional cleaning. As can be seen in the photographs, there is little to no char accumulated on the reactor components. In comparison, FIGS. 5d through 5g depict internal PARR reactor components after carrying out methods according to the prior art with no additional cleaning. As can be seen, there is significant char build up on the reactor components requiring large cleanup efforts.

Sixth, it has been advantageously found to treat the biomass material(s) in an aqueous environment with a water immiscible solvent. Not to be limited by theory, it is believed that the partitioning of the starting materials from the product(s) between the aqueous and non-aqueous layers provides for one or more of: increased yield, reduced charring and/or by-products, faster reaction times and reduced reaction temperatures.

Seventh, it has also been found that the advantages of the new process conditions, including continuous addition of the biomass over a period of time during the reaction can be incorporated into existing processes to improve yield, reduce costs, improve efficiency and improve purity of product(s).

Eighth, the processes described herein can be performed via CSTR or continuous batch process conditions.

In one embodiment. This process uses a high concentration of sulfuric acid, which has several distinct advantages. For one, the reactions can be run at lower temperatures compared to low acid processes and still hydrolyze the sugars in a reasonable time frame. It has been discovered that under these high acid, low-temperature reaction conditions (e.g., 80° C.-110° C.), the char byproduct that is formed is in the form of suspended particles that are easier to remove from the reactor and that can be filtered from the liquid hydrolysate product stream. In contrast, with low acid conditions, high temperature is required to effectively hydrolyze the sugar in a reasonable time frame and those conditions produce a char byproduct that coats the reactor components in such a manner that it is difficult to remove, and for the most part does not stay suspended in the reaction mixture. This high-acid reaction strategy, however, makes it difficult to isolate the organic acid products (levulinic acid and formic acid) from the inorganic acid reagent. When small amounts of sulfuric acid are used, as is typical in the prior art, the strong inorganic acid can effectively be neutralized to its salt form by careful addition of stoichiometric amounts of base. At the high acid contents used here, however, the quantity of salt produced would be excessive. Likewise, the use of an ion exchange column is impractical because the large quantity of inorganic acid would quickly fill the capacity of the column.

Solvent extraction techniques, where the organic acids are preferably extracted into an organic solvent, are preferred. Even here, the high mineral acid content poses challenges. The organic solvent should be insoluble in the aqueous phase, but in some cases, the sulfuric acid can drive compatibility of the organic solvent and the aqueous phase. When this happens, a portion of the organic solvent becomes soluble in the concentrated sulfuric acid aqueous phase and the risk of solvent loss to side reactions increases. Even if the organic solvent is stable in the aqueous sulfuric acid phase, the organic solvent must be recovered from the aqueous stream for recycling to the extraction unit for optimized economics. High mineral acid concentration also carries with it the potential for higher mineral acid concentrations in the organic phase. When this happens, there is the risk of solvent loss to side reactions with the mineral acid, particularly in the case when the organic stream is heated to distill the organic solvent. Therefore, solvent extraction of the organic acid products should ideally have at least some of the following characteristics:

little to no miscibility with water;
little to no miscibility with the mineral acid;
selectively partition the organic acids into the organic solvent phase;
have low partitioning of the mineral acid into the organic solvent phase;
have low reactivity between the organic extraction solvent and the mineral acid;
have low reactivity between the organic extraction solvent & the organic acid products;

have the ability to remove or reduce any mineral acid that partitions into the organic phase;

easy to remove from organic acid, such as by backwashing or distillation:

allow the neutralization the organic acids.

In one embodiment, the partition coefficient of the extraction solvent for levulinic acid is at least 0.3, more specifically, at least 0.5, more specifically, at least 0.7, more specifically, at least 1.0, more specifically at least 1.3, more specifically, at least 1.5 more specifically, at least 1.7, and more specifically at least 2.0. In one embodiment, the partition coefficient of the extraction solvent for formic acid is at least 0.3, more specifically, at least 0.5, more specifically, at least 0.7, more specifically, at least 1.0, more specifically at least 1.3, more specifically, at least 1.5 more specifically, at least 1.7, and more specifically, at least 2.0, more specifically, at least 2.3, more specifically, at least 2.5, more specifically, at least 3.0, more specifically, at least 3.5, more specifically, at least 4.0, more specifically, at least 5.0 more specifically, at least 6.0, more specifically, at least 7.0, more specifically, at least 8.0, and more specifically, at least 9.0.

In one embodiment, to conduct a CSTR reaction with a given "residence time" t (in this case, t=typically 30 min to 1 hour) the volume of the reactor is selected such that the typical "residence time" of the reactants is the designed target. The mass of material held in the reactor is designed to be the product of the mass flow rate into the reactor and the residence time. Longer residence time=larger quantity of material held in the reactor. Slower feed rate=smaller quantity of material held in the reactor. In operation, it is desirable for the feed to be a constant flow rate and composition; also the exit stream is a constant flow rate and composition, and the sum of the flow rates of all exit streams equals the flow rate of the feeds (on a mass basis).

Typically, the reactor goes through a start-up phase until the reactor achieves "steady state" wherein the reactor contents, temperature, and pressure only varies within a controlled range. After steady state is achieved, the reactor is continuously operated as long as desired (days, weeks, months, years). During operation, the feed is steady, and the exit stream is steady. The reactor contents are steady. But the average residence time of the reactor contents is designed and held constant. The reactor content composition is equal to the composition of the exit streams.

During the startup phase, many strategies can be used to reach steady state as quickly as possible. For example, the reactor contents may be started as 100% water, or fed with the desired steady state composition of the reactor contents. The composition of the feed streams can be allowed to vary, and the flow rate of the exit stream may be varied to achieve steady state (anywhere from zero to equal to the feed rate).

It has been observed that the production of HMF could potentially lead to large amounts of undesirable char build up. For example, a CSTR design which is inadvertently designed so as to run at conditions which give a high HMF yield, could be expected to yield high char and discouraging results.

It is thus, one technical advantage of one embodiment of the invention to provide a continuous reaction system in such a way to minimize the HMF concentration.

It has been observed in a batch reaction wherein the HMF concentration starts out at zero, builds to a peak, and then declines again to very low levels. In a simple batch reaction, such a profile is difficult to avoid. Likewise, a single, continuous, plug-flow reactor could experience a similar HMF concentration along the length of the tube. The inventors have found that in one embodiment, a carefully designed reaction system (for example, an initial CSTR followed by a plug flow reactor) could avoid having a high HMF concentration and still achieve high conversion.

The following paragraphs provide for various aspects of the present invention. In one embodiment, in a first paragraph (1), the present invention provides a process to prepare levulinic acid comprising the steps:

a) heating an aqueous solution of a mineral acid to about 60° C. to about 110° C. in a reactor; and b) adding high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof to the heated aqueous acid in the reactor over a period of time to form a reaction mixture including levulinic acid. In one embodiment, the high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof that are added to the reaction mixture over time comprises from about 0.1 to about 25, more specifically, from about 1 to about 20 and even more specifically from about 4 to about 15 percent by weight of the final mass of the reaction mixture. It is understood that as the sugar streams are added to the reactor, the sugar will continuously react with the mineral acid to form levulinic acid and other materials. Thus, the final reaction mixture may contain less than the described ranges of sugars. In another embodiment, the steady state concentration of the high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof in the reaction mixture is from about 0.1 to about 25, more specifically, from about 1 to about 20 and even more specifically from about 4 to about 15 percent by weight.

2. The process of paragraph 1, wherein the mineral acid is sulfuric acid ($H_2SO_4$), hydrochloric acid (HCl), hydrobromic acid (HBr) or hydroiodic acid (HI).

3. The process of paragraphs 1 or 2, wherein the mineral acid percentage by weight is from about 5 to about 80 percent of the reaction mixture.

4. The process of paragraphs 1 or 2, wherein the mineral acid percentage by weight is from about 20 to about 80 percent of the reaction mixture.

5. The process of paragraphs 1 or 2, wherein the mineral acid percentage by weight is from about 20 to about 50 percent of the reaction mixture.

6. The process of any of paragraphs 1 through 5, wherein the high fructose corn syrup is present between about 1 and about 99 weight percent of fructose and from about 99 to about 1 weight percent glucose with the remainder water, wherein the sugar content is between about 1 and about 99% by weight.

7. The process of any of paragraphs 1 through 6, wherein the high fructose corn syrup is added over a period of from about 0.1 to about 40 hours.

8. The process of either of paragraphs 1 through 5, wherein the mixture of at least two different sugars is between about 1 and about 99 weight percent of fructose and from about 99 to about 1 weight percent glucose with the remainder water, wherein the sugar content is between about 20 and about 90% by weight.

9. The process of any of paragraphs 1 through 5 or 7, wherein the mixture of at least two different sugars is added over a period of from about 0.1 to about 40 hours.

10. The process of any of paragraphs 1 through 5, wherein the aqueous mixture of fructose and glucose is between about 1 and about 99 weight percent of fructose and from about 99 to about 1 weight percent glucose with the remainder water, wherein the sugar content is between about 30 and about 85% by weight.

11. The process of any of paragraphs 1 through 5 or 10, wherein the aqueous mixture of fructose and glucose is added over a period of from about 0.1 to about 40 hours.

12. The process of either of paragraphs 1 through 5, wherein the aqueous solution of fructose contains from about 1 to about 100 percent fructose by weight.

13. The process of any of paragraphs 1 through 5 or 12, wherein the aqueous solution of fructose is added over a period of from about 0.1 to about 40 hours.

14. The process of either of paragraphs 1 through 5, wherein the aqueous solution of hydroxymethylfurfural contains from about 0.1 to about 100 percent hydroxymethylfurfural by weight.

15. The process of any of paragraphs 1 through 5 or 14, wherein the aqueous solution of hydroxymethylfurfural is added over a period of from about 0.1 to about 40 hours.

16. The process of any of paragraphs 1 through 5, wherein the aqueous mixture of fructose and HMF contains from about 0.1 to about 99.9 parts fructose, from about 99.9 to about 0.1 parts hydroxymethylfurfural and from about 10 to about 99.8 parts water by weight.

17. The process of any of paragraphs 1 through 5 or 16, wherein the aqueous mixture of fructose and hydroxymethylfurfural is added over a period of from about 0.1 to about 40 hours.

18. The process of any of paragraphs 1 through 5, wherein the aqueous mixture of glucose contains from about 0.1 to about 99.9 parts glucose and from about 0.1 to about 99.9 parts water by weight.

19. The process of any of paragraphs 1 through 5 or 18, wherein the aqueous mixture of glucose is added over a period of from about 0.1 to about 40 hours.

20. The process of any of paragraphs 1 through 5, wherein the aqueous mixture of maltose contains from about 0.1 to about 99.9 parts maltose and from about 0.1 to about 99.9 parts water by weight.

21. The process of any of paragraphs 1 through 5 or 20, wherein the aqueous mixture of maltose is added over a period of from about 0.1 to about 40 hours.

22. The process of any of paragraphs 1 through 5, wherein the aqueous mixture of inulin contains from about 0.1 to about 99.9 parts inulin and from about 0.1 to about 99.9 parts water by weight.

23. The process of any of paragraphs 1 through 5 or 22, wherein the aqueous mixture of inulin is added over a period of from about 0.1 to about 40 hours.

24. The process of any of paragraphs 1 through 5, wherein the aqueous mixture of polysaccharides contains from about 0.1 to about 99.9 parts polysaccharides and from about 0.1 to about 99.9 parts water by weight.

25. The process of any of paragraphs 1 through 5 or 24, wherein the aqueous mixture of polysaccharides is added over a period of from about 0.1 to about 40 hours.

26. The process of any of paragraphs 1 through 25, wherein the aqueous solution of mineral acid is stirred.

27. The process of any of paragraphs 1 through 26, wherein the mixture is heated for an additional period of time from about 0.1 hour to about 20 hours at a temperature range of from about 25° C. to about 110° C.

28. The process of any of paragraphs 1 through 27, wherein the mixture is optionally cooled to ambient temperature.

29. The process of any of paragraph 1 through 28, further comprising the step of heating the mixture to a temperature of from about 25° C. to about 160° C. to reduce any residual glucose levels.

30. The process of either paragraphs 1 through 29, wherein the aqueous mixture comprises fructose and the levulinic acid is produced in greater than about 65% molar yield, optionally greater than about 75%, optionally greater than about 80%, optionally greater than 85%, optionally greater than 90%.

31. The process of either paragraphs 1 through 29, wherein the aqueous mixture comprises glucose and the levulinic acid is produced in greater than about 45% molar yield, optionally greater than about 50%, optionally greater than about 55%, optionally greater than 60%, optionally greater than 65%.

32. The process of any of paragraphs 1 through 31, wherein any remaining fructose is not detected by liquid chromatography.

33. The process of any of paragraphs 1 through 32, wherein any remaining hydroxymethylfurfural is present at less than 0.5 weight percent in the levulinic acid product.

34. The process of any of paragraphs 1 through 33, wherein ratio of the mass of levulinic acid to the mass of dry solids is greater than 1:1.

35. The process of any of paragraphs 1 through 34, wherein less than 5 weight percent of dry char is produced relative to the entire weight of the mixture.

36. The process of any of paragraphs 1 through 35, further comprising filtering out solids from the mixture including levulinic acid to provide a first filtrate. In one embodiment, the filter is a candle filter, a Neutche filter, a basket centrifuge, membrane filters, or a cartridge filter.

37. The process of paragraph 36, wherein filtering is carried out with filter media having pore size less than 30 microns.

38. The process of paragraph 36, wherein filtering is carried out with filter media having pore size less than 20 microns.

39. The process of any of paragraphs 1 through 38, further comprising combining the mixture comprising levulinic acid with an extraction solvent to create an extraction phase and a raffinate phase.

40. The process of paragraph 39, wherein the extraction solvent has a partition coefficient for levulinic acid from water of at least 0.3, optionally at least 0.5, optionally at least 1.0, optionally at least 1.5, and optionally at least 2.0.

41. The process of paragraph 39 wherein the extraction solvent has a partition coefficient for formic acid from water of at least 0.3, optionally at least 0.5, optionally at least 1.0, optionally at least 1.5, optionally at least 2.0, optionally at least 5.0, optionally at least 7.0 and optionally at least 9.0.

42. The process of any of paragraphs 39 through 41 wherein the extraction solvent is selected from the group consisting of methyl iosamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, guaiacol, 2-sec butyl phenol, nonyl phenol, methylene chloride, methyl isobutyl carbinol, anisol, ethylene glycol di-n-butyl ether, castor oil, m-cresol, p-cresol, o-cresol, cresol mixtures, 60/40 m-cresol/p-cresol, 75/25 m-cresol/p-cresol, diethyl carbonate, methyl salicylate, 2,4-dimethyl phenol and mixtures thereof.

43. The process of any of paragraphs 39 through 42, further comprising recycling the raffinate phase to the reactor.

44. The process of paragraph 43, further comprising heating the raffinate phase from 120-180° C. In one embodiment, the method further comprises removing any additional solids that are formed, preferably by filtration.

45. The process of paragraph 44, further comprising cooling the raffinate phase to less than 110° C. In one embodiment, the method further comprises removing any additional solids that are formed, preferably by filtration.

46. The process of paragraph 45, further comprising adding high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof to the raffinate phase in the reactor over a period of time to form a mixture including levulinic acid.

47. The process of any of paragraphs 39 through 46, further comprising separating levulinic acid, formic acid, or both from the extraction solvent.

48. The process of any of paragraphs 36 through 47, wherein the solids are washed with water to provide a second filtrate and the first and second filtrates are combined to form a final filtrate. In other embodiments the solids are washed with water to provide a second filtrate and the first and second filtrates are not combined.

49. The process of any of paragraphs 1 through 48, wherein the reactor is a batch reactor.

50. The process of any of paragraphs 1 through 48, wherein the reactor is one or more CSTRs.

51. A process to prepare levulinic acid comprising the steps:
a) heating an aqueous solution of a mineral acid to about 60° C. to about 110° C.; b) adding a first aqueous mixture comprising fructose and glucose to the heated aqueous mineral acid over a period of time to form a mixture including levulinic acid;
c) optionally cooling the mixture to room temperature; and
d) heating the mixture, optionally in a sealed reactor, from about 25° C. to about 160° C. under pressure of 75 psi or below;
e) optionally cooling the heated mixture of step d) to room temperature; and
f) filtering the mixture to provide a first filtrate and solids. In one embodiment, the aqueous mixture comprising fructose and glucose are added to the reaction mixture over time comprise from about 0.1 to about 25, more specifically, from about 1 to about 20 and even more specifically from about 4 to about 15 percent by weight of the final mass of the reaction mixture. It is understood that as the sugar streams are added to the reactor, the sugar will continuously react with the mineral acid to form levulinic acid and other materials. Thus, the final reaction mixture may contain less than the described ranges of sugars. In another embodiment, the steady state concentration of the aqueous mixture comprising fructose and glucose in the reaction mixture is from about 0.1 to about 25, more specifically, from about 1 to about 20 and even more specifically from about 4 to about 15 percent by weight.

52. The process of paragraph 51, wherein the mineral acid is acid is sulfuric acid ($H_2SO_4$), hydrochloric acid (HCl), hydrobromic acid (HBr) or hydroiodic acid (HI).

53. The process of either paragraphs 51 or 52, wherein the mineral acid percentage by weight is from about 5 to about 80 percent of the mixture including levulinic acid.

54. The process of any of paragraphs 51 through 52, wherein the solids can be washed more than once to provide additional filtrates to be combined with the first filtrate to form a final filtrate.

55. The process of any of paragraph 50 through 52, wherein the final filtrate is treated with a water immiscible solvent to form a water immiscible layer and a raffinate.

56. The process of paragraph 55, wherein the water immiscible layer is separated from the aqueous layer and subjected to distillation.

57. The process of any of paragraphs 55 or 56, wherein the water immiscible solvent is selected from the group consisting of methyl iosamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, guaiacol, 2-sec butyl phenol, nonyl phenol, methylene chloride, methyl isobutyl carbinol, anisol, ethylene glycol di-n-butyl ether, castor oil, m-cresol, p-cresol, o-cresol, cresol mixtures, 60/40 m-cresol/p-cresol, 75/25 m-cresol/p-cresol, diethyl carbonate, methyl salicylate, 2,4-dimethyl phenol and mixtures thereof.

58. The process of either of paragraphs 56 or 57, wherein the distillation is performed under vacuum to afford a levulinic acid product.

59. The process of any of paragraphs 55 through 58, further comprising the steps:
a) combining the raffinate, and optionally a mineral acid with water to form a mixture comprising from about 5 to about 80% mineral acid;
b) heating the mixture to about 80° C. to about 110° C.;
c) adding a second aqueous solution of aqueous mixture of fructose and glucose to the mixture over a period of from about 0.1 to about 40 hours.

60. The process of paragraph 59, wherein any of paragraphs 51 through 59 are repeated one or more times.

61. An industrial process to process to prepare levulinic acid comprising the integrated steps of reaction, solids filtration, extraction, distillation, and recycling of any of paragraphs 1 through 60.

62. The process of paragraph 51 further comprising the step of adding a filter aid to the reaction mixture prior to solids removal by filtration or centrifugation.

63. The process of any of paragraphs 51 through 62, wherein the mixture including levulinic acid is filtered through a 0.1 micron filter to about a 30 micron filter.

64. The process of any of paragraphs 51 through 63, wherein the mixture comprising levulinic acid is subjected to process conditions, wherein the water, mineral acid, the water immiscible solvent and optionally levulinic acid is recycled.

65. The process of any of paragraphs 51 through 63 are carried out in a batch reactor.

66. The process of any of paragraphs 51 through 63 are carried out in a CSTR.

67. A process to prepare levulinic acid comprising the steps:
a) heating an aqueous solution of a mineral acid to about 60° C. to about 110° C.;
b) adding high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof to the heated aqueous mineral acid over a period of time to form a reaction mixture in a reactor to form a mixture including levulinic acid and solids;
c) filtering the solids from the mixture, optionally after cooling;
d) adding a water immiscible liquid to the mixture so that the mixture forms first and second layers, wherein greater than 90% of the mineral acid is in the first layer and greater than 90% of the water immiscible liquid is in the second layer;
e) recovering levulinic acid and optionally formic acid from the second layer, and
f) recycling the first layer back to the reactor. In one embodiment, the high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof are added to the reaction mixture over time comprise from about 0.1 to about 25, more specifically, from about 1 to about 20 and even more specifically from about 4 to about 15 percent by weight of the final mass of the reaction mixture. It is understood that as the sugar streams are added to the reactor, the sugar will continuously react with the mineral acid to form levulinic acid and other materials. Thus, the final reaction mixture may contain less than the described ranges of sugars. In another embodiment, the steady state concentration of the high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof in the reaction mixture is from about 0.1 to about 25, more specifically, from about 1 to about 20 and even more specifically from about 4 to about 15 percent by weight.

68. The process of paragraph 67, further comprising heating the first layer from about 120° C. to about 180° C. for a period of time.

69. The process of paragraph 68, further comprising cooling the first layer to below 100° C.

70. The process of any of paragraphs 67 through 69, wherein the mineral acid is selected from the group consisting of sulfuric acid, hydrochloric acid, hydrobromic acid, hydroiodide and combinations thereof.

71. The process of paragraph 70, wherein the mineral acid is sulfuric acid.

72. The process of any of paragraphs 67 through 71, wherein the mineral acid percentage by weight is from about 5 to about 80 percent of the reaction mixture.

73. The process of paragraph 72, wherein the mineral acid percentage by weight is from about 20 to about 80 percent of the reaction mixture.

74. The process of paragraph 72, wherein the mineral acid percentage by weight is from about 20 to about 50 percent of the reaction mixture.

75. The process of paragraph 71, wherein the mineral acid percentage by weight is from about 40 to about 80 percent of the reaction mixture.

76. The process of any of paragraphs 67 through 75, wherein the first layer is heated for a period of time sufficient to convert greater than 90% of any glucose into levulinic acid.

77. The process of any of paragraphs 67 through 76, wherein the water immiscible liquid is selected from the group consisting of methyl iosamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, guaiacol, 2-sec butyl phenol, nonyl phenol, methylene chloride, methyl isobutyl carbinol, anisol, ethylene glycol di-n-butyl ether, castor oil, m-cresol, p-cresol, o-cresol, cresol mixtures, 60/40 m-cresol/p-cresol, 75/25 m-cresol/p-cresol, diethyl carbonate, methyl salicylate, 2,4-dimethyl phenol and mixtures thereof.

78. The process of any of paragraphs 67 through 77, wherein the high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures added over a period of from about 0.1 to about 40 hours.

79. The process of any of paragraphs 67 through 78, wherein the mixture is heated for an additional period of time from about 0.1 hour to about 20 hours at a temperature range of from about 25° C. to about 110° C.

80. The process of either paragraphs 67 through 79, wherein the mixture comprises fructose and the levulinic acid is produced in greater than about 65% molar yield, optionally greater than about 75%, optionally greater than about 80%, optionally greater than 85%, optionally greater than 90%.

81. The process of either paragraphs 67 through 79, wherein the aqueous mixture comprises glucose and the levulinic acid is produced in greater than about 45% molar yield, optionally greater than about 50%, optionally greater than about 55%, optionally greater than 60%, optionally greater than 65%.

82. The process of any of paragraphs 67 through 81, wherein the mass of levulinic acid to the mass of solids ratio is greater than 1:1.

83. The process of any of paragraphs 67 through 82, wherein less than 5 weight percent of dry char is produced relative to the entire weight of the mixture.

84. The process of any of paragraphs 67 through 83, wherein the solids that are formed do not adhere to glass, Teflon or metal surfaces.

85. The process of paragraph 84, wherein the metal surface is a hastelloy metal surface, alloy 20 metal surface, alloy 2205 metal surface, AL6XN metal surface or zirconium metal surface.

86. The process of any of paragraphs 67 through 85, wherein the reactor is batch reactor.

87. The process of any of paragraphs 67 through 85, wherein the reactor is a CSTR.

The following paragraphs also provide for various aspects of the present invention. In one embodiment, in a first paragraph (1), the present invention provides a process to prepare levulinic acid or 5-(hydroxylmethyl) furfural, comprising the steps:

mixing biomass with an aqueous portion, a water immiscible portion, and an acid to form a mixture; and heating the mixture to a temperature of from about 50° C. to about 280° C. to provide levulinic acid or 5-(hydroxymethyl)furfural in the water immiscible portion.

1a. The process of paragraph 1, wherein the mixture is heated from about 80° C. to about 250° C.

1b. The process of paragraph 1, wherein the mixture is heated from about 100° C. to about 220° C.

1c. The process of paragraph 1, wherein the mixture is heated from about 50° C. to about 100° C.

1d. The process of paragraph 1, wherein the mixture is heated from about 50° C. to about 90° C.

1e. The process of paragraph 1, wherein the mixture is heated from about 50° C. to about 80° C.

1f The process of paragraph 1, wherein the mixture is heated from about 60° C. to about 80° C.

2. The process of paragraph 1, wherein the mixture is heated to reflux conditions.

3. The process of any of paragraphs 1 through 2, wherein the mixture is heated under pressure, wherein the pressure range is from about 10 psi to about 1000 psi.

3a. The process of paragraph 3, wherein the pressure range of from about 30 to about 500 psi.

3b. The process of paragraph 3, wherein the pressure range if from about 50 to about 200 psi.

4. The process of any of paragraphs 1 through 3b, further comprising the step of mixing the mixture.

5. The process of any of paragraphs 1 through 4, further comprising the step of cooling the mixture after the mixture is heated.

6. The process of any of paragraphs 1 through 5, further comprising the step of separating the water immiscible portion containing the levulinic acid or the 5-(hydroxymethyl) furfural from the aqueous portion.

7. The process of paragraph 6, further comprising the step of removing the water immiscible portion from the levulinic acid or 5-(hydroxymethyl) furfural.

8. The process of paragraph 7, wherein the water immiscible portion is removed by distillation to provide a reaction material containing the levulinic acid or 5-(hydroxymethyl) furfural.

9. The process of paragraph 8, further comprising the step of treating the reaction material with a solid sorbent.

9a. The process of paragraph 9, wherein the solid sorbent is/are pieces of wood, an ion exchange resin, optionally with a solvent, molecular sieves, optionally with a solvent, or activated carbon, optionally with a solvent.

10. The process of either paragraph 9 or 9a, further comprising the steps of removing the levulinic acid or 5-(hydroxymethyl) furfural from the solid sorbent by heat, pressure, or by rinsing with water, aqueous base or a polar solvent.

11. The process of any of paragraphs 1 through 10, wherein the biomass comprises sludges from paper manufacturing process; agricultural residues; bagasse pity; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water; post-fermentation liquor; furfural still residues; and combinations thereof, a C5 sugar, a C6 sugar, a lignocelluloses, cellulose, starch, a polysaccharide, a disaccharide, a monosaccharide or mixtures thereof.

12. The process of any of paragraph 11, wherein the biomass is fructose, sucrose, glucose or a mixture thereof.

13. The process of any of paragraphs 1 through 12, wherein the acid is a mineral acid.

14. The process of paragraph 13, wherein the mineral acid is sulfuric acid, phosphoric acid, hydrochloric acid or mixtures thereof.

15. The process of either paragraph 13 or 14, wherein the concentration of mineral acid is from about 1 percent to about 75 percent by weight of the mixture.

16. The process of paragraph 15, wherein the concentration of the mineral acid is from about 5 percent to about 60 percent by weight of the mixture, more particularly from about 20 weight percent to about 50 weight percent.

17. The process of any of paragraphs 1 through 12, wherein the acid is an organic sulfonic acid.

18. The process of paragraph 17, wherein the organic acid is para-toluene sulfonic acid, naphthalene sulfonic acid, camphor sulfonic acid or n-dodecylbenzene sulfonic acid.

19. The process of any of paragraphs 1 through 18, further comprising adding a phase transfer catalyst to the mixture.

20. The process of paragraph 19, wherein the phase transfer catalyst is an ammonium salt, a heterocyclic ammonium salt or a phosphonium salt.

21. The process of any of paragraphs 1 through 20, wherein the water immiscible portion is methyl isobutyl ketone, ethyl levulinate, butyl levulinate, cyclohexanone, toluene, methyl-THF, methyl-tertiary butyl ether, methyl isoamyl ketone, hexane, cyclohexane, chloro-benzene, methylene chloride, dichloroethane, orthodichlorobenzene, diisobutyl ketone, 2,6-dimethyl cyclohexanone, tetrahydrofuran or mixtures thereof.

22. The process of any of paragraphs 1 through 21, wherein the process is conducted in a continuously-stirred tank reactor (CSTR) or a plug-flow reactor (PFR).

23. The process of paragraph 22, wherein the CSTR process is conducted wherein a ratio of about 2:1 to about 5:1 water to biomass is added to the reactor over a period of 1 hour and an equivalent weight amount is removed during the same time period.

24. The process of paragraph 23, wherein the biomass is fructose.

25. The process of either paragraphs 23 or 24, wherein a ratio of about 10:1 to about 15:1 water to mineral acid is added to the reactor over a period of 1 hour and an equivalent weight amount is removed during the same time period.

26. The process of paragraph 22, wherein the CSTR process is conducted wherein a ratio of about 2:1 to about 5:1 water to biomass is added to the reactor over a period of time t and an equivalent weight amount is removed during the same time period t.

27. The process of paragraph 26, wherein the biomass is fructose.

28. The process of either paragraphs 26 or 27, wherein a ratio of about 10:1 to about 15:1 water to mineral acid is added to the reactor over the period of time t and an equivalent weight amount is removed during the same time period.

The process of any of paragraphs 1 through 21, wherein the process is conducted in a continuous addition batch reactor.

30. The process of paragraph 29, wherein the continuous addition batch process is conducted wherein a ratio of about 2:1 to about 5:1 water to biomass is added to the reactor over a period of 1 hour.

31. The process of paragraph 30, wherein the biomass is fructose.

32. The process of either paragraphs 30 or 31, wherein a ratio of about 10:1 to about 15:1 water to mineral acid is added to the reactor over a period of 1 hour.

33. The process of paragraph 29, wherein the continuous addition batch process is conducted wherein a ratio of about 2:1 to about 5:1 water to biomass is added to the reactor over a period of time t.

34. The process of paragraph 33, wherein the biomass is fructose.

35. The process of either paragraphs 33 or 34, wherein a ratio of about 10:1 to about 15:1 water to mineral acid is added to the reactor over the period of time t.

The following paragraphs provide for additional aspects of the present invention. In one embodiment, in a first paragraph (1), the present invention provides a process to prepare levulinic acid or formic acid, comprising the steps:

mixing up to 50 weight percent of a fructose containing material comprising fructan, fructooligosaccharide, inulin, fructose, fructose-glucose blended corn syrup, sucrose or mixtures thereof, up to 75 weight percent of an acid catalyst and at least 20 weight percent water to equal 100 weight percent to form a mixture; and heating the mixture to a temperature of from about 50° C. to about 280° C. to provide levulinic acid or formic acid.

1a. The process of paragraph 1, wherein the mixture is heated from about 80° C. to about 250° C.

1b. The process of paragraph 1, wherein the mixture is heated from about 100° C. to about 220° C.

1c. The process of paragraph 1, wherein the mixture is heated from about 50° C. to about 100° C.

1d. The process of paragraph 1, wherein the mixture is heated from about 50° C. to about 90° C.

1e. The process of paragraph 1, wherein the mixture is heated from about 50° C. to about 80° C.

1f. The process of paragraph 1, wherein the mixture is heated from about 60° C. to about 80° C.

2. The process of any of paragraphs 1 through 1f, wherein the mixture is heated under pressure, wherein the pressure range is from about 10 psi to about 1000 psi.

2a. The process of paragraph 2, wherein the pressure range of from about 30 to about 500 psi.

2b. The process of paragraph 2, wherein the pressure range if from about 50 to about 200 psi.

3. The process of any of paragraphs 1 through 2b, wherein the acid is present from about 10 weight percent to about 40 weight percent.

3a. The process of any of paragraphs 1 through 3, wherein the acid is present from about 20 weight percent to about 30 weight percent.

4. The process of any of paragraphs 1 through 3a, wherein the mixture is heated for 60 minutes or less.

5. The process of paragraph 4, wherein the mixture is heated for 30 minutes or less.

6. The process of any of paragraphs 1 through 5, further comprising the step of mixing the mixture.

7. The process of any of paragraphs 1 through 6, further comprising the step of cooling the mixture after the mixture is heated.

8. The process of any of paragraphs 1 through 7, further comprising the step of isolating the levulinic acid or the formic acid from solid humin by-product.

9. The process of paragraph 8, further comprising the step of treating the humin by-product with a solvent to provide a filtrate.

10. The process of paragraph 9, wherein the solvent is water, methylisobutyl ketone, methyl-THF, cyclohexanone, acetonitrile, acetone, methanol, ethanol, butanol, MTBE or mixtures thereof.

11. The process of either paragraph 9 or 10, wherein the isolated levulinic acid or formic acid and the filtrate are combined to provide a final filtrate.

12. The process of paragraph 11, wherein the molar yield of levulinic acid is from about 50% to about 90%.

13. The process of paragraph 11, wherein the molar yield of formic acid is from about 50% to about 90%.

14. The process of any of paragraphs 1 through 13, further comprising the step of treating the mixture with a solid sorbent.

14a. The process of paragraph 14, wherein the solid sorbent is/are pieces of wood, an ion exchange resin, optionally with a solvent, molecular sieves, optionally with a solvent, or activated carbon, optionally with a solvent.

15. The process of either paragraph 14 or 14a, further comprising the steps of removing the levulinic acid or 5-(hydroxymethyl) furfural from the solid sorbent by heat, pressure, or by rinsing with water, aqueous base or a polar solvent.

16. The process of any of paragraphs 1 through 15, wherein the acid is a mineral acid.

17. The process of paragraph 16, wherein the mineral acid is sulfuric acid, phosphoric acid, hydrochloric acid or mixtures thereof.

18. The process of any of paragraphs 1 through 17, wherein the process is conducted in a continuously-stirred tank reactor (CSTR) or a plug-flow reactor (PFR).

19. The process of paragraph 18, wherein the CSTR process is conducted wherein a ratio of about 2:1 to about 5:1 water to fructose or sugar is added to the reactor over a period of 1 hour and an equivalent weight amount is removed during the same time period.

20. The process of paragraph 19, wherein a ratio of about 10:1 to about 15:1 water to mineral acid is added to the reactor over a period of 1 hour and an equivalent weight amount is removed during the same time period.

21. The process of paragraph 18, wherein the CSTR process is conducted wherein a ratio of about 2:1 to about 5:1 water to fructose or sugar is added to the reactor over a period of time t and an equivalent weight amount is removed during the same time period.

22. The process of paragraph 21, wherein a ratio of about 10:1 to about 15:1 water to mineral acid is added to the reactor over the period of time t and an equivalent weight amount is removed during the same time period.

The following paragraphs provide for additional aspects of the present invention. In one embodiment, in a first paragraph (1), the present invention provides a process to prepare levulinic acid or formic acid, comprising the steps:

mixing a biomass material with an acid catalyst or supercritical water to form a first mixture, wherein the biomass is converted to provide glucose;

treating the glucose with an isomerization catalyst or a base catalyst to form a second mixture, wherein the glucose is converted into fructose;

mixing the fructose containing mixture with an acid and water form a third mixture; and heating the third mixture to a temperature of from about 50° C. to about 280° C. to provide levulinic acid or formic acid.

1a. The process of paragraph 1, wherein the biomass comprises sludges from paper manufacturing process; agricultural residues; bagasse pity; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar, corn syrup; hemp; waste paper, wastepaper fibers; sawdust; wood; residue from agriculture or forestry; organic components of municipal and industrial wastes; waste plant materials from hard wood or beech bark; fiberboard industry waste water; post-fermentation liquor, furfural still residues; and combinations thereof, a C5 sugar, a C6 sugar, a lignocelluloses, cellulose, starch, a polysaccharide, a disaccharide, a monosaccharide or mixtures thereof.

1b. The process of either paragraph 1 or 1a, wherein the mixture is heated from about 80° C. to about 250° C.

1c. The process of either paragraph 1 or 1a, wherein the mixture is heated from about 100° C. to about 220° C.

1d. The process of either paragraph 1 or 1a, wherein the mixture is heated from about 50° C. to about 100° C.

1e. The process of either paragraph 1 or 1a, wherein the mixture is heated from about 50° C. to about 90° C.

1f. The process of either paragraph 1 or 1a, wherein the mixture is heated from about 50° C. to about 80° C.

1g. The process of either paragraph 1 or 1a, wherein the mixture is heated from about 60° C. to about 80° C.

2. The process of any of paragraphs 1 through 1g, wherein the mixture is heated under pressure, wherein the pressure range is from about 10 psi to about 1000 psi.

2a. The process of paragraph 2, wherein the pressure range of from about 30 to about 500 psi.

2b. The process of paragraph 2, wherein the pressure range if from about 50 to about 200 psi.

3. The process of any of paragraphs 1 through 2b, wherein the biomass converting catalyst is hydrochloric acid, sulfuric acid, triflic acid, trifluoroacetic acid or mixtures thereof.

4. The process of any of paragraphs 1 through 3, wherein the glucose isomerization catalyst is glucoisomerase.

5. The process of any of paragraphs 1 through 4, wherein the glucose converting base catalyst is a basic alkali or alkaline earth metal hydroxide or carbonate.

6. The process of any of paragraphs 1 through 5, wherein the third mixture contains about 0.1 to about 30 weight percent of a fructose containing material.

7. The process of paragraph 6, wherein the fructose containing material comprises fructan, fructooligosaccharide, inulin, fructose, fructose corn syrup or mixtures thereof.

8. The process of paragraph 7, wherein the fructose containing material is present from about 1 to about 99 weight percent.

9. The process of paragraph 1, wherein the third mixture contains up to 50 weight percent of the acid.

10. The process of paragraph 9, wherein the acid is present from about 2 to about 40 weight percent.

11. The process of paragraph 10, wherein the acid is a mineral acid.

12. The process of paragraph 11, wherein the mineral acid is sulfuric acid, phosphoric acid, hydrochloric acid or mixtures thereof.

13. The process of any of paragraphs 1 through 12, wherein the third mixture is heated for 60 minutes or less.

14. The process of paragraph 13, wherein the mixture is heated for 30 minutes or less.

15. The process of any of paragraphs 1 through 14, further comprising the step of mixing one or more of the mixtures.

16. The process of any of paragraphs 1 through 15, further comprising the step of cooling the third mixture after the mixture is heated.

17. The process of any of paragraphs 1 through 16, further comprising the step of isolating the levulinic acid or the formic acid from solid humin by-product.

18. The process of paragraph 17, further comprising the step of treating the humin by-product with a solvent to provide a filtrate.

19. The process of paragraph 18, wherein the solvent is water, methylisobutyl ketone, methyl-THF, cyclohexanone, acetonitrile, acetone, methanol, ethanol, butanol. MTBE or mixtures thereof.

20. The process of either paragraph 18 or 19, wherein the isolated levulinic acid or formic acid and the filtrate are combined to provide a final filtrate.

21. The process of paragraph 20, wherein the molar yield of levulinic acid is from about 50% to about 90%.

22. The process of paragraph 20, wherein the molar yield of formic acid is from about 50% to about 90%.

23. The process of any of paragraphs 1 through 22, wherein the process is conducted in a continuously-stirred tank reactor (CSTR) or a plug-flow reactor (PFR).

24. The process of paragraph 23, wherein the CSTR process is conducted wherein a ratio of about 2:1 to about 5:1 water to biomass is added to the reactor over a period of 1 hour and an equivalent weight amount is removed during the same time period.

25. The process of paragraph 24, wherein the biomass comprises fructose.

26. The process of either paragraphs 24 or 25, wherein a ratio of about 10:1 to about 15:1 water to mineral acid is added to the reactor over a period of 1 hour and an equivalent weight amount is removed during the same time period.

27. The process of paragraph 23, wherein the CSTR process is conducted wherein a ratio of about 2:1 to about 5:1 water to biomass is added to the reactor over a period of time t and an equivalent weight amount is removed during the same time period.

28. The process of paragraph 27, wherein the biomass comprises fructose.

29. The process of either paragraphs 26 or 27, wherein a ratio of about 10:1 to about 15:1 water to mineral acid is added to the reactor over a period of time t and an equivalent weight amount is removed during the same time period.

30. The process of any of paragraphs 1 through 29, further comprising the step of treating the final filtrate with a solid sorbent.

31. The process of paragraph 30, wherein the solid sorbent is/are pieces of wood, an ion exchange resin, optionally with a solvent, molecular sieves, optionally with a solvent, or activated carbon, optionally with a solvent.

32. The process of either paragraph 30 or 31, further comprising the steps of removing the levulinic acid or formic acid from the solid sorbent by heat, pressure, or by rinsing with water, aqueous base or a polar solvent.

The following paragraphs provide for additional aspects of the present invention. In one embodiment, in a first paragraph (1), the present invention provides a continuous process for producing levulinic acid from a biomass using a first reactor having an entrance and an exit and a second reactor having an entrance and an exit said process comprising, continuously supplying a sample containing said biomass to said first reactor through said entrance to said first reactor.

hydrolyzing said biomass in said first reactor at between 210° C. and 230° C. for between 10 seconds and 100 seconds in the presence of a water immiscible liquid and mineral acid comprising between 1% and 5% by weight of said sample to produce hydroxymethylfurfural and other reaction intermediates, continuously removing an intermediate sample containing said hydroxymethylfurfural and other reaction intermediates from said first reactor through said exit of said first reactor in such a manner that substantially no axial mixing occurs in said first reactor, continuously supplying the intermediate sample that has been removed from said first reactor to said second reactor through said entrance to said second reactor, hydrolyzing said hydroxymethylfurfural and other reaction intermediates in said intermediate sample in said second reactor at between 195° C. and 215° C. for between 15 minutes and 30 minutes in the presence of, optionally a water immiscible liquid, and a mineral acid comprising between 3% and 7.5% by weight of said intermediate sample to produce levulinic acid, and continuously removing levulinic acid from said second reactor through said exit of said second reactor, wherein the yield of levulinic acid removed from said second reactor comprises at least 60% of the theoretical yield.

2. The process of paragraph 1, wherein the biomass comprises sludges from paper manufacturing process; agricultural residues; bagasse pity; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water; post-fermentation liquor, furfural still residues; and combinations thereof, a C5 sugar, a C6 sugar, a lignocelluloses, cellulose, starch, a polysaccharide, a disaccharide, a monosaccharide or mixtures thereof.

3. The process of any of paragraphs 1 through 20, wherein the water immiscible liquid is methyl isobutyl ketone, ethyl levulinate, butyl levulinate, cyclohexanone, toluene, methyl-THF, methyl-tertiary butyl ether, methyl isoamyl ketone, hexane, cyclohexane, chloro-benzene, methylene chloride, dichloroethane, ortho-dichlorobenzene, diisobutyl ketone, 2,6-dimethyl cyclohexanone, tetrahydrofuran or mixtures thereof.

4. The process of any of paragraphs 1 through 3, further comprising the step of treating the hydroxymethylfurfural from the first reactor or the levulinic acid from the second reactor with a solid sorbent.

5. The process of paragraph 4, wherein the solid sorbent is/are pieces of wood, an ion exchange resin, optionally with a solvent, molecular sieves, optionally with a solvent, or activated carbon, optionally with a solvent.

6. The process of either paragraph 4 or 5, further comprising the steps of removing the levulinic acid or formic acid from the solid sorbent by heat, pressure, or by rinsing with water, aqueous base or a polar solvent.

The following paragraphs provide for still an additional aspect of the present invention. In one embodiment, in a first paragraph (1), the present invention provides a process for producing formic acid from a carbohydrate-containing material, the process comprising: introducing a carbohydrate-containing material to a first reactor; hydrolyzing the carbohydrate-containing material in the first reactor in the presence of a water immiscible liquid and a mineral acid for a first time period at a first temperature and a first pressure effective to form an intermediate hydrolysate comprising one or more sugars; transferring the intermediate hydrolysate from the first reactor to a second reactor, hydrolyzing the intermediate hydrolysate in the second reactor for a second time period at a second temperature less than 195 degrees C. and a second pressure effective to form a hydrolysate product comprising formic acid; and isolating the formic acid in a vapor from the hydrolysate product.

The following paragraphs provide for still additional aspects of the present invention. In one embodiment, in a first paragraph (1), the present invention provides a process to prepare levulinic acid or formic acid, comprising the steps:

mixing a biomass material with an acid catalyst or supercritical water to form a first mixture, wherein the biomass is converted to provide glucose;

treating the glucose with an isomerization catalyst or a base catalyst to form a second mixture, wherein the glucose is converted into fructose;

mixing the fructose containing mixture with an acid and water form a third mixture;

heating the third mixture at a temperature of from about 50° C. to about 280° C.;

cooling the third mixture; and treating the third mixture with an water immiscible solvent to form an aqueous layer and a water immiscible layer, providing levulinic acid or formic acid in the water immiscible layer.

1a. The process of paragraph 1, wherein the biomass comprises sludges from paper manufacturing process; agricultural residues; bagasse pity; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water; post-fermentation liquor, furfural still residues; and combinations thereof, a C5 sugar, a C6 sugar, a lignocelluloses, cellulose, starch, a polysaccharide, a disaccharide, a monosaccharide or mixtures thereof.

1b. The process of either paragraph 1 or 1a, wherein the mixture is heated from about 80° C. to about 250° C.

1c. The process of either paragraph 1 or 1a, wherein the mixture is heated from about 100° C. to about 220° C.

1d. The process of either paragraph 1 or 1a, wherein the mixture is heated from about 50° C. to about 100° C.

1e. The process of either paragraph 1 or 1a, wherein the mixture is heated from about 50° C. to about 90° C.

1f. The process of either paragraph 1 or 1a, wherein the mixture is heated from about 50° C. to about 80° C.

1g. The process of either paragraph 1 or 1a, wherein the mixture is heated from about 60° C. to about 80° C.

2. The process of any of paragraphs 1 through 1g, wherein the mixture is heated under pressure, wherein the pressure range is from about 10 psi to about 1000 psi.

2a. The process of paragraph 2, wherein the pressure range of from about 30 to about 500 psi.

2b. The process of paragraph 2, wherein the pressure range if from about 50 to about 200 psi.

3. The process of any of paragraphs 1 through 2b, wherein the biomass converting catalyst is hydrochloric acid, sulfuric acid, triflic acid, trifluoroacetic acid or mixtures thereof.

4. The process of paragraph 1, wherein glucose converting isomerization catalyst is glucoisomerase.

5. The process of paragraph 1, wherein the glucose converting catalyst is a basic alkali or alkaline earth metal hydroxide or carbonate.

6. The process of paragraph 1, wherein the third mixture contains about 0.1 weight percent to about 30 weight percent of a fructose containing material.

7. The process of paragraph 6, wherein the fructose containing material comprises fructan, fructooligosaccharide, inulin, fructose, fructose corn syrup or mixtures thereof.

8. The process of paragraph 7, wherein the fructose containing material is present from about 1 to about 99 weight percent.

9. The process of paragraph 1, wherein the third mixture contains up to 50 weight percent of the acid.

10. The process of paragraph 9, wherein the acid is present from about 2 to about 40 weight percent.

11. The process of paragraph 10, wherein the acid is a mineral acid.

12. The process of paragraph 11, wherein the mineral acid is sulfuric acid, phosphoric acid, hydrochloric acid or mixtures thereof.

13. The process of any of paragraphs 1 through 12, wherein the third mixture is heated for 60 minutes or less.

14. The process of paragraph 13, wherein the mixture is heated for 30 minutes or less.

15. The process of any of paragraphs 1 through 14, further comprising the step of mixing one or more of the mixtures.

16. The process of any of paragraphs 1 through 15, further comprising the step of isolating the levulinic acid or the formic acid from solid humin by-product.

17. The process of paragraph 16, wherein the isolation step is filtration.

18. The process of paragraph 17, further comprising the step of treating the humin by-product with a solvent to provide a filtrate.

19. The process of paragraph 18, wherein the solvent is water, methylisobutyl ketone, methyl-THF, cyclohexanone, acetonitrile, acetone, methanol, ethanol, butanol, MTBE or mixtures thereof.

20. The process of either paragraph 18 or 19, wherein the isolated levulinic acid or formic acid and the filtrate are combined to provide a final filtrate.

21. The process of paragraph 20, wherein the molar yield of levulinic acid is from about 50% to about 90%.

22. The process of paragraph 20, wherein the molar yield of formic acid is from about 50% to about 90%.

23. The process of any of paragraph 1 through 22, wherein the water immiscible solvent is methyl isobutyl ketone, ethyl levulinate, butyl levulinate, cyclohexanone, toluene, methyl-THF, methyl-tertiary butyl ether, methyl isoamyl ketone, hexane, cyclohexane, chloro-benzene, methylene chloride, dichloroethane, orthodichlorobenzene, diisobutyl ketone, 2,6-dimethyl cyclohexanone, tetrahydrofuran or mixtures thereof.

24. The process of any of paragraphs 1 through 23, wherein the aqueous layer or final filtrate and water immiscible layers are separated.

25. The method of any of paragraphs 1 through 24, further comprising the step of concentrating the water immiscible layer containing the levulinic acid or formic acid to provide a concentrate.

26. The method of paragraph 25, wherein the concentration step is conducted under reduced pressure.

27. The method of paragraph 26, wherein the concentration step is conducted at an elevated temperature.

28. The method of paragraphs 25 or 26, wherein the water immiscible layer is agitated.

29. The method of any of paragraphs 26 through 28, wherein the reduced pressure is from about 10 to about 700 torr.

30. The method of any of paragraphs 26 through 29, wherein the water immiscible layer was heated to about 20 to about 140° C.

35. The process of any of paragraphs 25 through 30, further comprising the step of subjecting the concentrate to wipe film evaporation to provide purified levulinic acid.

36. The process of paragraph 35, wherein the levulinic acid had a purity of at least 95%.

37. The process of any of paragraphs 25 through 30, further comprising the step of treating the concentrate with a solid sorbent.

38. The process of paragraph 37, wherein the solid sorbent is/are pieces of wood, an ion exchange resin, optionally with a solvent, molecular sieves, optionally with a solvent, or activated carbon, optionally with a solvent.

39. The process of either paragraph 37 or 38, further comprising the steps of removing the levulinic acid or formic acid from the solid sorbent by heat, pressure, or by rinsing with water, aqueous base or a polar solvent.

40. The process of any of paragraphs 1 through 24, wherein the process is conducted in a continuously-stirred tank reactor (CSTR) or a plug-flow reactor (PFR).

41. The process of paragraph 40, wherein the CSTR process is conducted wherein a ratio of about 2:1 to about 5:1 water to biomass is added to the reactor over a period of 1 hour and an equivalent weight amount is removed during the same time period.

42. The process of paragraph 41, wherein the biomass is fructose.

43. The process of either paragraphs 41 or 42, wherein a ratio of about 10:1 to about 15:1 water to mineral acid is added to the reactor over a period of 1 hour and an equivalent weight amount is removed during the same time period.

44. The process of paragraph 40, wherein the CSTR process is conducted wherein a ratio of about 2:1 to about 5:1 water to biomass is added to the reactor over a period of time t and an equivalent weight amount is removed during the same time period.

45. The process of paragraph 44, wherein the biomass is fructose.

46. The process of either paragraphs 44 or 46, wherein a ratio of about 10:1 to about 15:1 water to mineral acid is added to the reactor over a period of time t and an equivalent weight amount is removed during the same time period.

The following paragraphs provide for still further additional aspects of the present invention. In one embodiment, in a first paragraph (1), the present invention provides a process to prepare levulinic acid or formic acid, comprising the steps:

mixing sucrose, glucose, fructose containing material or mixtures thereof with and water to form a mixture, heating the mixture at a temperature of from about 50° C. to about 280° C.;

cooling the mixture to provide an aqueous portion and solids:

isolating the aqueous portion from the solids; and treating the aqueous portion with an water immiscible solvent to form an aqueous layer and a water immiscible layer, providing levulinic acid or formic acid in the water immiscible layer.

1a. The process of paragraph 1, wherein the mixture is heated from about 80° C. to about 250° C.

1b. The process of paragraph 1, wherein the mixture is heated from about 100° C. to about 220° C.

1c. The process of paragraph 1, wherein the mixture is heated from about 50° C. to 100° C.

1d. The process of paragraph 1, wherein the mixture is heated from about 50° C. to 90° C.

1e. The process of paragraph 1, wherein the mixture is heated from about 50° C. to 80° C.

1f. The process of paragraph 1, wherein the mixture is heated from about 60° C. to 80° C.

1g. The process of paragraph 1 through 1f, wherein the mixture is heated under pressure, wherein the pressure range is from about 10 psi to about 1000 psi.

1h. The process of paragraph 1g, wherein the pressure range of from about 30 to about 500 psi.

1i. The process of paragraph 1g, wherein the pressure range if from about 50 to 200 psi.

2. The process of paragraph 1, wherein the mixture contains from about 1 to about 50 weight percent of sucrose, glucose, fructose containing material or mixtures thereof.

3. The process of paragraph 2, wherein the fructose containing material comprises fructan, fructooligosaccharide, inulin, fructose, fructose corn syrup or mixtures thereof.

4. The process of paragraph 2, wherein the sucrose, glucose, fructose containing material or mixtures thereof is present from about 5 to about 30 weight percent.

5. The process of paragraph 1, wherein the acid is present from about 1 to about 50 weight percent.

6. The process of any of paragraphs 1 through 5, wherein the mixture is heated for 60 minutes or less.

7. The process of paragraph 6, wherein the mixture is heated for 30 minutes or less.

8. The process of any of paragraphs 1 through 7, further comprising the step of mixing the mixture.

9. The process of any of paragraphs 1 through 8, wherein the isolation step is filtration.

10. The process of paragraph 9, further comprising the step of treating the solids with a solvent to provide a filtrate.

11. The process of paragraph 10, wherein the solvent is water.

12. The process of either paragraph 10 or 11, wherein the aqueous portion and the filtrate are combined to provide a final filtrate.

13. The process of any of paragraph 1 through 12, wherein the water immiscible solvent is methyl isobutyl ketone, ethyl levulinate, butyl levulinate, cyclohexanone, toluene, methyl-THF, methyl-tertiary butyl ether, methyl isoamyl ketone, hexane, cyclohexane, chloro-benzene, methylene chloride, dichloroethane, ortho-dichlorobenzene, diisobutyl ketone, 2,6-dimethyl cyclohexanone, tetrahydrofuran or mixtures thereof.

14. The process of any of paragraphs 1 through 13, wherein the filtrate and water immiscible layers are separated.

15. The method of any of paragraphs 1 through 14, further comprising the step of concentrating the water immiscible layer containing the levulinic acid or formic acid to provide a concentrate.

16. The method of paragraph 15, wherein the concentration step is conducted under reduced pressure.

17. The method of paragraph 16, wherein the concentration step is conducted at an elevated temperature.

18. The method of paragraphs 15 or 16, wherein the water immiscible layer is agitated.

19. The method of any of paragraphs 16 through 18, wherein the reduced pressure is from about 10 to about 700 torr.

20. The method of any of paragraphs 16 through 19, wherein the water immiscible layer was heated to about 20 to about 140° C.

21. The process of any of paragraphs 15 through 20, further comprising the step of subjecting the concentrate to wipe film evaporation to provide purified levulinic acid.

22. The process of paragraph 21, wherein the levulinic acid had a purity of at least 95%.

23. The process of any of paragraphs 15 through 20, further comprising the step of treating the concentrate with a solid sorbent.

24. The process of paragraph 23, wherein the solid sorbent is/are pieces of wood, an ion exchange resin, optionally with a solvent, molecular sieves, optionally with a solvent, or activated carbon, optionally with a solvent.

25. The process of either paragraph 23 or 24, further comprising the steps of removing the levulinic acid or formic acid from the solid sorbent by heat, pressure, or by rinsing with water, aqueous base or a polar solvent.

26. The process of any of paragraphs 1 through 15, wherein the process is a conducted in a continuously-stirred tank reactor (CSTR) or a plug-flow reactor (PFR).

27. The process of paragraph 26, wherein the CSTR process is conducted wherein a ratio of about 2:1 to about 5:1 water to sucrose, glucose, or fructose containing material is added to the reactor over a period of 1 hour and an equivalent weight amount is removed during the same time period.

28. The process of paragraph 27, wherein the biomass comprises fructose.

29. The process of either paragraphs 27 or 28, wherein a ratio of about 10:1 to about 15:1 water to mineral acid is added to the reactor over a period of 1 hour and an equivalent weight amount is removed during the same time period.

30. The process of paragraph 26, wherein the CSTR process is conducted wherein a ratio of about 2:1 to about 5:1 water to sucrose, glucose, or fructose containing material is added to the reactor over a period of time t and an equivalent weight amount is removed during the same time period.

31. The process of paragraph 30, wherein the biomass comprises fructose.

32. The process of either paragraphs 30 or 31, wherein a ratio of about 10:1 to about 15:1 water to mineral acid is added to the reactor over a period of time t and an equivalent weight amount is removed during the same time period.

The following paragraphs provide for yet still further additional aspects of the present invention. In one embodiment, in a first paragraph (1), the present invention provides a method to purify levulinic acid comprising the steps:

dissolving levulinic acid in a solvent to provide a levulinic acid solution;

contacting the levulinic acid solution with molecular sieves or a period of time:

separating the molecular sieves from the levulinic acid solution; and heating the sieves or applying reduced pressure to the sieves to release purified levulinic acid or treating the sieves with water, aqueous base, or a polar solvent to rinse the levulinic acid from the sieves.

2. The method of paragraph 1, wherein the molecular sieve size range is from about 2 angstroms to about 15 angstroms.

3. The method of either paragraph 1 or 2, wherein the weight ratio of molecular sieves to solvent is about 1:10 to 10:1.

4. The method of any of paragraphs 1 through 3, wherein the concentration of levulinic acid in the levulinic acid solution is about 1 to about 20 weight percent, more particularly from about 2 to about 15 weight percent.

5. The method of any of paragraphs 1 through 4, wherein the solvent is cyclohexanone, methyl-tetrahydrofuran, toluene or methyl isobutyl ketone.

6. The method of any of paragraphs 1 through 5, wherein the purified levulinic acid has a purity of at least 95%.

7. The method of any of paragraphs 1 through 6, wherein the color index (YI) of the purified levulinic acid has a color index of below 50 as measured by ASTM method E313.

The following paragraphs provide for further additional aspects of the present invention. In one embodiment, in a first paragraph (1), the present invention provides a method to purify levulinic acid comprising the steps:

dissolving from about 10 to about 50 weight percent levulinic acid in a solvent to provide a levulinic acid solution;

cooling the levulinic acid solution to about less than 15° C. to induce precipitation of levulinic acid; and collecting the precipitated levulinic acid.

2. The method of paragraph 1, wherein the solvent is methyl isobutyl ketone, cyclohexanone, or toluene.

3. The method of either of paragraphs 1 or 2, wherein the precipitated levulinic acid has a purity of at least 95%.

4. The method of any of paragraphs 1 through 3, wherein the precipitated levulinic acid has a color index of less than 50 as measured by ASTM method E313.

The following paragraphs provide for further additional aspects of the present invention. In one embodiment, in a first paragraph (1), the present invention provides a method to purify levulinic acid comprising the steps:

dissolving up to about 50 weight percent of levulinic acid in a solvent with the proviso that solvent is not water to provide a levulinic acid solution; and adding an aqueous base solution to the levulinic acid solution to provide a levulinic acid salt precipitate.

2. The method of paragraph 1, wherein the base is an alkali metal or an alkaline earth metal hydroxide or carbonate.

3. The method of paragraphs 1 or 2, wherein the weight percentage of base is from about 0.5 to about 5 equivalents based on the moles of levulinic acid.

4. The method of any of paragraphs 1 through 3, wherein the solvent is methyl isobutyl ketone, cyclohexanone, toluene or mixtures thereof.

5. The method of any of paragraphs 1 through 4, further comprising the step of isolating the levulinic acid salt precipitate.

The following paragraphs also provide for further additional aspects of the present invention. In one embodiment, in a first paragraph (1), the present invention provides a method to prepare levulinic acid comprising the steps of:

combining levulinic acid, a biomass material, a mineral acid and less than 10 weight percent water to form a mixture, wherein the components equal 100 weight percent;

heating the mixture to a range of about 50° C. to about 280° C. to provide a hydrolyzed mixture;

cooling the hydrolyzed mixture;

isolating solids from liquids; and cooling the liquids to form precipitated levulinic acid.

1a. The process of paragraph 1, wherein the biomass comprises sludges from paper manufacturing process; agricultural residues; bagasse pity; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water; post-fermentation liquor; furfural still residues; and combinations thereof, a C5 sugar, a C6 sugar, a lignocelluloses, cellulose, starch, a polysaccharide, a disaccharide, a monosaccharide or mixtures thereof.

1b. The process of either paragraph 1 or 1a, wherein the mixture is heated from about 80° C. to about 250° C.

1c. The process of either paragraph 1 or 1a, wherein the mixture is heated from about 100° C. to about 220° C.

1d. The process of either paragraph 1 or 1a, wherein the mixture is heated from about 50° C. to about 100° C.

1e. The process of either paragraph 1 or 1a, wherein the mixture is heated from about 50° C. to about 90° C.

1f. The process of either paragraph 1 or 1a, wherein the mixture is heated from about 50° C. to about 80° C.

1g. The process of either paragraph 1 or 1a, wherein the mixture is heated from about 60° C. to about 80° C.

1h. The process of any of paragraphs 1 through 1g. wherein the mixture is heated under pressure, wherein the pressure range is from about 10 psi to about 1000 psi.

1i. The process of paragraph h, wherein the pressure range of from about 30 to about 500 psi.

1j. The process of paragraph 1i, wherein the pressure range of from about 50 to about 200 psi.

2. The method of any of paragraphs 1 through 1f, wherein the weight percentage of levulinic acid is from about 50 to about 90.

3. The method of any of paragraphs 1 or 2, wherein the weight percentage of biomass is from about 5 to about 30.

4. The method of any of paragraphs 1 through 3, wherein the mineral acid weight percentage is from about 1 to about 20.

5. The method of any of paragraphs 1 through 4, wherein the weight percentage of water is less than 8 percent.

6. The method of any of paragraphs 1 through 5, wherein the hydrolyzed mixture is cooled to range of below 20° C.

7. The method of any of paragraphs 1 through 6, wherein the liquids are cooled to range of from about 60° C. to about 10° C.

8. The method of any of paragraphs 1 through 7, wherein the biomass comprises a C5 sugar, sucrose, a C6 sugar, a lignocelluloses, cellulose, starch, a polysaccharide, a disaccharide, a monosaccharide, a hard wood a soft wood, or mixtures thereof.

9. The process of any of paragraph 8, wherein the biomass is sucrose, fructose or glucose.

10. The process of any of paragraphs 1 through 9, wherein the mineral acid is sulfuric acid, phosphoric acid, hydrochloric acid or mixtures thereof.

The following paragraphs also provide for further additional aspects of the present invention. In one embodiment, in a first paragraph (1), the present invention provides a method to prepare levulinic acid comprising the steps of:

combining levulinic acid, a mineral acid and less than 10 weight percent water to form a mixture, wherein the components equal 100 weight percent;

mixing the mixture for a period of time at a temperature range of from about 50° C. to about 280° C.;

cooling the mixture to a temperature range of from about −30° C. to about 5° C.; and isolating solids from liquids to provide levulinic acid.

2. The method of paragraph 1, wherein the weight percentage of levulinic acid is from about 70 percent to about 95 percent.

3. The method of either paragraphs 1 or 2, wherein the mineral acid weight percentage is from about 5 percent to about 10 percent.

4. The method of any of paragraphs 1 through 3, wherein the weight percentage of water from about 3 percent to about 8 percent.

5. The method of any of paragraphs 1 through 4, wherein the hydrolyzed mixture is cooled to range of from about −25° C. to about 10° C.

7. The method of any of paragraphs 1 through 5, wherein the mixture is cooled to range of from about −20° C. to about 5° C.

8. The process of any of paragraphs 1 through 7, wherein the mineral acid is sulfuric acid, phosphoric acid, hydrochloric acid or mixtures thereof.

The following paragraphs also provide for further additional aspects of the present invention. In one embodiment, in a first paragraph (1), the present invention provides a method to prepare levulinic acid or formic acid, comprising the steps; mixing up to 30 weight percent of a fructose containing material comprising fructan, fructooligosaccharide, inulin, fructose, fructose-glucose blended corn syrup, sucrose or mixtures thereof, up to 75 weight percent of an acid catalyst and at least 20 weight percent water to equal 100 weight percent to form a mixture; and heating the mixture to a temperature of from about 50° C. to about 100° C. to provide levulinic acid or formic acid.

2. The process of paragraph 1, wherein the mixture comprises 40-75% of an acid catalyst.

3. The process of paragraph 1, wherein the mixture comprises 50-70% of an acid catalyst.

4. The process of any of paragraphs 1-3, wherein the acid catalyst is sulfuric acid.

5. The process of any of paragraphs 1-4 wherein the reaction is run for less than 480 minutes.

6. The process of any of paragraphs 1-4 wherein the reaction is run for less than 360 minutes.

7. The process of any of paragraphs 1-4 wherein the reaction is run for less than 120 minutes.

8. The process of any of paragraphs 1-4 wherein the reaction is run for less than 60 minutes.

9. The process of any of paragraphs 1-4 wherein the reaction is run for less than less than 30 minutes.

10. The process of any of paragraphs 1-4 wherein the reaction is run for less than less than 15 minutes.

11. The process of any of paragraphs 1-10 wherein the reaction is run at a temperature from about 50° C. to about 90° C.

12. The process of any of paragraphs 1-10 wherein the reaction is run at a temperature from about 50° C. to about 80° C.

13. The process of any of paragraphs 1-10 wherein the reaction is run at a temperature from about 60° C. to about 80° C.

The following paragraph provide for additional aspects of the present invention. In one embodiment, in a first paragraph (1), the present invention provides a process to prepare levulinic acid or formic acid, comprising the steps:

mixing up to 50 weight percent of a fructose containing material comprising fructan, fructooligosaccharide, inulin, fructose, fructose-glucose blended corn syrup, sucrose or mixtures thereof, up to 75 weight percent of an acid catalyst and at least 20 weight percent water to equal 100 weight percent to form a mixture; and heating the mixture to a temperature of from about 50° C. to about 280° C. to provide levulinic acid or formic acid.

The following paragraphs also provide for further still additional aspects of the present invention. In one embodiment, in a first paragraph (0.1), applicable to any of the above noted paragraphs (noted as [0051] through [0427], the process is conducted in a continuous addition batch reactor.

2. The process of paragraph 1, wherein the continuous addition batch process is conducted wherein a ratio of about 2:1 to about 5:1 water to biomass is added to the reactor over a period of 1 hour.

3. The process of paragraph 2, wherein the biomass is fructose.

4. The process of either paragraphs 1 or 2, wherein a ratio of about 10:1 to about 15:1 water to mineral acid is added to the reactor over a period of 1 hour.

5. The process of paragraph 1, wherein the continuous addition batch process is conducted wherein a ratio of about 2:1 to about 5:1 water to biomass is added to the reactor over a period of time t.

6. The process of paragraph 5, wherein the biomass is fructose.

7. The process of either paragraphs 4 or 5, wherein a ratio of about 10:1 to about 15:1 water to mineral acid is added to the reactor over the period of time t.

The following paragraphs also provide for further still additional aspects of the present invention. In one embodiment, in a first paragraph (1), applicable to any of the above noted paragraphs (noted as [0051] through [0427], the biomass is added over a period of from about 0.1 to about 40 hours, more specifically, 0.25 to 20 hours, more specifically, 0.5 to 10 hours, and even more specifically, 0.75 to 5 hours.

The following paragraphs also provide for further still additional aspects of the present invention. In one embodiment, in a first paragraph (1), applicable to any of the above noted paragraphs (noted as [0051] through [0427], the formic acid and levulinic acid are extracted together using a first extraction solvent, or are extracted separately, using a first and a second extraction solvent. In another embodiment, the formic acid is removed from the reaction mixture by distillation, steam stripping or extraction prior to extracting the levulinic acid.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

In one aspect, the invention is directed to a process to make crystallizable levulinic acid ("LA") from sugar solutions.

Hydrolysis of a 1-3 Molar solution of sucrose, glucose, fructose, or blends of the aforementioned, specifically fructose and sucrose, occurs in a batch or continuous reactor, specifically a continuous reactor. In one embodiment the method includes the following steps following hydrolysis of a 1-3 Molar solution of sucrose, glucose, fructose, or blends of the aforementioned:
  (a) Filtration of solids from hydrolysate mixture.
  (b) Water or extraction solvent wash of solids (optional).
  (c) Extraction of LA and formic acid from aqueous hydrolysate into an extraction solvent.
  (d) Removal of extraction solvent by distillation.
  (e) Thin-film evaporation of LA.
  (f) Crystallization of LA.
  (g) recovery of formic acid.

The process allows fast reaction time, easy to handle char byproduct, good yields, no neutralization step (optional), efficient extraction and distillation to afford a crystallizable LA product.

A few processes are known to make LA from sugar, but little is known on how to remove the LA and formic acid from the reactor and purify it from the hydrolysate. The disclosed process produces approximately 97% purity LA that crystallizes.

Unless otherwise noted, the concentration of sulfuric acid used is 96-98%.

Example 1

Into a 1 L hastelloy parr reactor 135.12 g fructose (94% purity, 0.75 mol), 500 mL DI water, and 38.17 g sulfuric acid were charged. The reactor was sealed and the reaction mixture was heated up to a temperature of 150° C. while stirring at 52 RPM. Once the reaction mixture reached a temperature of 150° C., the mixture was held at that temperature for 1 hour. After the 1 hour reaction time the heat was turned off and the heating mantle was lowered and the reactor was cooled using an ice water bath. Once the reactor was cooled it was dismantled and the reaction mixture was filtered through a 0.45 pm filter using vacuum filtration in order to remove the char from the liquid. The liquid was analyzed by HPLC and found to contain 9.9 wt % levulinic acid. The liquid is referred to as "hydrolysate".

Into a 1 L separatory funnel 300.10 g hydrolysate and 300.07 g Methyl isobutyl ketone (MIBK) were charged. The separatory funnel was shaken in order to mix everything together and then the mixture was allowed to phase separate. The bottom aqueous layer was drained out of the bottom of the separatory funnel and collected in a beaker. The top layer was poured out of the top of the separatory funnel and into a 2-neck 1 L round bottom flask. The bottom layer was then placed back into the separatory funnel and another 300.36 g MIBK were used for the second extraction. The mixture was shaken and allowed to phase separate again. The bottom layer was drained and discarded. The top layer was poured out of the top of the separatory funnel into the 2-neck 1 L round bottom flask containing the previous MIBK-extract.

The 2-neck 1 L round bottom flask (RBF) was situated into a heating mantle and equipped with a magnetic stir bar, thermocouple, vigreux column, short path condenser, and a 1 L collection flask. The mixture was stirred at 600 rpm and the vacuum was kept between 15-30 torr. Over the course of the distillation the temperature of the pot was slowly increased until a maximum temperature of 70° C. was reached. The MIBK was distilled away from the mixture, the crude levulinic acid (LA) mixture left in the pot was a very dark brown color.

The crude LA was purified by wipe film evaporation (WLE). The crude LA was placed into a reservoir and degassed. The heater was turned on and set to 70° C. and the vacuum was set to 0.25-0.3 Torr. Once a temperature of 70° C. was reached the blades were turned on and the crude LA was slowly fed into the WFE. Dark black material was collected in the heavy fraction and light yellow material was collected in the light fraction. Once all of the material had passed through the WFE, the vacuum, heat and blades were shut off and the light fraction. LA, was analyzed by GC-FID. The GC-FID results showed that the LA was 95% pure. A small sample of this LA was put into a scintillation vial and cooled to 5° C., and it crystallized. This light yellow LA was redistilled by WFE a second time. This time the temperature was set to 65° C. and the vacuum was still at 0.25-0.3 Torr. Again, the dark material was collected in the heavy fraction and a faint red material was collected in the light fraction. Once all of the LA had gone through the WFE it was shut down and the light fraction was analyzed by GC-FID. The GC-FID results of the LA after going through the WFE a second time showed that the LA was 97% pure. This LA was cooled to 5° C. The entire sample crystallized, indicating good quality levulinic acid.

Use of fructose as a feedstock for the production of levulinic acid is known in the art. HCl has been used as a catalyst to make levulinic acid. HCl is a very corrosive catalyst and creates the possibility of generating chlorinated organic compounds, so this is not a good option.

Zeolites have been used as catalysts for the production of LA. The zeolites are typically used in high concentrations, and presumably would foul due to the formation of solid humin substances during the conversion of fructose to LA. This catalyst cost would not be economically viable for the production of LA. Also, U.S. Pat. No. 7,317,116 describes the use of fructose or high fructose corn syrup to make levulinic acid using heterogeneous cation exchange resin catalysts and polyethylene glycol solvents. The use of heterogeneous catalysts to produce LA from biomass or sugars would also have the problem of fouling by the formation of soluble polymeric and insoluble polymeric substances, known as humins. Additionally, the time of the reaction required to convert fructose to LA as described in U.S. Pat. No. 7,317,116 was 4-18h. which would be much too long for an industrial continuous process.

Herein, a new method is described for the conversion of fructose or fructose-containing feedstocks into levulinic acid and formic acid. The process allows up to 30 wt % feedstock and from about 4 to about 60 wt % mineral acid, such as sulfuric acid, to be used in an aqueous reaction mixture, while producing >50 mol % LA in less than 60 minutes of reaction time, preferably less than 30 minutes of reaction time, and more preferably less than 20 minutes of reaction time.

In another embodiment, this process can be backwards integrated into a cellulose or ligno-cellulose producer or bio-refinery.

In another embodiment, the use of washing the produced humin substances with a solvent or water, or a combination of both, is an added beneficial method to produce a higher mass recovery of LA and formic acid.

Example 2

1 Mol/L D-Fructose (15 mL) was prepared by diluting 2.44 g of crystalline D-Fructose (93.5% purity, 6.5% moisture, Aldrich) up to 15.0 mL with DI water. The 15.0 mL was transferred to a 3 oz. empty high pressure, high temperature reaction vessel, and concentrated sulfuric acid (407 µL) was added. The reaction vessel was capped using a Teflon sleeve, an o-ring, rubber washer and a stainless steel plug. The reactor was securely closed with stainless steel couplings. The reaction vessel was placed into a 180° C. hot oil bath to reach an internal temperature of around 160° C. After a specified reaction time, the reaction vessel was then removed from the hot oil and placed in a room temperature water bath for 1 minute to begin cooling. Following the room temperature water bath, the reactor was placed in an ice water bath to quench the reaction. Once the reactor vessel had cooled, it was opened, and the contents were filtered, weighed, and then analyzed by HPLC. The humin solids that formed during the reaction were extracted with DI water and the LA in the "wash" sample was recovered and analyzed by HPLC and weighed separately to obtain the yield. The two yields of LA were added together to obtain the final mol % yield of LA relative to the initial moles of fructose charged in the feed. The final results are displayed in Table I.

Examples 3-4

The procedure outlined in Example 2 was repeated, except that the feed concentration of fructose and acid catalyst was varied, as well as, the temperature of the reaction.

acid (FA). The process involves glucose conversion to fructose (without crystallization of the fructose), the fructose then feeds into a solution with water and sulfuric acid catalyst to form LA and FA in less than 60 minutes of reaction time. This pre-treatment of the glucose or sugar feedstock may be enzymatically catalyzed or chemically catalyzed to afford>70% conversion of the glucose or "sugar" to fructose. Methods of glucose to fructose conversion are generally known in the art.

The glucose and "sugar" polymer mixture may be obtained by the enzymatic degradation of starch, maltose, or the like, or alternatively, by the hydrolytic or catalytic degradation of cellulose to glucose. The glucose obtained from these reactions may also be obtained from a ligno-cellulosic feedstock.

Also, this process can be attached to a bio-refinery, which depolymerizes cellulose or ligno-cellulose into glucose for ethanol production, but instead of producing 100% ethanol, some of the process streams containing crude or purified glucose are subsequently converted into fructose and then to LA and FA.

In a typical biomass process, biomass is converted into levulinic acid (LA) and formic acid (FA) by a strong-acid catalyst in a dilute, aqueous system. The LA and FA are then first extracted into a solvent phase to remove the LA and FA from the aqueous phase containing the strong-acid catalyst. The solvent may be, for example, methyl-isobutyl ketone (MIBK), methyl isoamyl ketone (MIAK), cyclohexanone, o, m, and para-cresol, substituted phenols, for example, 2-sec butyl phenol, C4-C18 alcohols, such as n-pentanol, isoamyl alcohol, n-heptanol, 2-ethyl hexanol, n-octanol, 1-nonanol, cyclohexanol, methylene chloride, 1,2-dibutoxy-ethylene glycol, acetophenone, isophorone, o-methoxy-phenol, methyl-tetrahydrofuran, tri-alkylphosphine oxides (C4-C18) and ortho-dichlorobenzene and mixtures thereof. Once the LA and FA is extracted into the solvent, the usual way of purification of the LA and FA is by removing the solvent through energy-intensive distillation followed by distillation of the LA, another energy intensive step which may lead to side-products and yield losses.

One novel way of purifying the LA from the extractive solvent is to remove the LA by the use of an adsorbents, like molecular sieves, basic alumina, silica gel, or the like.

TABLE I

| Example | Wt % Fructose in Feed | Wt % Sulfuric acid in Feed | Max. Temperature | Time (min) | Fructose Conversion (%) | Molar Yield of LA (%) | Molar Yield of FA (%) | Wt % LA Yield Improvement Washing Solid Humins |
|---|---|---|---|---|---|---|---|---|
| 2 | 13.6 | 4.7 | 143° C. | 50 | 99 | 47 | 66 | 16 |
| 3 | 18.9 | 5.5 | 156° C. | 30 | 100 | 57 | 72 | 12 |
| 4 | 23.5 | 5.5 | 160.1° C. | 30 | 100 | 54 | 71 | 15 |

As can be seen from Table I, fructose can be hydrolyzed completely in less than 60 minutes of reaction time to afford up to 63 mol % yield and 79 mol % yield of formic acid (FA). Also, extracting LA from the solid humin material resulted in >10 wt % yield improvement of LA in all of the examples.

Utilizing High Fructose Corn syrup, inulin, oligomeric fructan polymers, and the like are also be useful in this invention.

Another process of this invention involves the pretreatment of glucose to obtain>70% conversion to fructose directly before the fructose is hydrolyzed to LA and formic Example 5

A 10.22 gram solution of levulinic acid (4.8 wt %) in cyclohexanone was weighed in a 125 mL Erlenmeyer Flask, 10.05 of 3A Molecular Sieves was added to the flask. The flask was sealed with parafilm to prevent evaporation of the solvent. The mixture was aged overnight (>12h) at room temperature. A sample of the liquid was withdrawn from the flask and analyzed by HPLC. The amount of LA in the final liquid was found to be 3.7 wt %, indicating that approximately 0.11 g of LA had been adsorbed by the molecular sieves.

TABLE 2

| Example | Size of Molecular Sieves | g of Mol Sieves | g of solvent | Solvent Type | % LA in solvent (Initial) | % LA removed (Final) |
|---|---|---|---|---|---|---|
| 5 | 3A | 10.05 | 10.22 | cyclohexanone | 4.8 | 23 |
| 6 | 4A | 10 | 10.01 | cyclohexanone | 4.8 | 10 |
| 7 | 5A | 10 | 10.06 | cyclohexanone | 4.8 | 21 |
| 8 | 3A | 10.03 | 10.03 | methyl-THF | 4.4 | 11 |
| 9 | 4A | 10.06 | 10.04 | methyl-THF | 4.4 | 9 |
| 10 | 5A | 10.1 | 10.02 | methyl-THF | 4.4 | 14 |
| 11 | 3A | 10.02 | 10.04 | toluene | 5.2 | 42 |
| 12 | 4A | 10.02 | 10.11 | toluene | 5.2 | 37 |
| 13 | 5A | 10.04 | 10.13 | toluene | 5.2 | 40 |
| 14 | 3A | 10.02 | 10.03 | MIBK | 4.0 | 35 |
| 15 | 4A | 10.01 | 10.06 | MIBK | 4.0 | 17.5 |
| 16 | 5A | 10.09 | 10.02 | MIBK | 4.0 | 32.5 |

Examples 6-16 were repeated as described in Example 5, except that different solvents and different sizes of molecular sieves were used according to Table 2.

As can be seen from the data, LA may be removed from typical hydrolysate extraction solvents by molecular sieves. The 3A and 5A size molecular sieves seem to provide a more selective removal of levulinic acid in virtually all solvent systems. This provides a unique and alternative pathway to remove levulinic acid in a biomass-type hydrolysis system involving an extraction solvent.

In other examples, basic alumina, silica gel, activated carbon, biomass char, zeolites, activated clays, anion exchange resins, and ion exchange resins, may be used to adsorb levulinic acid from an extraction solvents.

In a typical biomass process, biomass is converted into levulinic acid (LA) and LA by a strong-acid catalyst in a dilute, aqueous system. However, instead of using water as the solvent, one embodiment, it would be beneficial if the solvent was actually one of the products, for example, levulinic acid or formic acid.

This portion of the invention describes how the hydrolysis of biomass may be conducted in formic or levulinic acid. If the hydrolysis of biomass is conducted in levulinic acid, then once the reaction is finished, filtered to remove char, and cooled to room temperature, levulinic acid may form a crystalline solid. This solid form of levulinic acid offers a unique advantage of purification of the LA from biomass.

In a typical hydrolysis of biomass, 2-20 wt % sulfuric acid is used as the catalyst, and the amount of water used in the hydrolysis is between 60-95 wt %. In this invention, the majority of the water is removed and replaced with levulinic acid, which enables crystallization of the final LA product by cooling the hydrolysate solution comprising water, LA, and sulfuric acid.

Experimental—Crystallization of LA in a Hydrolysis Mixture

Example 17

A mixture containing 10 wt % sulfuric acid, 87 wt % levulinic acid, and 3 wt % water was made in a 20 mL scintillation vial. The vial was cooled in a refrigerator at 5° C. overnight. After 24h, crystals had formed in the vial, indicating that the levulinic acid had crystallized out of solution.

Examples 18-23 were repeated as described in Example 17, except that different amounts of LA, sulfuric acid, and water were used in the experiments.

TABLE 3

| Example | Sulfuric Acid (wt %) | LA (wt %) | DI Water (wt %) | Crystals present after cooling (4d) |
|---|---|---|---|---|
| 17 | 10 | 87 | 3 | yes |
| 18 | 7.5 | 87 | 5.5 | yes |
| 19 | 5 | 87 | 8 | no |
| 20 | 5 | 92 | 3 | yes |
| 21 | 10 | 77 | 13 | no |
| 22 | 10 | 67 | 23 | no |

As can be seen from the data, LA may be crystallized out from cooling a solution of LA, water, and a strong acid catalyst. This could be very advantageous for enabling a process to produce and purify LA from the strong acid catalyzed degradation of furfuryl alcohol, sugars, or lignocellulosic biomass.

Example 23

The reaction is carried out by adding 640 g of levulinic acid and 50 g of sulfuric acid (96+%. Aldrich), 100 g fructose (crystalline, 93+% purity, Aldrich), and 6 g of DI water to a 1 L Hastelloy autoclave equipped with a magnetically couple overhead stirrer. The contents are purged with nitrogen and heated to 160° C. for 1 h. The contents are cooled to 40° C. and filtered. Then, the contents are cooled below 10° C. and allowed to crystallize. The crystalline product is filtered and subsequently purified.

Example 24

The reaction is carried out by adding 640 g of levulinic acid and 50 g of sulfuric acid (96+%, Aldrich), 100 g furfuryl alcohol (crystalline, 93+% purity. Aldrich), and 25 g of DI water to a 1 L Hastelloy autoclave equipped with a magnetically couple overhead stirrer. The contents are purged with nitrogen and heated to 160° C. for 1 h. The contents are cooled to 40° C. and filtered. Then, the contents are cooled below 10° C. and allowed to crystallize. The crystalline product is filtered and subsequently purified.

Example 25

The reaction is carried out by adding 640 g of levulinic acid and 50 g of sulfuric acid (96+%, Aldrich), 100 g sucrose (crystalline, 97+% purity, Aldrich), and 8 g of DI water to a 1 L Hastelloy autoclave equipped with a magnetically couple overhead stirrer. The contents are purged with nitrogen and heated to 160° C. for 1.5h. The contents are cooled to 40° C. and filtered. Then, the contents are cooled below 10° C. and allowed to crystallize. The crystalline product is filtered and subsequently purified.

Example 26

The reaction is carried out by adding 640 g of levulinic acid and 50 g of sulfuric acid (96+%, Aldrich), 100 g glucose (crystalline, 98+% purity, Aldrich), and 6 g of DI water to a 1 L Hastelloy autoclave equipped with a magnetically couple overhead stirrer. The contents are purged with nitrogen and heated to 160° C. for 2.5h. The contents are cooled to 40° C. and filtered. Then, the contents are cooled below 10° C. and allowed to crystallize. The crystalline product is filtered and subsequently purified.

Example 27

The reaction is carried out by adding 640 g of levulinic acid and 50 g of sulfuric acid (96+%, Aldrich), 100 g soft wood (pine, Home Depot), and 20 g of DI water to a 1 L Hastelloy autoclave equipped with a magnetically couple overhead stirrer. The contents are purged with nitrogen and heated to 160° C. for 1 h. The contents are cooled to 40° C. and filtered. Then, the contents are cooled below 10° C. and allowed to crystallize. The crystalline product is filtered and subsequently purified.

In a typical biomass process, biomass is converted into levulinic acid (LA) and FA by a strong-acid catalyst in a dilute, aqueous system. The levulinic acid and optionally the formic acid, is then first extracted into a solvent phase to remove the levulinic acid and/or the formic acid from the aqueous phase containing the strong-acid catalyst. The solvent may be, for example, methyl-isobutyl ketone (MIBK), methyl isoamyl ketone (MIAK), cyclohexanone, o, m, and para-cresol, substituted phenols, for example, 2-sec butyl phenol, C4-C18 alcohols, such as n-pentanol, isoamyl alcohol, n-heptanol, 2-ethyl hexanol, n-octanol, 1-nonanol, cyclohexanol, methylene chloride, 1,2-dibutoxy-ethylene glycol, acetophenone, isophorone, o-methoxy-phenol, methyl-tetrahydrofuran, tri-alkylphosphine oxides (C4-C18) and ortho-dichlorobenzene and mixtures thereof or the like, more specifically, methyl isoamyl ketone (MIAK), o, m, and para-cresol, phenol, isoamyl alcohol, n-hexanol, n-heptanol, 2-ethyl hexanol, o-methoxy-phenol, 2-4 dimethyl phenol, methyl isobutyl carbinol, and mixtures thereof or the like, and even more specifically, o, m, and para-cresol, isoamyl alcohol, neopentyl alcohol, methyl isobutyl carbinol, and mixtures thereof or the like. Once the LA is extracted into the solvent, the usual way of purification of the LA is by removing the solvent through energy-intensive distillation followed by distillation of the LA, another energy intensive step which may lead to side-products and yield losses.

One novel way of purifying the LA from the extractive solvent is to distill off a portion of the solvent, then allow the LA to crystallize out of the solvent by cooling. LA is usually diluted to about 1-20 wt % in the hydrolysate prior to extraction, and after extraction, the concentration of LA in the solvent can be from 0.5-50 wt %, preferably from 1-45 wt %, and more preferably, from 2-40 wt %. The solvent may be distilled away from LA in order to concentrate the LA. The following examples describe the invention.

Example 28

A 10% solution of levulinic acid in MIBK was made in a 20 mL scintillation vial. The vial was sealed and put into a freezer at −15° C. The solution remained clear and homogenous indicating that no crystallization took place.

Examples 29-39 were repeated as described in Example 28, except that different solvents and different concentrations of LA were used according to Table 4.

TABLE 4

| Example | Solvent | LA Concentration (wt %) | Crystallization at −15° C. |
|---|---|---|---|
| 29 | MIBK | 20 | no |
| 30 | MIBK | 50 | yes |
| 31 | cyclohexanone | 10 | no |
| 32 | cyclohexanone | 20 | no |
| 33 | cyclohexanone | 50 | no |
| 34 | toluene | 10 | yes |
| 35 | toluene | 20 | yes |
| 36 | toluene | 50 | yes |
| 37 | methyl THE | 10 | no |
| 38 | methyl THE | 20 | no |
| 39 | methyl THF | 50 | no |

As can be seen from the data. LA may be crystallized out from cooling a solution of MIBK that contains>20% LA. Also. Examples 34-36 demonstrate that LA may be crystallized from a solution of toluene that is cooled.

Another way to purify levulinic acid in an extraction solvent is by adding a base, for example, sodium hydroxide to form the metal salt, which would precipitate from the extraction solvent.

Example 40

2.52 g (0.02 mol) of levulinic acid and 47.57 g methyl isobutyl ketone (MIBK) were added to a 250 mL beaker and mixed thoroughly until homogeneous. To this mixture, 1.75 g of a 50/50 wt % sodium hydroxide solution was added. As soon as the sodium hydroxide was added, a white precipitate formed. A magnetic stir bar was placed into the beaker and put onto a stir plate to stir for a few minutes. With stirring, it appeared as though more precipitate formed. The precipitate was then filtered out using vacuum filtration and a 0.45 μm filter. A small amount of the precipitate was put into a GC vial and dissolved with water and then run on the HPLC to be analyzed. The analysis showed that the sodium salt of levulinic acid was synthesized.

Example 41

A small portion of the 5% levulinic acid solution in MIBK made in Example 40 was added into a saturated solution of calcium hydroxide in water. Two liquid phases formed that were cloudy at first, and then became transparent upon stirring at room temperature in a 250 mL beaker. No precipitate had formed.

Example 42

An MIBK solution containing 4% levulinic acid, 1% formic acid, 0.05% $H_2SO_4$, and 1% water was placed into a 250 mL beaker. A 50-50 wt % solution of sodium hydroxide in water was added to neutralize the acid species. Upon addition, a gellike substance formed at the bottom of the flask. No precipitate formed.

Example 43

An MIBK solution containing 4% levulinic acid, 1% formic acid, and 0.05% $H_2SO_4$ was placed into a 250 mL beaker. A 50-50 wt % solution of sodium hydroxide in water was added to neutralize the acid species. Upon addition, white precipitate formed indicating that the sodium salt of levulinic acid had formed.

Example 44

Approximately 1% water was added to Example 16, and the precipitate turned into a gel-like substance. Thus, having less than 1% water in the entire crude mixture is advantageous for the formation of solid sodium levulinate in a typical hydrolysate solution of 4% LA in MIBK solvent.

In another aspect, the present invention is directed to methods including the use of organic or inorganic, hydrophobic co-solvents for the preparation of LA from the hydrolysis of biomass. In one embodiment, the invention includes charging a co-solvent and optionally, a co-catalyst, for the purposes of improving the overall yield of levulinic acid from biomass. The biomass may be lignocellulosic, cellulosic, starch-based, or sugar-based (monomeric, dimeric, or oligomeric sugars). The process has the advantage of simultaneously making and extracting HML and or levulinic acid from biomass.

Example 45

The reaction was carried out by adding 300 g of water and 15.02 g of sulfuric acid (96+%, Aldrich), 54.07 g fructose (crystalline, 93+% purity, Aldrich), and 300 g of methyl-THL to a 1 L three-neck flask that was equipped with a magnetic stirrer and a reflux condenser. The contents were purged with nitrogen continuously and allowed to reflux for 6h. Aliquots were removed from the flask as a function of time to measure the composition in both layers. Analysis of the reaction mixture showed formation of HML and the absence of levulinic acid.

Example 46

Example 45 is repeated except that 13 g of para-toluene sulfonic acid was added to the mixture.

Example 47

Example 45 is repeated except that methyl isobutyl ketone was used instead of methyl-THF.

Example 48

Example 47 is repeated except that 13 g of para-toluene sulfonic acid was added to the mixture.

Example 49

Example 45 is repeated except that cyclohexanone was used instead of methyl-THF.

Example 50

Example 49 is repeated except that 13 g of para-toluene sulfonic acid was added to the mixture.

Example 51

Example 46 is repeated except that toluene was used instead of methyl-THF.

Example 52

Example 51 is repeated except that 13 g of para-toluene sulfonic acid was added to the mixture.

Example 53

Example 45 is repeated except that 4-sec-butyl phenol was used instead of methyl-THF.

Example 54

Example 53 is repeated except that 13 g of para-toluene sulfonic acid was added to the mixture.

Example 55

Example 45 is repeated except that 1,2-dichloro-benzene was used instead of methyl-THF.

Example 56

Example 55 is repeated except that 13 g of para-toluene sulfonic acid was added to the mixture.

Example 57

Example 45 is repeated except that m-cresol was used instead of methyl-THF.

Example 58

Example 57 is repeated except that 13 g of para-toluene sulfonic acid was added to the mixture.

Example 59

Example 45 is repeated except that tri-octyl phosphine oxide was used instead of methyl-THF.

Example 60

Example 59 is repeated except that 13 g of para-toluene sulfonic acid was added to the mixture.

Example 61

Example 45 is repeated except that tri-butyl phosphate was used instead of methyl-THF.

Example 62

Example 61 is repeated except that 13 g of para-toluene sulfonic acid was added to the mixture.

Example 63

Example 45 is repeated except that sucrose was used instead of fructose.

Example 64

Example 45 is repeated except that 20 g of naphthalene sulfonic acid was added to the mixture.

Example 65

Example 45 is repeated except that 20 g of camphor sulfonic acid was added to the mixture.

Example 66

Example 45 is repeated except that 10 g of benzene sulfonic acid was added to the mixture.

Any of examples 45-66 could be repeated at higher pressure in a Hastelloy, Zirconium, or glass-lined steel autoclave.

Any of the examples 45-66 could be repeated using glucose, soft wood, hard wood, starch, or cellulose.

Any of the examples 45-66 could be repeated using furfuryl alcohol or hydroxymethyl furfural.

Triflic acid, hydrochloric acid, hydrobromic acid, hydroiodic acid, nitric acid, phosphoric acid, boric acid, hydrofluoric acid, perchloric acid and mixtures thereof may be used instead of sulfuric acid if desired.

Example 67

After a sufficient time of reaction, the organic solvent layer is removed from the aqueous layer by a decanter or centrifuge. Then, a certain quantity of aqueous sodium hydroxide is added to the organic mixture until a precipitate forms. The precipitate is filtered, acidified, and crystallized to afford>95% purity levulinic acid. The organic solvent is re-used in the process after distillation.

Example 68

After a sufficient time of reaction, the organic solvent layer is removed from the aqueous layer by a decanter or centrifuge. Then, the solvent is cooled down to <10° C. The precipitate is filtered and crystallized to afford>95% purity levulinic acid. The organic solvent is re-used in the process after distillation.

Continuously Stirred Tank Reactor (CSTR) Operations:

A stirred, 300 ml Parr Autoclave, of Hastelloy construction, was used to investigate a continuous process for the acid-catalyzed production of levulinic and formic acids from carbohydrate sugars. Variable feed flow rates, coupled with controlled reactor volumes, were used to obtain various residence times in the autoclave. This reaction produces insoluble by-products in addition to formic and levulinic acids. Therefore, control of product flow from the reactor was unsuccessful using standard laboratory techniques due to rapid plugging of regulators and other flow-restricting devices. This was overcome by using the pressure in the autoclave to periodically blow a controlled quantity of reactor contents out of the autoclave and into a receiver through a two-way valve connected to a dip tube of a prescribed length (depth) inside the autoclave. The depth of the dip tube controlled the reactor volume around 180 ml. Continuously feeding reactants into the autoclave at 3.0 ml/minute and rapidly pulsing the two-way valve full-open and full-closed every 6.6 minutes removed approximately 20 g of sample, giving a residence time in the reactor of approximately 60 minutes. After liquid is removed down to the control volume, some gas is allowed to also escape, thereby "blowing" the lines clear of liquid. The diameter of the dip tube is selected to allow removal of both the liquid and solid components of the reaction mixture without plugging the lines, ¼ Inch lines proved sufficient for this purpose. All outlet lines require insulation/heating to maintain them at the same temperature as the reactor. This prevents premature precipitation of solids from the samples which can cause plugging. Reactants are fed into the autoclave at controlled flow rates using an Eldex pump (A-120 VS).

Example 69 CSTR Run Using Corn Sweet 90

Corn Sweet 90 is a high-fructose syrup (90% fructose, 8.5% glucose, 1.5% oligomeric sugars) supplied by ADM. It contains 77% solids, 360 g of this syrup was dissolved in 1.0 liter of 0.5M sulfuric acid and used as feed to the reactor. The autoclave was filled with 200 ml of distilled water and heated to 160° C. Internal pressure reached approximately 80-85 psig. After reaching reaction temperature, volume control was initiated by pulsing the valve and removing approximately 20 g of water. The pressure drops approximately 5-8 psig during sampling. Continuous feed was then initiated at 3 ml/minute with sampling occurring every 6.6 minutes. The weight of the samples through the run averaged approximately 20 g. The samples were dark reddish-brown in appearance and a small amount of solids precipitated out of solution as the samples cooled. Analysis of a sample taken 3 hours after initiation of Corn Sweet feed was analyzed using Liquid Chromatography (Agilent HPLC; Restek Ultra C18 Column-15 cm; 98% 2.5 pH Phosphate Buffer/2% acetonitrile; 0.5 ml/minute Eluent flow at room temperature; UV/RI detector). The sample contained 4.7% formic acid, 9.6% levulinic acid and 0.12% hydroxymethylfurfural (HMF). The low concentration of HMF is an excellent indicator of reaction completion. When the reaction was terminated, the autoclave was opened and 27.49 g of black solids were removed.

CSTR Runs Using Sucrose and Sucrose/NORIT Activated Carbon:

Example 70

An attempt was made to execute a continuous run using 1.M sucrose in 0.5M sulfuric acid at 160° C. This reaction with sucrose proved difficult to execute. Outlet sample lines plugged quickly and insufficient time occurred to achieve steady state in a continuous mode. Sucrose feed was terminated and the reaction was allowed to run to completion (1 hour) in batch mode. After the end of the run, the reactor was cooled and opened to find it full of solids. The solids adhered strongly to all the stainless steel internals inside the reactor (agitator, thermo well, dip tubes but not to the Hastelloy surfaces of the reactor body.) It appeared that the solids were nucleating and then growing on all the stainless steel surfaces of the reactor internals.

Example 71

A second run was initiated under the same conditions as those described in Example 75 except 5 weight % of NORIT Activated Carbon (PAC-200; BA#M-1620) was added to the autoclave to begin with. This was an attempt to give the solids something else on which to nucleate and adhere. A one hour batch run was completed and sampled using the two-way blow-down valve. This time, in contrast to the "NORIT-free" run, the sample was easily removed from the reactor. As the sample cooled, no separate solids were observed coming out of solution. The NORIT that exited from the reactor in the sample settled to the bottom of the sample receiver and it appeared that the solids that usually precipitate from solution upon cooling were adsorbed on the NORIT. When the autoclave was cooled and opened, the amount of solids usually found adhering to all the reactor internals were markedly reduced. It, again, appeared that the NORIT had allowed the reaction solids to adsorb/adhere to the activated carbon. This will clearly improve the operability of the reaction, particularly when using sugars that are more prone to form solids in this reaction.

Example 72

Into a three neck 250 mL round bottom flask charged 130.01 g deionized water, 23.52 g (0.13 mol) D-fructose, and 38.30 g (0.39 mol) sulfuric acid. The round bottom flask was equipped with a magnetic stir bar, thermocouple, condenser, and glass stopper. The stir plate was set to stir at a rate of 550 RPM and the fructose quickly dissolved. The mixture changed from clear and colorless to clear and a peach color. The heat was turned on and set to a temperature of 60° C. The reaction was left to react for two hours and samples were taken and analyzed by HPLC. After the two hours, the reaction was shut down.

| Time (minutes) | Temperature ° C. | % HML (HPLC) |
|---|---|---|
| 120 | 59.8 | 0.308 |

Example 73

Into a three neck 250 mL round bottom flask charged 13.08 g deionized water, 23.48 g (0.13 mol) D-fructose, and 31.23 g (0.39 mol) polyphosphoric acid. The round bottom flask was equipped with a magnetic stir bar, thermocouple, condenser, and glass stopper. The stir plate was set to stir at a rate of 550 RPM and the fructose quickly dissolved. The heat was turned on and set to a temperature of 60° C. The reaction was held at 60° C. for two hours and then the temperature was increased to 80° C. The reaction was held at 80° C. for one hour and a half and then the temperature was increased to 100° C. The reaction was held at 100° C. for two hours and then the reaction was shut down. Samples were taken throughout the entire reaction and analyzed by HPLC.

| Time (minutes) | Temperature ° C. | % HML (HPLC) |
|---|---|---|
| 410 | 99.7 | 1.747 |

Example 74

Into a three neck 250 mL round bottom flask charged 130.12 g deionized water and 23.49 g (0.13 mol) D-fructose. The round bottom flask was equipped with a magnetic stir bar, thermocouple, condenser, and glass stopper. The stir plate was set to stir at a rate of 550 RPM and the fructose quickly dissolved. Once the fructose was dissolved, 38.29 g (0.39 mol) sulfuric acid was added into the flask. The heat was turned on and set to a temperature of 80° C. The reaction was held at 80° C. for two hours and then the temperature was increased to 100° C. The reaction was held at 100° C. for four hours and fifteen minutes and then the reaction was shut down. Samples were taken throughout the entire reaction and analyzed by HPLC.

| Time (minutes) | Temperature ° C. | % HML (HPLC) | % LA (HPLC) | % LA (HPLC) |
|---|---|---|---|---|
| 385 | 100.0 | 0.007 | 6.28 | 2.607 |

Sugar Solution Preparation.
Sugar-solution I is a mixture of 90 wt % fructose, 8.5 wt % glucose, and 1.5 wt % sucrose. This mixture was dissolved in water to obtain a homogeneous solution that was 1.5 Moles of Sugar-solution I/Liter.

Example 75

1.5 Molar Sugar-solution I (715 g) and concentrated Sulfuric Acid (35.75 g) was added to a 1 L Hastelloy reactor (Parr Model 4530 Reactor). The Parr reactor was assembled and securely closed. Mixing in the reactor began and set to 100 rpm. The initial time, temperature, and pressure of the reactor was noted. An electrical heating mantel was then placed around the reactor and set to 160° C. Once the temperature inside of the reactor reached 160° C., it was held for 1 hr. After 1 hr, an ice-water bath was placed around the Parr reactor to immediately begin cooling. When the temperature of the Parr reactor was below 30° C., it was opened and the contents of the reactor were removed and analyzed by HPLC. Any solids that formed during the reaction were filtered from the reaction mixture, rinsed with water and dried in a vacuum oven to obtain the weight of total solids.
The HPLC results showed 6.7% of Levulinic acid and 2.9% Formic acid formed. The percent solids were 4.3%.

Examples 76-78

Further reactions were performed under the same procedure as Example 75. Table 5 outlines the reactions, and HPLC results.

TABLE 5

| Molar Corn Sweet 90 | Solvent | 95% Sulfuric Acid (g) | 1wt % Para-toluene Sulfuric Acid (g) | Liquid Hydroly-sate Recovered (g) | Liquid Hydrolysate Recovered + Water (g) | Top Layer (g) | Bottom Layer (g) | Dry Solids Recovered (g) | LA wt % (HPLC) |
|---|---|---|---|---|---|---|---|---|---|
| 1.0 | 50% Water 50% MIBK | 25.05 | 4.52 | 516.34 | 575.33 | 195.26 | 380.79 | 12.59 | 3.617 |
| | | | | same as above | | | | | |
| 1.0 | 50% Water 50% MIBK | 25.09 | 0 | 530.89 | 573.3 | 183.95 | 389.35 | 14.07 | 3.726 |
| | | | | same as above | | | | | 6.191 |
| 1.0 | 50% Water 50% Cyclohexanone | 25.17 | 4.87 | 578.18 | 600.18 | 325.8 | 274.38 | 0.00 | |
| | | | | same as above | | | | | |

Examples 76-79

Further reactions were performed under the same procedure as Example 75. Changes were made to the concentration of sugar, solvent mixture, and an additional acid catalyst. Also the Parr reactor was purged with nitrogen before and after the reaction. The Parr reactor mixing was also increased to 400 rpm. Table 6 outlines the reactions, conditions, and HPLC results.

the water and sulfuric acid. In one embodiment, the formic acid is removed from the hydrolysate, or reaction mixture, either before or after the solids removal step but prior to adding the extraction solvent for levulinic acid. This can be accomplished by methods known in the art, such as distillation, steam stripping or extraction. In other embodiments, the formic acid can be extracted out of the reaction mixture after the extraction of levulinic acid utilizing a different extraction solvent than that used for levulinic acid. In still

TABLE 6

| Example | Mole/L Sugar Solution II | Solvent | Mole/L Sulfuric Acid | PTSA (wt %) | Liquid Hydrolysate Recovered (g) | Liquid Hydrolysate Recovered + Water (g) | Top Layer (g) | Bottom Layer (g) | Dry Solids Recovered (g) | LA wt % (HPLC) | FA wt % (HPLC) | Furfuryl 1 wt % (HPLC) | HMF wt % (HPLC) | LA (g) | % Solids |
|---|---|---|---|---|---|---|---|---|---|---|---|---|---|---|---|
| 5 (top layer) | 1.0 | 50% Water 50% MIBK | 0.5 | 1 | 516.34 | 575.33 | 195.26 | 380.79 | 12.59 | 3.617 | 0.874 | 0 | 0.05 | 7.06 | 2.44 |
| 5 (Bottom layer) | | same as above | | | | | | | | | | | | 0.00 | NA |
| 6 (top layer) | 1.0 | 50% Water 50% MIBK | 0.5 | 0 | 530.3 | 573.3 | 183.95 | 389.35 | 14.07 | 3.726 | 0.832 | 0 | 0.057 | 6.85 | 2.65 |
| 6 (Bottom Layer) | | same as above | | | | | | | | 6.191 | 2.802 | 0 | 0.05 | 24.10 | NA |
| 7 (top layer) | 1.0 | 50% Water 50% Cyclohexanone | 0.5 | 1 | 578.18 | 600.18 | 325.8 | 274.38 | 0.00 | | | | | | 0.00 |
| 7 (Bottom Layer) | | same as above | | | | | | | | | | | | | |

The solids in Example 79 did not stick to the sides of the reactor or the stirrer blades, while in Exs, 75-78 the solids were stuck to the sides of the reactor, the bottom of the reactor and the stir shaft. They were difficult to remove.

another embodiment, the formic acid and levulinic acid are both extracted using the same extraction solvent. The water and sulfuric acid is then optionally recycled back to the reactor and the formic acid and levulinic acid are separated

| Reaction Notebook # | Example | Molar Corn Sweet 90 | Sugar Solution I (9) | Solvent | 95% Sulfuric Acid (g) | Liquid Hydrolysate Recovered (9) | water rinse (9) | Dry Solids Recovered (9) | LA wt % (HPLC) | FA wt % (HPLC) | LA (g) | % Solids |
|---|---|---|---|---|---|---|---|---|---|---|---|---|
| SMS163-60 | 79 | 1.5 | 635 | 100% Water with 5% lignin | 25.01 | 511.72 | 210.72 | 27.65 | 5.794 | 2.835 | 41.87 | 5.40 |

Figure 1B:
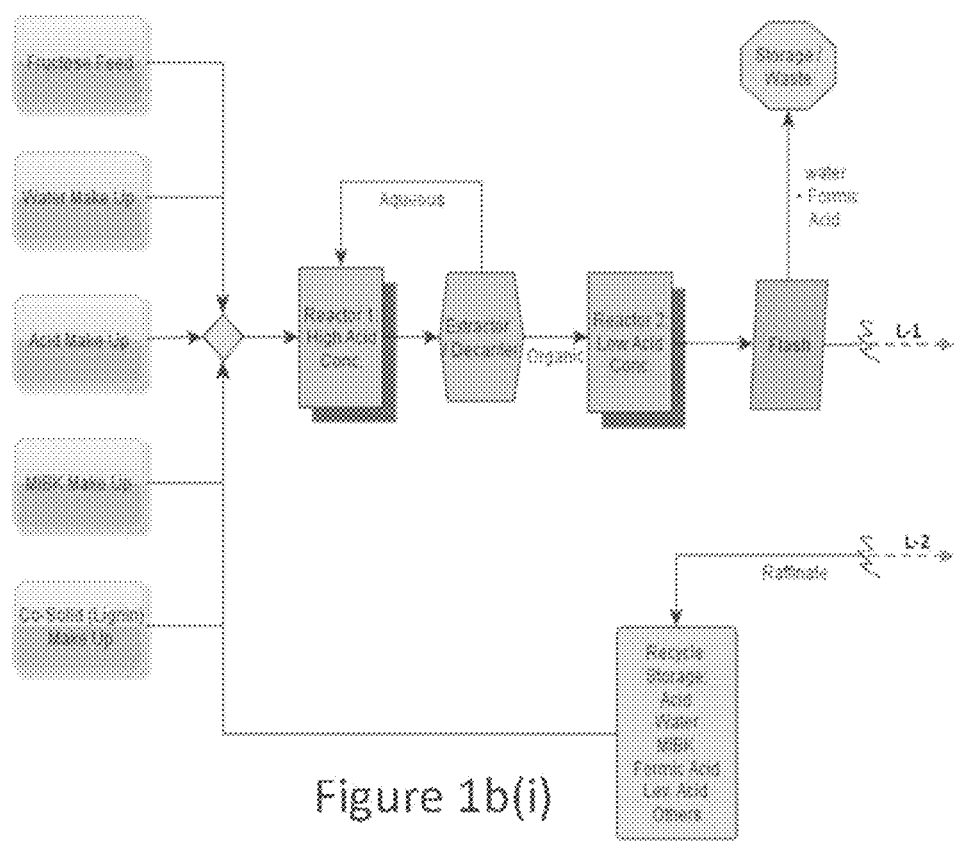
FIGS. 1b(i) and 1b(ii) are flow diagrams of another embodiment for a process to prepare and/or purify levulinic acid.
Figure 2C:
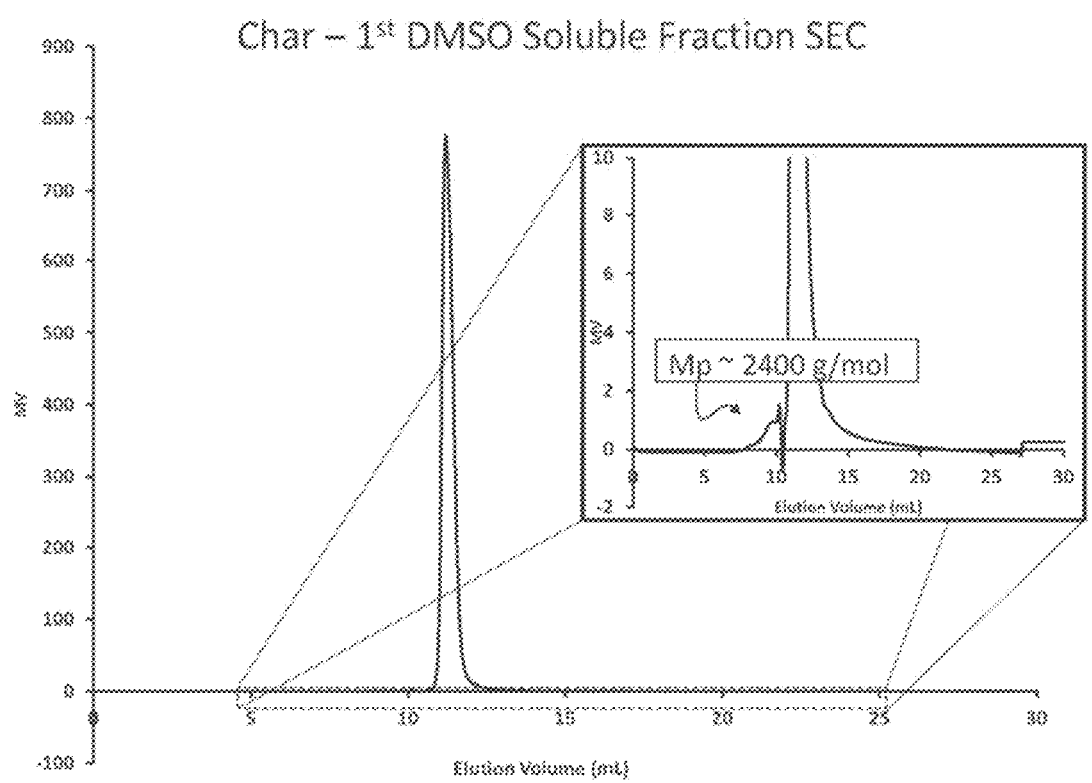
Figure 2D:
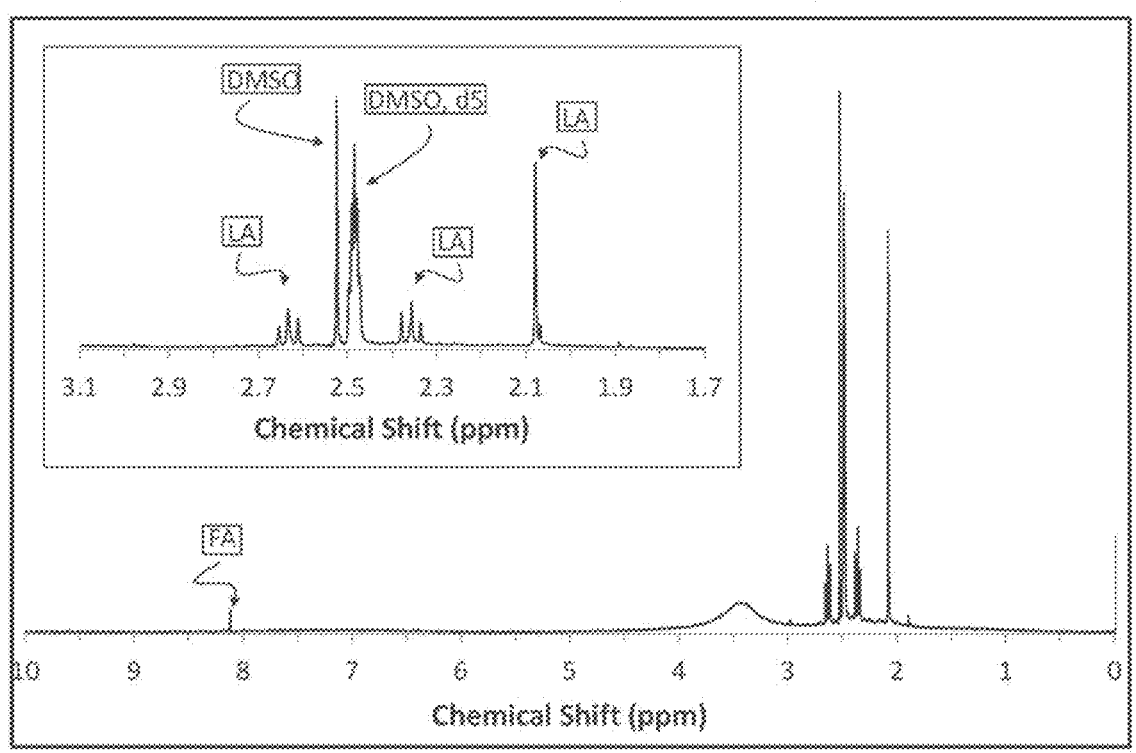
Figure 2E:
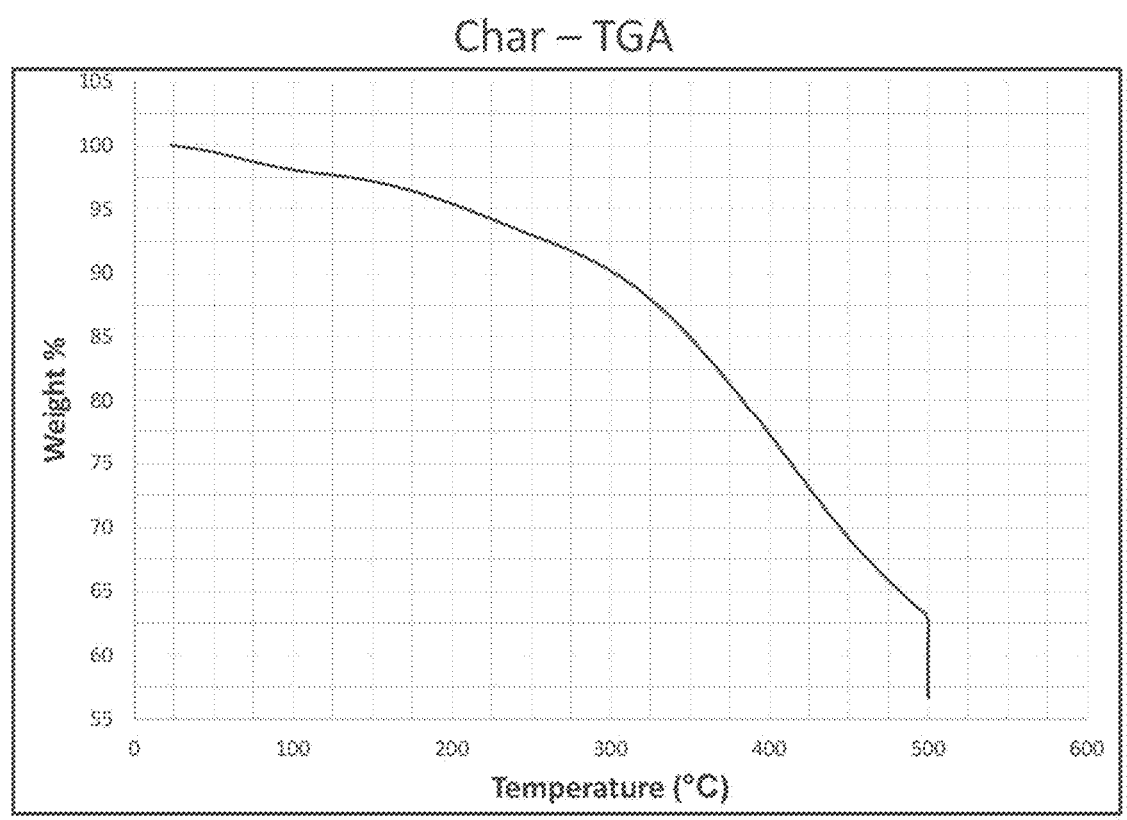

Referring now to FIGS. 1a and 1b. FIG. 1a provides a general process description for one embodiment for the production of levulinic acid. Water, mineral acid and biomass are added to a reactor under reaction conditions to convert the biomass into various products, including levulinic acid and formic acid as well as solids char. The solids are then removed from the reaction mixture. The reaction mixture is then combined with an extraction solvent, which extracts a majority of the levulinic acid and formic acid from from the extraction solvent, after which the extraction solvent can be recycled back to be re-used in the extraction step.

The reactor can be a batch reactor, a CSTR or a plug reactor. The mineral acid is sulfuric acid ($H_2SO_4$), hydrochloric acid (HCl), hydrobromic acid (HBr) or hydroiodic acid (HI), preferably sulfuric acid. The biomass comprises sludges from paper manufacturing process; agricultural residues; bagasse pity; bagasse; molasses; aqueous oak wood extracts; rice hull; oats residues; wood sugar slops; fir sawdust; naphtha; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water, post-fermentation liquor; furfural still residues; and combinations thereof, a C5 sugar, a C6 sugar, a lignocelluloses, cellulose, starch, a polysaccharide, a disaccharide, a monosaccharide or mixtures thereof. Preferably the biomass is high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof, and more preferably, the biomass comprises fructose, glucose or a combination thereof.

FIG. 1b provides a more specific process description for one embodiment for the production of levulinic acid.

Feeds

Concentration of feeds are controlled to maintain desired reaction stoichiometry. "Make-up" stream flows are controlled based on the composition and flow rate of the recycle stream.

Reactors

One, optionally two, reactors are used to convert fructose to the desired products. The reactors are optionally vented to maintain an internal pressure; the vent stream is optionally collected to recover steam and formic acid product; the vent stream can all be returned to the reactor as a reflux. If there are two reactors in series, the first reactor is optionally controlled at a different temperature and at a high concentration of acid in order to achieve desired conversion and selectivity. The first reactor would generally be controlled at a lower temperature than the second. Optionally, a process step between the two reactors may be used to separate "tar" solids and/or to preferentially extract the reaction products (away from the aqueous feed) to feed into the second reactor.

The reactors may be operated in a batch-wise (wherein the reactants are fed to the reactor and the reaction continues until the desired degree of conversion, and the products are then emptied from the reactor) or in a continuous fashion (wherein reactants are fed continuously and the products are removed continuously). In one embodiment, the reactors are run in a continuous fashion with products removed in a steady fashion or the reactants are removed in a pulsed fashion. In another embodiment, the reactors are run in a batch mode, with the biomass preferably being added to the reactor over a period of time t.

The agitation in the reactors should be adequate to prevent agglomeration of solid co-products which may be formed during the reaction. Specifically, the reactors should be designed with sufficient axial flow (from the center of the reactor to the outer diameter and back).

Flash

The reaction products may be optionally cooled in a "flash" process. The flash step rapidly cools the reaction products by maintaining a pressure low enough to evaporate a significant fraction of the products. This pressure may be at or below atmospheric pressure. The evaporated product stream may be refluxed through stages of a distillation column to minimize the loss of desired reaction products, specifically levulinic acid, and to ensure recovery of formic acid reaction products and solvent. Recovered solvent may be recycled back to reactor 1 or 2.

The "bottoms" or less volatile stream from the flash step is advanced to the solids separation stage.

Solids Separation

In the solids separation stage of the process, the solvent and desired reaction products, specifically levulinic acid and formic acid, are separated from any solids which may have formed during the reaction phase. The solids may be separated through a combination of centrifuge, filtration, and settling steps (ref Perrys Chemical Engineering Handbook, Solids Separation). The separated solids may be optionally washed with water and solvents to recover desired reaction products or solvent which may be entrained in or adsorbed to the solids. It has been found that in some embodiments, such as those reactions employing high levels of mineral acid (greater than 20%) that are reacted at lower temperatures, such as between 60-110° C., the solids may have density properties similar to the liquid hydrolysate which effectively allows the solids to be suspended in solution. In these embodiments, certain separation techniques such as centrifugation are not as effective. In these embodiments filtration utilizing filter media having a pore size less than about 20 microns has been found to effectively remove solids from the mixture. When removing solids from the system a solid "cake" is formed. It is desirable that the cake be up to 50% solids. Thus any separation technique that obtains a cake having a higher amount of solids is preferred. A certain amount of LA and mineral acid will be present in the cake and it may be desirable to wash the cake with an extraction solvent or water to recover LA.

It has also been surprisingly found that the solid particles in the high mineral acid and lower temperature embodiments are easily filtered and do not inhibit flow as the cake is formed. It is believed that the properties of the char formed under these process conditions are such that any cake remains porous enough that a small filter size (less than 20 microns) can be utilized while maintaining a high flow rate through the medium.

Referring now to FIGS. 2a through 2e, solid, black char was isolated from a fructose hydrolysate reaction mixture by filtration. The char was rinsed with water 2 times to recover additional levulinic acid and formic acid, and then, the char was dried at 50-60° C. and 30 Torr for at least 12h. The dried char was subjected to solvent extraction according to FIG. 2b. A considerable amount of material was extracted from the char. Proton NMR was used to analyze the soluble extract fraction, and it was found to contain mostly levulinic acid and formic acid. Thus, this solvent extraction method is surprisingly advantageous for further recovery of levulinic acid from the reaction mixture.

The isolated solids may be incinerated to generate power or disposed.

The liquid stream, comprising (but not limited to) water, acid, solvent, levulinic acid, formic acid, and some "soluble tars" are advanced to the extraction stage of the process.

Extraction

In the extraction stage of the process, the liquid stream is mixed with an extraction solvent stream. The preferred extraction solvent dissolves levulinic acid more effectively than the other products in the liquid stream. The preferred solvent does not dissolve significantly into the water phase. Extraction configurations are preferably multistage and continuous, as described in Perry's Chemical Engineering Handbook.

The aqueous raffinate is recycled to the reactor phase, after optional distillation or purification steps to adjust the relative concentrations of solvent, water, and acid in the raffinate.

The extract solvent phase contains levulinic acid and formic acid and is progressed to the solvent removal stage of the process.

Suitable solvents to extract LA include, for example, polar water-insoluble solvents such as MIBK, MIAK, cyclohexanone, o, m, and para-cresol, substituted phenols, for example, 2-sec butyl phenol, C4-C18 alcohols, such as n-pentanol, isoamyl alcohol, n-heptanol, 2-ethyl hexanol, n-octanol, 1-nonanol, cyclohexanol, methylene chloride, 1,2-dibutoxy-ethylene glycol, acetophenone, isophorone, o-methoxy-phenol, methyl-tetrahydrofuran, tri-alkylphosphine oxides (C4-C18) and ortho-dichlorobenzene and mixtures thereof. Such solvents are used generally at room temperature so as not to serve as potential reaction component.

Solvent Removal

Levulinic acid may be separated from the solvent phase by evaporating or distilling the solvent. Alternatively, the levulinic acid may be crystallized from the solvent phase in a crystallization process. The solvent removal process may be a combination of distillation and crystallization. The recovered solvent may be recycled to the extraction step or to the reactor step.

The resulting stream of highly concentrated levulinic acid may be advanced for further chemical derivatization or may be further purified in another distillation step such as high vacuum wipe-film-evaporation or falling film evaporation. Preferably the levulinic acid stream is kept at a low temperature throughout the solvent removal steps to inhibit the formation of angelica lactone.

Mineral Acids

Suitable acids used to convert the biomass materials described herein, to sulfuric acid, hydrochloric acid, boric acid, hydrofluoric Suitable acids used to convert the biomass including sugars, include mineral acids, such as but not limited, acid, hydrobromic acid, hydroiodic acid, nitric acid, phosphoric acid, perchloric acid and mixtures thereof.

Example 80

Into a three neck 250 mL round bottom flask 130.01 g deionized water and 23.51 g (0.13 mol, 0.72M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, 63.78 g (0.65 mol, 3.60M) sulfuric acid was added into the flask. The heat was turned on and set to a temperature of 80° C. Samples were taken as the reaction mixture was heated up and analyzed by HPLC. The reaction was held at 80° C. for four hours and then the reaction was shut down. The solids that were formed during the reaction were filtered and then dried in a vacuum oven overnight.

Once the solids were dried, they were removed from the vacuum oven and weighed.

| | |
|---|---|
| Grams of Solids | 3.44 |
| % Solids based on Fructose | 14.63 |
| % Solids based on Total Reaction Weight | 1.58 |

| | |
|---|---|
| Grams of LA | 8.28 |
| % LA based on Fructose | 35.20 |
| % LA based on Total Reaction Weight | 3.81 |

It was observed that reduced char was present at filtration as compared to reactions at higher temperatures and lower acid levels and little to no char was accumulated on the reactor components.

Example 81

Into a three neck 250 mL round bottom flask 133.12 g deionized water and 23.49 g (0.13 mol, 0.71M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, 63.75 g (0.65 mol, 3.54M) sulfuric acid was added into the flask. The heat was turned on and set to a temperature of 90° C. Samples were taken as the reaction mixture heated up and were analyzed by HPLC. The reaction was held at 90° C. for four hours and then the reaction was shut down. Samples were taken throughout the entire reaction and analyzed by HPLC. The solids that were formed during the reaction were filtered and then dried in a vacuum oven overnight.

Once the solids were dried, they were removed from the vacuum oven and weighed.

| | |
|---|---|
| Grams of Solids | 3.77 |
| % Solids based on Fructose | 16.05 |
| % Solids based on Total Reaction Weight | 1.71 |

| | |
|---|---|
| Grams of LA | 10.55 |
| % LA based on Fructose | 44.90 |
| % LA based on Total Reaction Weight | 4.79 |

It was observed that reduced char was present at filtration as compared to reactions at higher temperatures and lower acid levels and little to no char was accumulated on the reactor components.

Example 82

Into a three neck 250 mL round bottom flask 130.02 g deionized water and 23.42 g (0.13 mol, 0.72M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, 63.78 g (0.65 mol, 3.60M) sulfuric acid was added into the flask. The heat was turned on and set to a temperature of 90° C. The reaction was held at 90° C. for two hours and twenty minutes and then the reaction was shut down.

Once the solids were dried, they were removed from the vacuum oven and weighed.

| | |
|---|---|
| Grams of Solids | 5.19 |
| % Solids based on Fructose | 22.16 |
| % Solids based on Total Reaction Weight | 2.39 |

| Grams of LA | 8.25 |
|---|---|
| % LA based on Fructose | 35.22 |
| % LA based on Total Reaction Weight | 3.80 |

It was observed that reduced char was present at filtration as compared to reactions at higher temperatures and lower acid levels and little to no char was accumulated on the reactor components.

Example 83

Into a three neck 250 mL round bottom flask 65.04 g deionized water and 11.71 g (0.065 mol, 0.60M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, 63.80 g (0.65 mol, 6.04M) sulfuric acid was added into the flask slowly. Once all of the sulfuric acid was added to the reaction mixture the heat was turned on and set to a temperature of 80° C. The reaction was held at 80° C. for two hours and then the reaction was shut down. The solids that were formed during the reaction were filtered and then dried in a vacuum oven overnight.

Once the solids were dried, they were removed from the vacuum oven and weighed.

| Grams of Solids | 2.90 |
|---|---|
| % Solids based on Fructose | 24.77 |
| % Solids based on Total Reaction Weight | 2.06 |

| Grams of LA | 5.84 |
|---|---|
| % LA based on Fructose | 49.84 |
| % LA based on Total Reaction Weight | 4.15 |

It was observed that reduced char was present at filtration as compared to reactions at higher temperatures and lower acid levels and little to no char was accumulated on the reactor components.

Example 84

Into a three neck 250 mL round bottom flask 60.06 g deionized water and 10.88 g (0.06 mol, 0.61M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, an ice water bath was placed beneath the round bottom flask in order to cool the reaction mixture. The ice water bath was used to prevent the reaction mixture from getting too hot when the sulfuric acid was added. Once the reaction mixture was cold, 58.96 g (0.60 mol, 6.04M) sulfuric acid was added into the flask making sure to keep the reaction mixture below 45° C. Once all of the sulfuric acid was added to the reaction mixture the ice water bath was removed and the heating mantle was situated under the flask. The heat was turned on and set to a temperature of 90° C. The reaction was held at 90° C. for thirty minutes and then the reaction was shut down, the heating mantle was removed and an ice water bath was used to cool the mixture. The solids that were formed during the reaction were filtered and then dried in a vacuum oven overnight.

Once the solids were dried, they were removed from the vacuum oven and weighed.

| Grams of Solids | 5.49 |
|---|---|
| % Solids based on Fructose | 50.46 |
| % Solids based on Total Reaction Weight | 4.23 |

| Grams of LA | 4.08 |
|---|---|
| % LA based on Fructose | 37.51 |
| % LA based on Total Reaction Weight | 3.14 |

It was observed that reduced char was present at filtration as compared to reactions at higher temperatures and lower acid levels and little to no char was accumulated on the reactor components.

Example 85

Into a three neck 250 mL round bottom flask 60.04 g deionized water and 10.91 g (0.06 mol, 0.46M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, an ice water bath was placed beneath the round bottom flask in order to cool the reaction mixture. The ice water bath was used to prevent the reaction mixture from getting too hot when the sulfuric acid was added. Once the reaction mixture was cold, 117.73 g (1.2 mol, 9.13M) sulfuric acid was added into the flask making sure to keep the reaction mixture below 30° C. Once all of the sulfuric acid was added to the reaction mixture the ice water bath was removed and a heating mantle was situated under the flask. The heat was turned on and set to a temperature of 50° C. The reaction was held at 50° C. for thirty minutes and then the reaction was shut down, the heating mantle was removed and cooled with the ice water bath. Once the reaction mixture was cooled it was filtered in order to obtain any solids that were formed, the surprising thing was that no solids were observed. The reaction mixture was placed back into the round bottom flask and set up again in order to continue the reaction. The heat was turned on and set back to 50° C. The reaction was left to run for another 433 minutes and then was shut down. The reaction mixture was filtered again and this time solids were observed. The solids were put into a vacuum oven to dry overnight.

Once the solids were dried, they were removed from the vacuum oven and weighed.

| Grams of Solids | 8.68 |
|---|---|
| % Solids based on Fructose | 79.56 |
| % Solids based on Total Reaction Weight | 4.60 |

| Grams of LA | 3.85 |
|---|---|
| % LA based on Fructose | 35.31 |
| % LA based on Total Reaction Weight | 2.04 |

It was observed that reduced char was present at filtration as compared to reactions at higher temperatures and lower acid levels and little to no char was accumulated on the reactor components.

Example 86

Into a three neck 250 mL round bottom flask 40.04 g deionized water and 7.21 g (0.04 mol, 0.37M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, an ice water bath was placed beneath the round bottom flask in order to cool the reaction mixture. The ice water bath was used to prevent the reaction mixture from getting too hot when the sulfuric acid was added. Once the reaction mixture was cold, 117.78 g (1.2 mol, 11.02M) sulfuric acid was added into the flask making sure to keep the reaction mixture below 30° C. Once all of the sulfuric acid was added to the reaction mixture the ice water bath was removed and a heating mantle was situated under the flask. The heat was turned on and set to a temperature of 50° C. The reaction was held at 50° C. for forty five minutes and then the reaction was shut down, the heating mantle was removed and cooled with the ice water bath. In order to form more product, levulinic acid and formic acid, the reaction mixture was heated back up to 50° C. and left to react for another thirty minutes. After the thirty minutes the reaction was shut down and cooled with an ice water bath. The reaction mixture was filtered but no solids were observed.

| | |
|---|---|
| Grams of LA | 2.43 |
| % LA based on Fructose | 33.65 |
| % LA based on Total Reaction Weight | 1.47 |

It was observed that reduced char was present at filtration as compared to reactions at higher temperatures and lower acid levels and little to no char was accumulated on the reactor components.

Example 87

Into a three neck 250 mL round bottom flask 40.07 g deionized water and 7.35 g (0.04 mol, 0.37M) D-fructose were charged. The round bottom flask was equipped with a magnetic stir bar, thermocouple, condenser, and glass stopper. The stir plate was set to stir at a rate of 550 RPM and the fructose quickly dissolved. Once the fructose was dissolved, an ice water bath was placed beneath the round bottom flask in order to cool the reaction mixture. The ice water bath was used to prevent the reaction mixture from getting too hot when the sulfuric acid was added. Once the reaction mixture was cold, 117.76 g (1.2 mol, 11.00M) sulfuric acid was added into the flask making sure to keep the reaction mixture below 30° C. Once all of the sulfuric acid was added to the reaction mixture the ice water bath was removed and a heating mantle was situated under the flask. The heat was turned on and set to a temperature of 50° C. The reaction was held at 50° C. for two hours and then the reaction was shut down, the heating mantle was removed and cooled with the ice water bath. The reaction mixture was filtered and the solids were placed into a vacuum oven to dry.

Once the solids were dried, they were removed from the vacuum oven and weighed.

| | |
|---|---|
| Grams of Solids | 3.00 |
| % Solids based on Fructose | 40.82 |
| % Solids based on Total Reaction Weight | 1.82 |

| | |
|---|---|
| Grams of LA | 2.55 |
| % LA based on Fructose | 34.64 |
| % LA based on Total Reaction Weight | 1.54 |

It was observed that reduced char was present at filtration as compared to reactions at higher temperatures and lower acid levels and little to no char was accumulated on the reactor components.

Examples 80-87 demonstrate that running the reactions at reduced temperatures (less than 100° C.) improves the selectivity for levulinic acid, and increased levels of mineral acid (such as 40-72% of sulfuric acid) lead to faster reaction times. Combining these 2 features results in faster reactions that are highly selective to levulinic acid with significantly less char.

Reactor Modeling

A combination of experimental and modeling research has been conducted in order to analyze and recommend continuous reactor designs for the production of levulinic acid from fructose. The main focus of this example is a description of kinetic and reactor modeling methods, model validation, and recommended reactor configurations that maximize the yield of the desired product while minimizing undesirable byproducts, such as HMF and char.

A validated kinetic model has been developed by adapting an acid-catalyzed glucose decomposition mechanism from the thesis of Girsuta to describe batch reactor data for the conversion of fructose to levulinic acid. Kinetic parameters in the model were adjusted using regression analysis to fit the model to the data. The model has been implemented for two types of ideal continuous reactors: a continuous stirred tank reactor (CSTR) and a plug flow reactor (PFR). The CSTR model predictions compared favorably with a single data set from a continuous flow reactor experiment. The experimental and modeling results illustrate that byproduct formation is minimized using higher catalyst ($H_2SO_4$) concentrations (e.g. 5 mole/liter) and lower temperatures (50 to 100° C.) than employed in the thesis.

The validated model was implemented in an Aspen Plus flowsheet to study the effect of multiple reactor configurations, residence times and reactor temperatures on the yields of the desired product (levulinic acid) and the undesired byproduct (humins, or char). More than fifty configurations were run and the resulting yield and conversion predictions were analyzed to recommend a reactor configuration for experimental study. The cases studied all used a feed with catalyst ($H_2SO_4$) concentration of 5 mole/liter and fructose concentration of 1 mole/liter.

Examples 88-102

Model Predictions for Multiple Reactor Configurations

The reaction rate mechanism that was implemented and verified in Aspen for fructose decomposition was used to study the performance of networks of CSTR and PFR reactors. Several networks were studied at the same time to simplify comparison of performance. The Aspen flowsheet diagram is shown in FIG. 3. Five configurations were studied, as described in the figure.

Case A: Two CSTR reactors in series: large, then small
Case B: A small PFR followed by a large CSTR
Case C: A single CSTR
Case D: A large CSTR followed by a small PFR
Case E: Three CSTR reactors in series The flowsheet simulation was run many times using an acid concentration of 5 mole/liter and a sugar concentration of 1 mole/liter. The total residence time was constrained to be 180 minutes for all cases, to provide a consistent basis for comparison. The temperature range described in this report ranged from 100 to 120° C. Other simulations were done at temperatures ranging from 90 to 100° C., but they had lower conversion and are not described in this report. The individual residence times for the reactors and the reactor temperatures were varied for the study.

The results from three interesting sets of cases are shown in Table 7. Examples 88-102 are described in Table 7. In set 1, all temperatures were set to 100° C., and the reactor residence times were at their base value. In set 2, temperatures were also 100° C., but the residence time for the first reactor in each sequence was increased. This modification reduced the yield to the undesirable humin product. In set 3, the temperature for the second (or third) reactor was increased. In case 3D, the CSTR residence time was also increased. This modification increased the yield of desirable levulinic acid but did not significantly change the yield to the undesirable humins product. Cases 3D and 3E have very similar performance predictions.

Configurations 3D and 3E both had a large CSTR reactor followed by one or two small reactors at higher temperature. In case 3D, the second reactor is a PFR, while in case 3E, the second and third reactors are small CSTRs. These configurations both had fructose conversion greater than 99%, soluble Levulinic Acid yield above 63%, Humins yield of 1.23%, and HMF yield below 0.1%. Total yield of Levulinic Acid (soluble & insoluble) was predicted to be greater than 94% for these configurations.

Examples with continuous feed aspects or simple batch processes

HLPC Method

The instrument used was a WATERS 2695 LC system with a WATERS 2998 PDA detector. A Hamilton PRP-X300 column (7 μm 250×4.1 mm) was used with 5 μL injections. The column temperature was maintained at 50° C. There are two mobile phases used. "Solvent A" is 20 mM of Phosphoric Acid in DI $H_2O$. "Solvent B" is Methanol (HPLC Grade). An isocratic flow of 2 mL/min is used with a (80% Solvent A/20% Solvent B) mobile phase mixture. Sample data is analyzed by extracting a chromatogram at 210 nm wavelength.

LC-RI method The instrument used was a WATERS 1515 LC pump with a WATERS 717 autosampler and WATERS 2410 RI detector. A Supelcosil-LC-NH2 (250 mm×4.6 mm×5 μm) was used with 10 μL injections. The column temperature was maintained at 50° C. The mobile phase was 75% Acetonitrile/25% Nanopure $H_2O$. An isocratic flow of 1 mL/min was used. Samples were filtered and diluted 5-10× with Nanopure $H_2O$ before analysis.

Example 103

122.01 g deionized water and 108.03 g (96-98%) sulfuric acid was charged into a 500 mL 4-neck round bottom flask. 40.08 g HFCS 55 (high fructose corn syrup; ADM, Inc. 55% Fructose) was charged into a 60 mL syringe. The round bottom flask was situated in a heating mantle and equipped with a magnetic stir bar, thermocouple, condenser, glass

TABLE 7

Results summary for Sets 1-3 (Examples 88-102).

| Description | Ex. 88 Case 1A | Ex. 89 Case 1B | Ex. 90 Case 1C | Ex. 91 Case 1D | Ex. 92 Case 1E | Ex. 93 Case 2A | Ex. 94 Case 2B | Ex. 95 Case 2C |
|---|---|---|---|---|---|---|---|---|
| Yield LA Soluble | 60.07 | 61.47 | 55.08 | 62.70 | 61.56 | 59.19 | 60.33 | 55.08 |
| Fructose conversion | 95.88 | 99.30 | 89.49 | 98.95 | 98.07 | 94.75 | 97.81 | 89.49 |
| Yield Humins | 1.23 | 1.84 | 1.05 | 1.31 | 1.40 | 1.14 | 1.75 | 1.05 |
| Ration LA/humins | 49.00 | 33.43 | 52.42 | 47.73 | 43.94 | 52.00 | 34.45 | 52.42 |
| Yield Lev. A Total | 89.67 | 91.77 | 82.22 | 93.52 | 91.86 | 88.35 | 90.02 | 82.22 |
| Yield of HMF | 1.40 | 0.18 | 3.15 | 0.26 | 0.61 | 1.84 | 0.88 | 3.15 |
| Res. Time CSTR 1 | 120 | | 180 | 120 | 60 | 150 | | 180 |
| Res. Time CSTR 2 | 60 | 120 | | | 60 | 30 | 150 | |
| Res. Time CSTR 3 | | | | | 60 | | | |
| Res. Time PFR | | 61.84 | | 61.89 | | | 31 | |
| Total Res. Time (min) | 180 | 182 | 180 | 182 | 180 | 180 | 181 | 180 |
| Temp CSTR 1 | 100 | | 100 | 100 | 100 | 100 | | 100 |
| Temp CSTR 2 | 100 | 100 | | | 100 | 100 | 100 | |
| Temp CSTR 3 | | | | | 100 | | | |
| Temp PFR | | 100 | | 100 | | | 100 | |

| Description | Ex. 96 Case 2D | Ex. 97 Case 2E | Ex. 98 Case 3A | Ex. 99 Case 3B | Ex. 100 Case 3C | Ex. 101 Case 3D | Ex. 102 Case 3E |
|---|---|---|---|---|---|---|---|
| Yield LA Soluble | 61.03 | 61.21 | 62.96 | 62.26 | 55.08 | 63.57 | 63.49 |
| Fructose conversion | 96.94 | 97.20 | 99.04 | 99.74 | 89.49 | 99.82 | 99.74 |
| Yield Humins | 1.23 | 1..23 | 1.14 | 1.66 | 1.05 | 1.23 | 1.23 |
| Ration LA/humins | 49.79 | 49.93 | 55.31 | 37.42 | 52.42 | 51.86 | 51.79 |
| Yield Lev. A Total | 91.07 | 91.33 | 93.96 | 92.91 | 82.22 | 94.83 | 94.75 |
| Yield of HMF | 1.05 | 0.96 | 0.44 | 0.09 | 3.15 | 0.09 | 0.09 |
| Res. Time CSTR 1 | 150 | 120 | 150 | | 180 | 170 | 120 |
| Res. Time CSTR 2 | | 30 | 30 | 150 | | | 30 |
| Res. Time CSTR 3 | | 30 | | | | | 30 |
| Res. Time PFR | 31 | | | 30 | | 10 | |
| Total Res. Time (min) | 181 | 180 | 180 | 180 | 180 | 180 | 180 |
| Temp CSTR 1 | 100 | 100 | 100 | | 100 | 100 | 100 |
| Temp CSTR 2 | | 100 | 120 | 120 | | | 110 |
| Temp CSTR 3 | | 100 | | | | | 120 |
| Temp PFR | 100 | | | 100 | | 120 | | stopper and the syringe pump inlet tube. The water and sulfuric acid solution was stirred at 650 RPM and heated up to a temperature of 90° C. The HFCS 55 was added using a syringe pump over a course of two hours at a rate of 15 mL/hr. After all of the HFCS 55 had been added into the round bottom flask, the reaction was held at temperature for one hour. After a total reaction time of three hours a sample was taken to be analyzed by LC-UV and LC-RI and then the reaction was shut down and allowed to cool to ambient temperature. Once the reaction mixture was cool, the solids were filtered out and then washed with water and acetone. The solids were then measured using a moisture analyzer.

| % FA | % LA | % HMF | % Fructose | % Glucose | g FA | g LA | g HMF | g Fructose | g Glucose | g Char |
|------|------|-------|------------|-----------|------|------|-------|------------|-----------|--------|
| 1.45 | 3.19 | 0.01  | 0.00       | 2.79      | 3.55 | 7.80 | 0.02  | 0.00       | 6.82      | 2.49   |

Example 104

30 g Fructose, 37.02 g Glucose was dissolved into 33.09 g deionized water. Then 40.02 g of the sugar solution was placed into a 60 mL syringe. 122.02 g deionized water and 108.11 g sulfuric acid (96-98%) was charged into a 500 mL 4-neck round bottom flask. The round bottom flask was situated in a heating mantle and equipped with a magnetic stir bar, thermocouple, condenser, glass stopper and the syringe pump tube inlet. The water and sulfuric acid solution was stirred at 650 RPM and heated up to a temperature of 90° C. The sugar solution was added using a syringe pump over a course of two hours at a rate of 15 mL/hr. After all of the sugar solution had been added into the round bottom flask, the reaction was held at temperature for one hour. After a total reaction time of three hours a sample was taken and analyzed by LC-UV and LC-RI and then the reaction was shut down and allowed to cool to ambient temperature. Once the reaction mixture was cool, the solids were filtered out and then washed with water and acetone. The solids were then measured using a moisture analyzer.

| % FA | % LA | % HMF | % Fructose | % Glucose | g FA | g LA | g HMF | g Fructose | g Glucose | g Char |
|------|------|-------|------------|-----------|------|------|-------|------------|-----------|--------|
| 1.17 | 2.82 | 0.00  | 0.00       | 4.77      | 2.88 | 6.93 | 0.00  | 0.00       | 11.73     | 1.211  |

Examples 105, 106 and 107

15 mL of the resulting solution from Example 103 was added to an empty 3 oz, high pressure, high temperature reaction vessel equipped with a thermocouple and pressure gauge for monitoring the internal temperature and pressure (Example 105). A second reaction vessel was also charged with 15 mL of the resulting solution from Example 103 (Example 106). After proper assembly, the reaction vessels were then placed into a 140° C. hot oil bath to reach an internal temperature of around 130° C. After 2 hours the reaction vessels were removed from the hot oil and placed in a room temperature water bath for 1 minute to begin cooling. Following the room temperature water bath, the reactors were placed in an ice water bath to quench the reactions. Once the reactions had cooled completely, the reactor vessels were opened and the mixtures were analyzed individually by HPLC. Any solids formed during the reaction were also washed with DI water and weighed. The solids water wash was also analyzed by HPLC and included in the final product calculations.

The HPLC results for Example 105 show the glucose completely converted to products. The levulinic acid to solids mass ratio was 1.5. (Weight of LA to weight to solids.) For Example 106 the HPLC results show the glucose reacting to about 88% conversion. The levulinic acid to solids mass ratio was 1.5.

A third 3 oz, high pressure, high temperature reaction vessel equipped with a thermocouple and pressure gauge for monitoring the internal temperature and pressure was charged with 15 mL of the resulting solution from Example 104 (Example 107). After proper assembly, the reaction vessel was placed into a 120° C. hot oil bath to reach an internal temperature of around 110° C. After 3 hours the reaction vessel was removed from the hot oil and placed in a room temperature water bath for 1 minute to begin cooling. Following the room temperature water bath, the reactor was placed in an ice water bath to quench the reaction. Once the reaction had cooled completely, the reactor vessel was opened and the mixture was analyzed by HPLC. Any solids formed during the reaction were also washed with DI water and weighed. The solids water wash was also analyzed by HPLC and included in the final product calculations.

The HPLC results for Example 107 show the glucose conversion to be 87%. The levulinic acid to solids mass ratio was 1.9.

Example 108

47.95 g deionized water and 99.68 g sulfuric acid (96-98%) were charged into a 250 mL 3-neck round bottom flask. 2.40 g Fructose and 10.02 g deionized water was charged into a small beaker and placed on a stir plate to dissolve the fructose. The round bottom flask was situated in a heating mantle and equipped with a magnetic stir bar, thermocouple, condenser and glass stopper. The water and sulfuric acid was stirred at a rate of 650 RPM and heated up to a temperature of 90° C. The fructose solution was injected all at once into the reaction mixture and allowed to react for one hour. After a reaction time of one hour a sample was pulled to be analyzed by LC-UV and LC-RI then the reaction was shut down. Once the reaction mixture was at ambient temperature it was filtered and no solids were observed.

| % FA | % LA | % HMF | % Fructose | g FA | gLA | g HMF | g Fructose | g Char |
|---|---|---|---|---|---|---|---|---|
| 0.29 | 0.64 | 0.00 | 0.00 | 0.41 | 0.91 | 0.00 | 0.00 | 0.00 |

Example 109

84.04 g deionized water and 63.79 g sulfuric acid (96-98%) was charged into a 250 mL 3-neck round bottom flask. 1.7108 g HMF and 10.02 g deionized water was charged into a scintillation vial and placed on a stir plate to dissolve the HMF. The round bottom flask was situated in a heating mantle and equipped with a magnetic stir bar, thermocouple, condenser and glass stopper. The water and sulfuric acid mixture was stirred at 650 RPM and heated up to a temperature of 90° C. The HMF solution was then injected all at once into the round bottom flask and allowed to react for one hour. The reaction was shut down after a reaction time of one hour and a sample was taken at the end and analyzed by FC-UV. Once the reaction mixture was at ambient temperature it was filtered and no solids were observed.

| % FA | % LA | % HMF | g FA | g LA | g HMF | g Char |
|---|---|---|---|---|---|---|
| 0.44 | 0.97 | 0.00 | 0.70 | 1.55 | 0.00 | 0.00 |

Example 110

1.6658 g HMF and 10.0437 g deionized water was charged into a scintillation vial and set on a stir plate to dissolve the HMF. 77.06 g deionized water and 76.55 g sulfuric acid (96-98%) was charged into a 250 mL 3-neck round bottom flask. The round bottom flask was situated in a heating mantle and equipped with a magnetic stir bar, thermocouple, condenser, and glass stopper. The water and sulfuric acid was heated up to 90° C. while stirring at 650 RPM. Once the HMF was all dissolved it was injected all at once into the water and sulfuric acid mixture. The reaction was shut down after a reaction time of 30 minutes and a sample was taken at the end and analyzed by FC-UV. Once the reaction mixture was at ambient temperature it was filtered and no solids were observed.

| % FA | % LA | % HMF | g FA | g LA | g HMF | g Char |
|---|---|---|---|---|---|---|
| 0.40 | 0.99 | 0.00 | 0.58 | 1.45 | 0.00 | 0.00 |

Example 111

3.785 g Fructose, 2.657 g HMF and 10.014 g deionized water was charged into a beaker then placed on a stir plate to dissolve the fructose and HMF. 139.35 g deionized water and 103.03 g sulfuric acid (96-98%) was charged into a 500 mL 4-neck round bottom flask. The round bottom flask was situated in heating mantle and equipped with a magnetic stir bar, thermocouple, condenser, and two glass stoppers. The water and sulfuric acid were stirred at 650 RPM and heated to 90° C. The fructose and HMF solution was then injected into the round bottom flask all at once and allowed to react for one hour. After a reaction time of one hour a sample was taken to be analyzed by LC-UV and LC-RI and then shut down. Once the reaction mixture was at ambient temperature it was filtered and no solids were observed.

| % FA | % LA | % HMF | % Fructose | g FA | gLA | g HMF | g Fructose | g Char |
|---|---|---|---|---|---|---|---|---|
| 0.45 | 1.11 | 0.23 | 0.279 | 1.05 | 2.59 | 0.54 | 0.65 | 0.00 |

Example 112

13.24 g HMF and 30.05 g deionized water was charged into a beaker then placed the beaker on a stir plate to dissolve the HMF. 113.35 g deionized water and 103.05 g (96-98%) sulfuric acid was charged into a 500 mL 4-neck round bottom flask. The round bottom flask was situated in a heating mantle and equipped with a magnetic stir bar, thermocouple, condenser, glass stopper and the syringe pump inlet. The water and sulfuric acid was stirred at 650 RPM and heated to a temperature of 90° C. The HMF solution was added using a syringe pump over a course of five hours at a rate of 7.4 mL/hr. After all of the HMF had been added into the round bottom flask, the reaction was held at temperature for one hour. After a total reaction time of six hours a sample was taken and analyzed by LC-UV and then the reaction was shut down and allowed to cool to ambient temperature. Once the reaction mixture was cool, the solids were filtered out and then washed with water and methylene chloride and then the char was left to dry overnight. The char was then put into a scintillation vial which was then placed in a vacuum oven to dry until a constant weight was obtained.

| % FA | % LA | % HMF | g FA | 8 LA | g HMF | g Char |
|---|---|---|---|---|---|---|
| 2.21 | 4.71 | 0.00 | 5.39 | 11.48 | 0.00 | 0.745 |

Example 113

A 250 mF Erlenmeyer flask was charged with 114.95 g of 64% Sulfuric Acid, and 64.27 g de-ionized water. The acidic water mixture was placed in an ice bath and allowed to cool. After the solution was cool, 3.78 g Fructose and 2.65 g Hydroxymethylfurfural (HMF) were also added to the Erlenmeyer flask. The mixture was mixed well until completely dissolved. The resulting molarities calculate to 0.14M Fructose, 0.14M HMF and 5M Sulfuric acid.

15 mL of the prepared solution was added to an empty 3 oz, high pressure, high temperature reaction vessel equipped with a thermocouple and pressure gauge for monitoring the internal temperature and pressure. After proper assembly, the reaction vessel was then placed into a 100° C. hot oil bath to reach an internal temperature of around 90° C. After 60 min the reaction vessel was removed from the hot oil and placed in a room temperature water bath for 1 minute to begin cooling. Following the room temperature water bath, the reactor was placed in an ice water bath to quench the reaction. Once the reaction had cooled completely, the reactor vessel was opened and the mixture was analyzed by HPFC. Any solids formed during the reaction were washed with DI water and weighed. The solids water wash was also analyzed by HPFC and included in the final product calculations.

The HPFC results for Example 113 show the HMF conversion equal to 99% conversion and the fructose completely reacting away after 60 min. The molar percent yield of levulinic acid (LA) was 86.9%. Also the LA to solids mass ratio was 2.67.

Example 114

A 250 mL Erlenmeyer flask was charged with 114.94 g of 64% Sulfuric Acid, and 63.14 g de-ionized water. The acidic water mixture was placed in an ice bath and allowed to cool. After the solution was cool, 3.79 g Fructose and 3.98 g Hydroxymethylfurfural (HMF) were also added to the Erlenmeyer flask. The mixture was mixed well until completely dissolved. The resulting molarities calculate to 0.14M Fructose, 0.21M HMF and 5M Sulfuric acid.

15 mL of the prepared solution was added to an empty 3 oz, high pressure, high temperature reaction vessel equipped with a thermocouple and pressure gauge for monitoring the internal temperature and pressure. After proper assembly, the reaction vessel was then placed into a 100° C. hot oil bath to reach an internal temperature of around 90° C. After 60 min, the reaction vessel was removed from the hot oil and placed in a room temperature water bath for 1 minute to begin cooling. Following the room temperature water bath, the reactor was placed in an ice water bath to quench the reaction. Once the reaction had cooled completely, the reactor vessel was opened and the mixtures were analyzed individually by HPFC. Any solids formed during the reaction were also washed with DI water and weighed. The solids water wash was also analyzed by HPFC and included in the final product calculations.

The HPLC results for Example 114 show the HMF reacting to 99% conversion and the fructose completely reacting away after 60 min. The molar percent yield of levulinic acid (LA) was 87.8%. Also the LA to solids mass ratio was 3.58.

Examples with continuous feed and/or recycling aspects:

Example 115: Synthesis of LA+FA with a Mixed Sugar Solution by Continuous Feeding To a 3 neck, 1 L round bottom flask equipped with condenser and thermocouple magnetic stirring was charged 126.45 g $H_2O$ and 311.88 g of 64% (wt) $H_2SO_4$. The reaction mixture was heated to 90° C. at which point 40.5 g of a sugar solution containing 69.3% fructose, 23% water, 6.16% glucose, and 1.54% others was injected over a 5 hour period using a syringe pump. When all of the sugar solution had been added, the reaction mixture was cooled to room temperature and transferred to a 1 L Hastelloy C Parr reactor kettle. The reactor was sealed and heated to 120° C. for 90 minutes to fully convert any remaining reactant or intermediates to products. During this final step, the pressure of the reactor remained below 25 psi.

TABLE 8

HPLC analytical results of hydrolysis samples taken at various times during the reaction

| Time of reaction (min) | Temperature (° C.) | % Formic Acid | % Levulinic Acid | % HMF |
|---|---|---|---|---|
| 305 | 89.4 | 1.539 | 3.222 | 0.072 |
| 90 | 120 | 1.526 | 3.391 | Non-Detectable |

The above reaction mixture was cooled to room temperature using an ice bath. 435 gm of this mixture was poured into a 150 ml Buchner funnel with a glass frit (4-5 micron filter size), that was placed on top of 1000 mL filter flask connected to a Teflon vacuum pump. Vacuum was used to aid the filtration (<250 mm), filtrate was allowed to drain for 5-10 minutes before the Teflon vacuum pump was turned off. 413 gm of filtrate and 22.11 gm of wet solids were obtained (9 for composition details for the filtrate). The solid was washed with 4×50 mL DI water. Another 10 mL was added and the filtrate of the 10 mL wash was tested using a pH probe (pH=2.04). The solids were washed with 48 gm of acetone and air dried overnight to give 5.0 gm of dry char (1.04 wt % based on total initial charge). The char was powdery in nature, and was not sticky. It flowed easily before filtration, and it did not stick to reactor components.

The 413 gm filtrate was poured into a 1000 mL cell culture spinner flask, followed by addition of 828 gm of methyl isobutyl ketone (99.8%, Macron chemicals. Philipsburg, N.J.). The solution was stirred at 150 rpm for 30 minutes and the two layers were poured into a 2000 mL cylindrical separatory funnel. The two layers were allowed to phase separate over 30 mins. The bottom layer was drained into a 1000 mL three neck round bottom flask and the top layer (OEX) to a 2000 mL two neck round bottom flask (see Table 9 for composition details for each layer).

The 2000 mL two neck round bottom flask containing the organic extract (OEX) was setup for short path distillation using a magnetic stirrer and heating mantle connected to a variable transformer. The short path distillation head was connected to a Teflon vacuum pump and a chiller (set at 10° C.). Temperature of the organic extract and the distillate vapor was measured using a J-type thermocouple. The vacuum was controlled to 50 mm using a digivac vacuum controller. The 2000 mL flask was subjected to 50 mm vacuum before the heating mantle was turned. Once the temperature in the round bottom flask reached 37° C. the methyl isobutyl ketone started distilling over (distillate vapor temperature ~37° C.). Distillation was stopped when 80% of the methyl isobutyl ketone was distilled. The levulinic acid in the bottom of the reactor vessel was isolated as a crude solution in methyl isobutyl ketone (See Table 9 for details).

The 1000 mL three neck round bottom flask containing the bottom layer of the extraction (raffinate) mixture was also setup for distillation. Setup for distillation included a distillation adapter, condenser connected to a chiller, J-type thermocouple for the round bottom flask and distillate vapor, Teflon vacuum pump and an oil bath with a hotplate/stirrer for heating. The pressure was controlled using a J-Kem scientific vacuum controller. The round bottom flask containing the raffinate was subjected to 50 mm vacuum before it was heated. Once the temperature in the round bottom flask reached 40° C. the water methyl iso butyl ketone azeotrope started distilling over. Distillation was continued till all the methyl isobutyl ketone was distilled over (distillation receiver shows only increase in water layer, top layer remains constant). The raffinate, after distillation, was used to make the next batch. (See Table 9 for composition details).

TABLE 9

Composition for filtration, extraction and distillation streams

| Sample stream | Mass | % Levulinic acid | % Formic acid | % Sulfuric acid |
|---|---|---|---|---|
| Filtrate | 413 | 3.39 | 1.53 | Not determined |
| Raffinate, before distillation | 401 | 1.31 | 0.38 | 39.65 |
| Raffinate, after distillation | 355.3 | 1.57 | 0.33 | 44.23 |
| Organic extract | 827 | 0.84 | 0.43 | 0.12 |
| Final crude product | 142.8 | 3.58 | 0.69 | 0.85 |

Example 116: Synthesis of LA and FA with Recycled Raffinate from Example 1

To a 3 neck flask equipped with magnetic stirring, a chilled condenser, and thermocouple was charged 348 g of the recycled raffinate from Example 115. This raffinate contained approximately 157 g $H_2SO_4$. 5.6 g levulinic acid, and 1.2 g formic acid. To the raffinate charge was added 67 g of fresh water to bring the acid concentration in the aqueous phase to approximately 40%. The aqueous phase was heated to 90° C. before the addition of 40.35 g of a sugar solution of identical composition to that used in Example 115 was added over 5 hours. After the sugar addition was complete, a 120° C. post cook identical to that of Example 115 was used to fully convert any unreacted reagents.

TABLE 10

HPLC analytical results of composition.

| Time (min) | Temperature (° C.) | % Formic Acid | % Levulinic Acid | % HMF |
|---|---|---|---|---|
| 305 | 90 | 1.876 | 4.362 | 0.073 |
| 90 | 120 | 1.958 | 4.386 | Non-Detectable |

The above reaction mixture was cooled to room temperature using an ice bath. 398.8 gm of this mixture was poured into a 150 ml Buchner funnel with a glass frit (4-5 micron filter size), that was placed on top of 1000 mL filter flask connected to a Teflon vacuum pump. The solids flowed easily out of the reactor and were not sticky in nature. Vacuum was used to aid the filtration (<250 mm), filtrate was allowed to drain for 5-10 minutes before the Teflon vacuum pump was turned off. 379.2 gm of filtrate and 19.6 gm of wet solids were obtained. The solid was washed with 10×100 mL DI water. Another 80 mL was added and the filtrate of the 80 mL wash was tested using a pH probe (pH=1.96). The solids were washed with 68 gm of acetone and air dried overnight to give 5.43 gm of dry char (1.21 wt % based on total initial charge)

The extraction and purification procedure was repeated as described in Example 115 to afford a second recycled raffinate stream. Recycled Raffinate Stream from Example 116.

Example 117: Synthesis of LA and LA with Recycled Raffinate Stream from Example 116

To a 3 neck flask equipped with magnetic stirring, a chilled condenser, and thermocouple was charged 250 g of the recycled raffinate from Example 116. This raffinate contained approximately 126 g $H_2SO_4$, 4.2 g levulinic acid, and 1.9 g formic acid. To the raffinate charge were added 82 g of 64% fresh $H_2SO_4$ and 106 g of fresh water to bring the acid concentration in the aqueous phase to approximately 40%. The aqueous phase was heated to 90° C. before the addition of 40.85 g of a sugar solution of identical composition to that used in Example 115 was added over 5 hours. After the sugar addition was complete, a 120° C. post cook identical to that of Example 115 was used to fully convert any unreacted reagents. Again, analyses of the hydrolysis mixture at various times are presented in Table 11.

TABLE 11

HPLC analytical results of composition.

| Time (min) | Temperature (° C.) | % Formic Acid | % Levulinic Acid | % HML |
|---|---|---|---|---|
| 300 | 89.8 | 1.778 | 4.092 | 0.079 |
| 90 | 120 | 1.716 | 4.080 | Non-Detectable |

The above reaction mixture was cooled to room temperature using an ice bath. 447 gm of this mixture was poured into a 150 ml Buchner funnel with a glass frit (4-5 micron filter size), that was placed on top of 1000 mL filter flask connected to a Teflon vacuum pump. The solid char was not sticky and did not adhere to reactor components. It flowed easily in the liquid mixture. Vacuum was used to aid the filtration (<250 mm), filtrate was allowed to drain for 5-10 minutes before the Teflon vacuum pump was turned off. 426.1 gm of filtrate and 20.95 gm of wet solids were obtained. The solid was washed with 9×100 mL DI water. Another 80 mL was added and the filtrate of the 80 mL wash was tested using a pH probe (pH=2.33). The solids were washed with 68 gm of acetone and air dried overnight to give 5.0 gm of dry char (1.04 wt % based on total initial charge)

The extraction and purification procedure was repeated as described in Example 115 to afford a third recycled raffinate stream. Recycled Raffinate Stream from Example 117.

Example 118: Synthesis of LA and FA with Recycled Raffinate Stream from Example 117

To a 3 neck flask equipped with magnetic stirring, a chilled condenser, and thermocouple was charged 371 g of the recycled raffinate from Example 117. This raffinate contained approximately 177.5 g $H_2SO_4$, 7.1 g levulinic acid, and 2.9 g formic acid. To the raffinate were added 27 g of fresh water and 40.42 g of 64% $H_2SO_4$ to bring the acid concentration in the aqueous phase to approximately 40%. The aqueous phase was heated to 90° C. before the addition of 42.7 g of a sugar solution of identical composition to that used in Example 115 was added over 5 hours. After the sugar addition was complete, a 120° C. post cook identical to that of Example 1 was used to fully convert any unreacted reagents. Again, analyses of the hydrolysis mixture at various times are presented in Table 12.

TABLE 12

HPLC analytical results of composition.

| Time (min) | Temperature (° C.) | % Formic Acid | % Levulinic Acid | % HML |
|---|---|---|---|---|
| 305 | 90.1 | 2.174 | 4.626 | 0.085 |
| 90 | 120 | 2.124 | 4.380 | Non-Detectable |

The above reaction mixture was cooled to room temperature using an ice bath. 431 gm of this mixture was poured into a 150 ml Buchner funnel with a glass frit (4-5 micron filter size), that was placed on top of 1000 mL filter flask connected to a Teflon vacuum pump. The solid char was not sticky and did not adhere to reactor components. It flowed readily in the liquid mixture. Vacuum was used to aid the filtration (<250 mm), filtrate was allowed to drain for 5-10 minutes before the Teflon vacuum pump was turned off. 402.8 gm of filtrate and 28.3 gm of wet solids were obtained. The solid was washed with 9×100 mL DI water. Another 50 mL was added and the filtrate of the 80 mL wash was tested using a pH probe (pH=3.3). The solids were washed with 68 gm of acetone and air dried overnight to give 5.43 gm of dry char (1.13 wt % based on total initial charge)

Example 119: Synthesis of LA and LA from Sugar Solution with Higher Glucose Content To a 3 neck flask equipped with magnetic stirring, a chilled condenser, and thermocouple was charged 200.14 g of 64% $H_2SO_4$ and 122.53 g fresh water. The aqueous phase was heated to 90° C. before 41.60 g of a sugar solution containing 64.6% fructose, 24.0% water, 9.9% glucose, and 1.5% others was added over 5 hours. After the sugar addition was complete, the reaction was cooled to room temperature and filtered through a fine glass fritted glass filter to remove approximately 2 wt % insoluble humins that were not sticky in nature. The solids flowed quite easily in the reactor and did not stick to reactor components.

TABLE 13

HPLC analytical results of hydrolysis sample.

| Time (min) | Temperature (° C.) | % Formic Acid | % Levulinic Acid | % HMF |
|---|---|---|---|---|
| 300 | 90.2 | 2.431 | 4.290 | 0.187 |

After filtration, 341.57 g of hydrolysate was recovered and extracted with 677 g MIBK. The MIBK was added on top of the hydrolysate, allowed to mix for 30 minutes and settle for 30 minutes before separating the aqueous and organic layers. The residual MIBK in the aqueous layer was removed by vacuum distillation before the recycled raffinate was used in Example 120.

Example 120: Synthesis of LA+FA from Recycled Raffinate from Example 119

To a 3 neck flask equipped with magnetic stirring, a chilled condenser, and thermocouple was charged 295 g of the recycled raffinate from Example 119. This raffinate contained 124 g $H_2SO_4$, 2.7 g levulinic acid and 1.3 g formic acid, as well as a small amount of unreacted glucose. The raffinate was augmented with 21 g fresh water and 86 g of a 64% $H_2SO_4$ solution to bring the acid concentration of the aqueous mixture to approximately 40%. The aqueous charge was then heated to 90° C. before the addition of 63.8 g of a sugar solution with the same composition as the sugar solution in Example 115. The sugar solution was added via syringe pump over 5 hours, at which point the reaction was cooled to room temperature and filtered through a fine glass fritted glass filter to remove approximately 2 wt % insoluble humins. Again, analyses of the hydrolysis mixture at various times are presented in Table 14.

TABLE 14

HPLC analytical results of hydrolysis samples.

| Time (min) | Temperature (° C.) | % Formic Acid | % Levulinic Acid | % HMF |
|---|---|---|---|---|
| 300 | 90.0 | 3.325 | 5.764 | 0.138 |

Following cooling, the reaction mixture was re-heated to 90° C. and held for 60 minutes to more completely convert starting materials or stable intermediates to products.

TABLE 15

HPLC analytical results of hydrolysis samples during 90° C. post cook.

| Time (min) | Temperature (° C.) | % Formic Acid | % Fevulinic Acid | % HMF |
|---|---|---|---|---|
| Initial | 25 | 3.218 | 5.914 | 0.041 |
| 0 | 90 | 3.252 | 6.105 | 0.041 |
| 60 | 90 | 3.139 | 6.275 | Non-Detectable |

Example 121 for Large Scale Production

Figure 4:
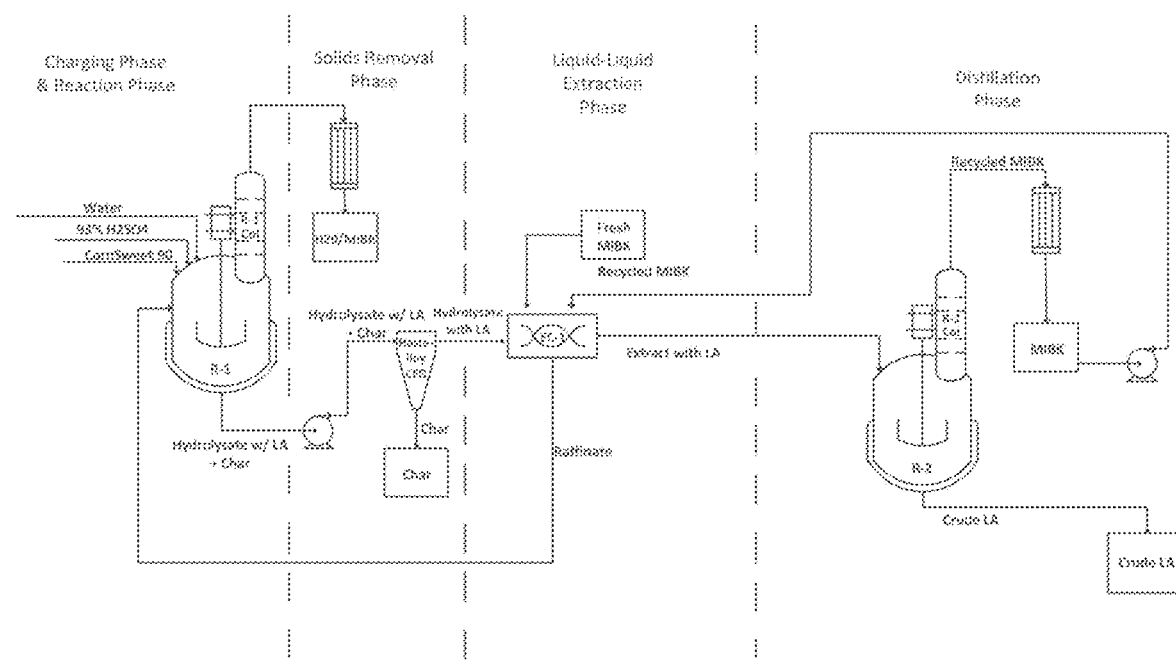
FIG. 4 depicts an industrial scale process to produce levulinic acid.

FIG. 4 provides a process flow diagram for an embodiment of Sugar to Fevulinic Acid conversion/scale up. The following provides an explanation of the scale up procedure.

The reaction was performed in a 2000 gallon glass lined reactor (R1) and the solids that were formed were to be removed in the Hastelloy centrifuge (CFG) using the 8000 gallon poly tank for temporary storage of the hydrolysate. The centrifuged hydrolysate was then sent to 600 gallon settling tank (EC-1) for extraction with methyl isobutyl ketone (MIBK). The organic extract (OEX) was sent to another 2000 gallon glass line reactor (R2) for concentration (distillation of excess MIBK) and the hydrolysate was sent back to the 2000 gallon reaction vessel (R1) for the next reaction. (See FIG. 4.)

To a 2000 gallon glass line reactor (R1) equipped with condenser and thermocouple was charged 5540 lb water and 5380 lb of 93.3% (wt) sulfuric acid. The reactor was vented to a portable caustic scrubber (pH=12.0) pulling at 685 Torr. The reaction mixture was heated to 90° C. using pressurized steam. The CS90 (23% water. 69.3% fructose, 6.2% glucose, 1.5% other sugars) was added at 310 lbs/hour using a diaphragm pump. After all the CS90 had been added, the reaction mixture was maintained a 90° C. for an additional 90 minutes The reactor was cooled to 40° C. before subjecting the hydrolysate to centrifugation.

The reaction mixture was cooled to 44° C. in 255 minutes at which point it was fed to the Hastelloy centrifuge (CFG). The hydrolysate was fed to the centrifuge at ~1600 lbs/hr and the centrifuge was spinning at 800 rpm. The liquid flowing through the centrifuge basket was fed to an 8000 gallon poly tank. Analysis of the first 2000 lbs of sample in poly tank showed 1.25% solids, which was not a significant reduction in solids. Celite (filter aid) slurried in water was fed to the centrifuge to coat the filter cloth followed by addition of hydrolysate from 2000 gallon reaction vessel (R1). ~8000 lbs of hydrosylate was centrifuged and fed to the poly tank. The % solids in the poly tank was around 0.8% and the 4000 lbs of hydrolysate in reaction vessel (R1) had 1.4% solids. The hydrolysate from the poly tank was transferred to reaction vessel (R1) and the composite had 1.1% solids. The hydrolysate was then filtered using a sock filter (100 micron) housed in a stainless steel canister. The filtered sample showed 0.74% solids. Filtration was continued using the same filter sock till the back pressure changed from 10-15 psig to around 40 psig. The filter sock were changed in the following sequence:

100 micron—2 different socks
25 micron—1 sock
10 micron—1 sock
1 micron—2 socks

The final percent solids after multiple sock filtrations were 0.8%. 50 lbs of Celite was added to the hydrolysate that was transferred back to GF5 and the hydrolysate was subjected to centrifugation. The centrifuged hydrolysate had 0.4% solids.

The 6000 gallon settling tank (EC-1) was first filled with 23000 lbs of MIBK followed by addition of hydrolysate from poly tank, the agitator was running at 117 rpm during the addition of hydrolysate. Agitator was turned off after 30 minutes and the top layer was sampled twice for analysis.

TABLE 16

Analysis of Organic extract from settling tank (EC-1)

| Time after agitator was off (minutes) | % Eevulinic Acid | % Formic Acid | % Sulfuric Acid | % Water |
|---|---|---|---|---|
| 15 | 0.94 | 0.45 | 0.5 | 1.19 |
| 30 | 0.95 | 0.45 | 0.68 | 1.28 |

The bottom layer (raffinate) was carefully transferred back to the reaction vessel (R1) using a diaphragm pump connected to a sock filter canister with a 100 micron filter sock. 10580 lbs of raffinate was transferred to the reaction vessel (R1).

12000 lbs organic extract (OEX) was transferred to another 2000 gallon glass line reactor (R2) for concentration of the final product. The MIBK in the OEX was distilled at 100 Torr maintaining the vent temperature below 70° C. More material was transferred once the level in reactor (R2) was concentrated to 2000 lbs. After 28.5 hrs 4500 lbs of final product was isolated with the following composition:

MIBK=92.3%, Levulinic acid=4.69%, Water=0.03%

The raffinate was also subjected to distillation to remove any MIBK. The distillation was performed at 100 Torr so as to maintain the vent temperature below 70° C. After 3730 lbs of water/MIBK mixture was distilled the raffinate was sampled for analysis.

Water=62.18%, Sulfuric acid=34.83%, Levulinic acid=1.58%, MIBK=0.58%, Solids=0.15%

Example 122: 1$^{st}$ Recycle Raffinate Batch with CS90

To the 2000 gallon reaction vessel (RI) containing 8800 lbs of raffinate (11 recycle) was charged 451 lb water and 1690 lb of 93.3% (wt) sulfuric acid. The reactor was vented to a portable caustic scrubber (pH=12.0) pulling at 685 Torr. The reaction mixture was heated to 90° C. using pressurized steam. The CS90 (23% water, 69.3% fructose, 6.2% glucose, 1.5% other sugars) was added at 310 lbs/hour using a diaphragm pump. After all the CS90 had been added, the reaction mixture was maintained a 90° C. for an additional 90 minutes. The reactor was cooled to 40° C. before subjecting the hydrolysate to centrifugation.

The reaction mixture was cooled to 45° C. in 165 minutes at which point it was fed to the Hastelloy centrifuge. The hydrolysate was fed to the centrifuge at ~2000 lbs/hr and the centrifuge was spinning at 800 rpm. The liquid flowing through the centrifuge basket was fed to a 8000 gallon poly tank. Analysis of the sample in poly tank showed 0.8% solids.

6000 gallon settling tank (EC-1) was first filled with 23000 lbs of recycle MIBK followed by addition of 12500 lbs hydrolysate from poly tank, the agitator was running at 117 rpm during the addition of hydrolysate. Agitator was turned off after 30 minutes and the top layer was sampled four times for analysis.

TABLE 17

Analysis of Organic extract from EC-1

| Time after agitator was off (minutes) | % Levulinic Acid | % Formic Acid | % Sulfuric Acid | % Water |
|---|---|---|---|---|
| 15 | 1.36 | 0.74 | 0.13 | 1.1 |
| 50 | 1.35 | 0.74 | 0.15 | 1.08 |
| 65 | 1.37 | 0.74 | 0.15 | 1.06 |
| 80 | 1.45 | 0.75 | 0.16 | 1.07 |

The bottom layer (raffinate) was carefully transferred back to the reaction vessel (R1) using a diaphragm pump. 15000 lbs of raffinate was transferred to the reactor (R1). Analysis of reactor contents (R1) showed high level of MIBK, so the raffinate was sent back to DC-1 for settling. 60 minutes later 12560 lbs raffinate was transferred to the 2000 gallon reaction vessel (R1) for distillation of MIBK.

12000 lbs organic extract (OEX) was transferred to another 2000 gallon glass lined reactor (R2) for concentration of the final product. The MIBK in the OEX was distilled at 100 Torr maintaining the vent temperature below 70° C. More material was transferred once the level in reactor (R2) was concentrated to 2000 lbs. During couple of the transfers raffinate layer was observed in the OEX that was drained in to a 250 gallon poly tote. (Total of 1000 lbs of raffinate drained in to the tote) After 24 hrs 2000 lbs of crude product was isolated with the following composition:

MIBK=86.55%, Levulinic acid=9.17%, Sulfuric acid=6.47%, Formic acid=1.46%, Solids=0.13%

The raffinate was also subjected to distillation to remove any MIBK. The distillation was performed at 100 Torr so as to maintain the vent temperature below 70° C. After 6645 lbs of water/MIBK mixture was distilled the raffinate was sampled for analysis.

Water=54.88%, Sulfuric acid=42.96%, Levulinic acid=3.55%, MIBK=0.06%, Solids=0.14%

Example 123: 2$^{nd}$ Recycle Raffinate Batch with CS90

To the 2000 gallon reaction vessel (R1) containing 6000 lbs of raffinate (2$^{nd}$ recycle) was charged 2090 lb water and 2430 lb of 93.3% (wt) sulfuric acid. The reactor was vented to a portable caustic scrubber (pH=12.0) pulling at 685 Torr. The reaction mixture was heated to 90° C. using pressurized steam. The CS90 (23% water, 69.3% fructose, 6.2% glucose, 1.5% other sugars) was added at 310 lbs/hour using a diaphragm pump. After all the CS90 had been added, the reaction mixture was maintained a 90° C. for an additional 90 minutes The reactor was cooled to 40° C. before subjecting the hydrolysate to centrifugation.

The hydrolysate was fed to the centrifuge at ~2000 lbs/hr and the centrifuge was spinning at 800 rpm. The liquid flowing through the centrifuge basket was fed to an 8000 gallon poly tank. Analysis of the sample in poly tank showed 1.01% solids.

The 6000 gallon settling tank (EC-1) was first filled with 21905 lbs of recycle MIBK followed by addition of 10700 lbs hydrolysate from poly tank, the agitator was running at 117 rpm during the addition of hydrolysate. Agitator was turned off after 30 minutes and the top layer was sampled four times for analysis.

TABLE 18

Analysis of Organic extract from EC-1

| Time after agitator was off (minutes) | % Levulinic Acid | % Formic Acid | % Sulfuric Acid | % Water |
|---|---|---|---|---|
| 30 | 1.35 | 0.94 | 1.77 | 1.47 |
| 60 | 1.4 | 0.99 | 1.78 | Not determined |
| 90 | 1.42 | 1.0 | Not determined | Not determined |
| 120 | 1.41 | 0.96 | Not determined | Not determined |

The bottom layer (raffinate) was carefully transferred back to the reaction vessel (R1) using a diaphragm pump. 15750 lbs of raffinate was transferred to the reactor (R1).

12000 lbs organic extract (OEX) was transferred to another 2000 gallon glass line reactor (R2) for concentration of the final product. The MIBK in the OEX was distilled at 100 Torr maintaining the vent temperature below 70° C. More material was transferred once the level in reactor was concentrated to 2000 lbs. During transfers raffinate layer was observed in the OEX that was drained in to a 250 gallon poly tote. (Total of 4000 lbs of raffinate drained in to the tote) After 30 hrs 2100 lbs of crude product was isolated with the following composition:

MIBK=83.1%, Levulinic acid=7.04%, Formic acid=2.12%

The raffinate was also subjected to distillation to remove any MIBK. The distillation was performed at 100 Torr so as to maintain the vent temperature below 70° C.

Example 124

Into a 500 mL four neck round bottom flask was charged 102.57 g deionized water and 103.04 g of 98% sulfuric acid. The round bottom flask was placed in a heating mantle and equipped with a magnetic stir bar, thermocouple, condenser, glass stopper and a rubber stopper that held the outlet tube of the syringe pump. In a beaker 38.03 g fructose and 25.60 g deionized water were charged. The solution was mixed until the fructose dissolved, and it was transferred into a plastic syringe situated on a syringe pump. The acid and water mixture in the 500 mL round-bottom flask was heated to 90° C. and then, the fructose and water mixture was added via the syringe pump. The fructose was added over a period of 1.25 hours so the rate on the syringe pump was set to 37.6 mL/hr. After a reaction time of 1.25 hours, all of the fructose had been added into the flask. The reaction was left to react for an additional hour in order to react all of the fructose. The reaction was then shut down and allowed to cool down. Samples were taken throughout the entire reaction and analyzed by HPLC. Once the reaction mixture was cool it was filtered through a fritted funnel and the solids were washed with deionized water and acetone. The solids that were in the funnel were placed in a jar and put into a vacuum oven to dry. The final yield numbers and composition data are listed below.

| Reaction Time (min) | Reaction Temp ° C. | Mol/L LA | Mol/L LA | Mol/L HML | Mol/L Fructose |
|---|---|---|---|---|---|
| 135 | 90.0 | 0.95 | 0.82 | 0.00 | 0.00 |

Once the solids were dried, they were removed from the vacuum oven and weighed.

| | |
|---|---|
| Grams of Char | 5.63 |
| LA to Char Ratio | 3.5 |
| LA Molar % Yield on reacted sugar and HML | 81.4 |
| LA Molar % Yield on reacted sugar and HML | 95.0 |

Into a 500 mL four neck round bottom flask was charged 102.09 g deionized water and 103.04 g of 98% sulfuric acid. The round bottom flask was placed on a heating mantle and equipped with a magnetic stir bar, thermocouple, condenser, glass stopper and a rubber stopper that held the outlet tube of the syringe pump. In a beaker was charged 37.89 g fructose and 26.07 g of deionized water. The solution was mixed until the fructose dissolved, and it was transferred into a plastic syringe situated on a syringe pump. The sulfuric acid and water mixture was heated to 90° C. and then the fructose and water mixture was added via the syringe pump. The fructose was to be added over a period of 1.25 hours so the rate on the syringe pump was set to 38.4 mL/hr. After a reaction time of 1.25 hours, all of the fructose had been added into the flask. The reaction was left to react for an additional hour in order to react all of the fructose. The reaction was then shut down and allowed to cool down. Samples were taken throughout the entire reaction and analyzed by HPLC. Once the reaction mixture was cool it was filtered through a fritted funnel and the solids were washed with deionized water and acetone. The solids that were in the funnel were placed in a jar and put into a vacuum oven to dry. The final yield numbers and composition data are listed below.

| Reaction Time (min) | Reaction Temp ° C. | Mol/L FA | Mol/L LA | Mol/L HMF | Mol/L Fructose |
|---|---|---|---|---|---|
| 135 | 90.2 | 0.94 | 0.82 | 0.04 | 0.00 |

Once the solids were dried, they were removed from the vacuum oven and weighed.

| | |
|---|---|
| Grams of Char | 5.9 |
| LA to Char Ratio | 3.3 |
| LA Molar % Yield on reacted sugar and HMF | 85.5 |
| FA Molar % Yield on reacted sugar and HMF | 97.5 |

Into a 500 mL four neck round bottom flask was charged 103.09 g deionized water and 103.03 g of 98% sulfuric acid. The round bottom flask was placed on a heating mantle and equipped with a magnetic stir bar, thermocouple, condenser, glass stopper and a rubber stopper that held the outlet tube of the syringe pump. In a separate beaker was charged 37.89 g fructose and 25.06 g deionized water. The solution was mixed until the fructose dissolved, and it was transferred into a plastic syringe situated on a syringe pump. The sulfuric acid and water mixture in the round bottom flask was heated to 90° C. and then the fructose and water mixture was added via the syringe pump. The fructose was added over a period of 2.5 hours so the rate on the syringe pump was set to 18.8 mL/hr. After a reaction time of 2.5 hours, all of the fructose had been added into the flask. The reaction was left to react for an additional hour in order to react all of the fructose. The reaction was then shut down and allowed to cool down. Samples were taken throughout the entire reaction and analyzed by HPLC. Once the reaction mixture was cool it was filtered through a fritted funnel and the solids were washed with deionized water and acetone. The solids that were in the funnel were placed in a jar and put into a vacuum oven to dry. The final yield numbers and composition data are listed below.

| Reaction Time (min) | Reaction Temp ° C. | Mol/L FA | Mol/L LA | Mol/L HMF | Mol/L Fructose |
|---|---|---|---|---|---|
| 210 | 90.3 | 1.00 | 0.89 | 0.04 | 0.00 |

Once the solids were dried, they were removed from the vacuum oven and weighed.

| | |
|---|---|
| Grams of Char | 5.6 |
| LA to Char Ratio | 3.8 |
| LA Molar % Yield on reacted sugar and HMF | 92.9 |
| FA Molar % Yield on reacted sugar and HMF | Near 100 |

Formic Acid Neutralization in MIBK

Example 125

A 5 wt % solution of formic acid (0.3 g) in methyl isobutyl ketone, MIBK (5.2 g) was made. An equal molar solution of sodium hydroxide (0.2 g) in water (1.9 g) was prepared. The two mixtures were combined in a vial and mixed well. Two layers formed in the vial and they were both tested by HPLC for % formic acid. The HPLC results show the MIBK solution dropped from 4.8% to 0.2% formic acid.

Example 126-127

Additional experiments were completed under the same procedure as example 125. Changes in the initial scale of the experiment along with a test using less water were also performed. The results are summarized in Table 19.

Example 128

A 5 wt % solution of formic acid (0.3 g) in MIBK (5.1 g) was made. Sodium hydroxide powder (0.4 g) was added to the solution which is equal to twice the moles of formic acid. The mixture was mixed well for 1 hour. After mixing, the MIBK was tested by HPLC for % formic acid. The HPLC results show the MIBK solution dropped from 4.7% to 0% formic acid.

Examples 129-130

Further experiments were carried out under the same procedure as example 128 along with changes in the base used. The results are summarized in Table 19.

TABLE 11

| EX. | FA (g) | MIBK (g) | Water (g) | NaOH (g) | CaCO$_3$ (g) | CaH$_2$O$_2$ (g) | Initial % FA in MIBK | % FA in MIBK (HPLC) | % FA in Water (HPLC) | g FA in MIBK | g FA in Water | Total g FA in solution |
|---|---|---|---|---|---|---|---|---|---|---|---|---|
| 125 | 0.27 | 5.20 | 1.88 | 0.23 | | | 4.85 | 0.22 | 6.51 | 0.011 | 0.123 | 0.134 |
| 128 | 0.25 | 5.08 | NA | 0.43 | | | 4.70 | 0.00 | NA | 0.000 | NA | 0.000 |
| 129 | 0.27 | 5.01 | NA | | 0.60 | | 5.14 | 4.84 | NA | 0.243 | NA | 0.243 |
| 130 | 0.27 | 5.08 | NA | | | 0.46 | 4.98 | 2.34 | NA | 0.119 | NA | 0.119 |
| 126 | 0.27 | 5.03 | 0.25 | 0.25 | | | 5.03 | 0.00 | NA | 0.000 | ND | 0.000 |
| 127 | 6.38 | 125.07 | 5.54 | 5.54 | | | 4.85 | 0.00 | 17.95 | 0.000 | 0.994 | 0.994 |

Table 19 shows that sodium hydroxide worked best at removing the formic acid from the MIBK compared to calcium carbonate and calcium hydroxide. Calcium carbonate does not show much promise in reducing the formic acid in MIBK. However calcium hydroxide does reduce the formic acid with equal molar ratios and may remove more if the ratio is increased.

Example 131: Isoamyl Alcohol

Aqueous sulfuric acid stock solutions were prepared at various concentrations and mixed with isoamyl alcohol to yield the compositions (in weight %) below. Phase behavior (1 phase vs. phase separated) was determined visually. The data show that the solubility of the isoamyl organic solvent increases slightly as the amount of sulfuric acid in the mixture increases (#2 vs. #16). At the appropriate composition ratio, the solubility of sulfuric acid in isoamyl alcohol can be high (#15).

| | % sulfuric acid | % organic | % water | Visual Observations |
|---|---|---|---|---|
| 1 | 49.0% | 2.0% | 49.0% | 1 phase |
| 2 | 48.5% | 2.9% | 48.5% | 1 phase |
| 3 | 48.2% | 3.6% | 48.2% | 2 phases |
| 4 | 50.0% | 0.0% | 50.0% | 1 phase |
| 5 | 15.0% | 69.9% | 15.0% | 1 phase |
| 6 | 15.4% | 69.2% | 15.4% | 2 phases |
| 7 | 20.0% | 0.0% | 80.0% | 1 phase |
| 8 | 19.6% | 2.0% | 78.4% | 2 phases |
| 9 | 1.6% | 92.1% | 6.3% | 1 phase |

| | % sulfuric acid | % organic | % water | Visual Observations |
|---|---|---|---|---|
| 10 | 1.8% | 90.8% | 7.4% | 2 phases |
| 11 | 10.0% | 0.0% | 90.0% | 1 phase |
| 12 | 9.8% | 2.1% | 88.1% | 2 phases |
| 13 | 0.7% | 92.8% | 6.5% | 1 phase |
| 14 | 0.9% | 91.3% | 7.9% | 2 phases |
| 15 | 0.0% | 0.0% | 100.0% | 1 phase |
| 16 | 0.0% | 2.2% | 97.8% | 2 phases |
| 17 | 0.0% | 92.1% | 7.9% | 1 phase |
| 18 | 0.0% | 90.7% | 9.3% | 2 phases |

Example 132: m-cresol

Aqueous sulfuric acid stock solutions were prepared at various concentrations and mixed with m-cresol to yield the compositions (in weight %) below. Phase behavior (1 phase vs. phase separated) was determined visually. The data show that the solubility of the m-cresol organic solvent in the in sulfuric aqueous phase is low (#2, #6), even at high sulfuric acid concentration (#13). The compatibility of sulfuric acid with the m-cresol organic solvent is low (#8, #12, #15)

| | % sulfuric acid | % organic | % water | Visual Observations |
|---|---|---|---|---|
| 1 | 0.0% | 1.3% | 98.7% | 1 phase |
| 2 | 0.0% | 1.9% | 98.1% | 2 phases |
| 3 | 0.0% | 87.7% | 12.3% | 1 phase |
| 4 | 0.0% | 86.0% | 14.0% | 2 phases |
| 5 | 9.9% | 0.8% | 89.3% | 1 phase |
| 6 | 9.9% | 1.4% | 88.8% | 2 phases |
| 7 | 0.2% | 98.2% | 1.6% | 1 phase |
| 8 | 0.3% | 97.5% | 2.3% | 2 phases |
| 9 | 19.9% | 0.6% | 79.5% | 1 phase |
| 10 | 19.8% | 0.8% | 79.4% | 2 phases |
| 11 | 0.2% | 99.2% | 0.6% | 1 phase |
| 12 | 0.3% | 98.5% | 1.2% | 2 phases |
| 13 | 49.8% | 0.5% | 49.8% | 2 phases |
| 14 | 0.5% | 99.1% | 0.5% | 1 phase |
| 15 | 0.9% | 98.3% | 0.9% | 2 phases |

Example 133: 2-ethyl Hexanol

Aqueous sulfuric acid stock solutions were prepared at various concentrations and mixed with to yield the compositions (in weight %) below. Phase behavior (1 phase vs. phase separated) was determined visually. The data show that the solubility of the 2-ethyl hexanol organic solvent in the in sulfuric aqueous 2-ethyl hexanol phase is low (#1), even at high sulfuric acid concentration (#6). The compatibility of sulfuric acid with the 2-ethyl hexanol organic solvent is low when the organic solvent content is very high (#10, #12, #14). When both the organic solvent content and the sulfuric acid content are high, there is a region of compatibility (#15).

| | % SA | % organic | % water | Visual Observations |
|---|---|---|---|---|
| 1 | 0.0% | 0.4% | 99.6% | 2-phase |
| 2 | 10.0% | 0.4% | 89.6% | 2-phase |
| 3 | 19.9% | 0.4% | 79.7% | 2-phase |
| 4 | 49.8% | 0.3% | 49.8% | 2-phase |
| 5 | 79.4% | 0.8% | 19.8% | 1 phase |
| 6 | 78.4% | 2.0% | 19.6% | 2-phase |
| 7 | 0.0% | 99.2% | 0.8% | 1 phase |
| 8 | 0.0% | 97.3% | 2.7% | 2-phase |
| 9 | 0.1% | 99.2% | 0.7% | 1 phase |
| 10 | 0.2% | 98.1% | 1.7% | 2-phase |
| 11 | 0.2% | 98.8% | 0.9% | 1 phase |
| 12 | 0.4% | 97.8% | 1.8% | 2-phase |
| 13 | 1.9% | 96.2% | 1.9% | 1 phase |
| 14 | 2.3% | 95.5% | 2.3% | 2-phase |
| 15 | 34.3% | 57.1% | 8.6% | 1 phase |
| 16 | 35.6% | 55.6% | 8.9% | 2-phase |

Examples 134-136: Backwash with Water to Remove Sulfuric Acid from Mixed Cresols To a vial were added 5 g of CSTR hydrolysate material that had been filtered through 1 μm glass fiber filter disc, spiked with LA (1.9% formic acid, 8 wt % levulinic acid, 50 wt. % sulfuric acid, and 40.1 wt. % water) and 5 g of mixed cresols from Aldrich. The vial was capped and the mixture was shaken mechanically for 0.5 minutes. The layers were separated by centrifugation for 5 minutes and each layer was isolated for weight determination. The sulfuric acid in the organic layer was determined by potentiometric auto-titration with potassium hydroxide/methanol as titrant.

The organic layer from the hydrolysate partition experiment was then washed with the amount of DI water given in the table below. The layers were then separated by centrifugation for 5 minutes and each layer was isolated for weight determination. The sulfuric acid in the organic layer was determined by potentiometric auto-titration with potassium hydroxide/methanol as titrant. These experiments show a water wash can reduce the amount of sulfuric acid in the organic extraction phase.

| Example | Wt. % sulfuric acid in organic after initial partition experiment | Mass of DI water wash (% by weight relative to the mass of organic phase) | Wt % sulfuric acid in organic layer after backwash with DI water |
|---|---|---|---|
| 134 | 0.64 | 10 | 0.08 |
| 135 | 0.73 | 50 | 0.01 |
| 136 | 0.70 | 100 | 0.01 |

Aldrich MSDS indicates an 80% mixture of cresol isomers and 20% phenol.

GC/MS indicates the mixture to be 80% cresol isomers and 20% 2,4-dimethylphenol.

Example 137: Neutralization to Remove Sulfuric Acid from Mixed Cresols

To a vial were added 5 g of CSTR hydrolysate material that had been filtered through 1 μm glass fiber filter disc, spiked with LA (1.9% formic acid, 8 wt % levulinic acid, 50 wt. % sulfuric acid, and 40.1 wt. % water) and 5 g of a m-cresol/p-cresol blend (60/40 blend ratio by weight). The vial was capped and the mixture was shaken mechanically for 0.5 minutes. The layers were separated by centrifugation for 5 minutes and each layer was isolated for weight determination. The sulfuric acid in the organic layer was determined by potentiometric auto-titration with potassium hydroxide/methanol as titrant to be 0.7% by weight.

The organic layer from the hydrolysate partition experiment was then washed with a saturated aqueous solution of 20% (by weight) of sodium bicarbonate. The layers were separated by centrifugation for 5 minutes and each layer was isolated for weight determination. The sulfuric acid in the organic layer was determined by potentiometric auto-titration with potassium hydroxide/methanol as titrant to be non-detectable.

Acros Organics 99% m-cresol and Alfa Aesar 99% p-cresol were used in the above example.

Examples 138 and 139: Backwash with Water to Remove Sulfuric Acid from Isoamyl Alcohol To a vial were added 5 g of CSTR hydrolysate material that had been filtered through 1 um glass fiber filter disc, spiked with LA (1.9% formic acid, 8 wt % levulinic acid, 50 wt. % sulfuric acid, and 40.1 wt. % water) and 5 g of isoamyl alcohol from Aldrich. The vial was capped and the mixture was shaken mechanically for 0.5 minutes. The layers were separated by centrifugation for 5 minutes and each layer was isolated for weight determination. The sulfuric acid in the organic layer was determined by potentiometric auto-titration with potassium hydroxide/methanol as titrant.

The organic layer from the hydrolysate partition experiment was then washed with the amount of DI water given in the table below. The layers were then separated by centrifugation for 5 minutes and each layer was isolated for weight determination. The sulfuric acid in the organic layer was determined by potentiometric auto-titration with potassium hydroxide/methanol as titrant. The resulting organic layer was then washed again with 100 weight % water, further lowering the sulfuric acid content. These experiments show a water wash can reduce the amount of sulfuric acid in the organic extraction phase.

| Example | Wt. % sulfuric acid in organic after initial partition experiment | Mass of DI water wash (% by weight relative to the mass of organic phase) | Wt % sulfuric acid in organic layer after backwash with DI water |
|---|---|---|---|
| 138 | 19.0 | 50 | 3.72 |
| 139 | 3.72 | 100 | 0.94 |

Example 140: Distillation of Formic Acid from a Mixture of Formic Acid, Levulinic Acid, Sulfuric Acid, Water, and Unknown Impurities To a 3 neck round bottom flask equipped with a magnetic stir bar was charged 255.60 g of a solution containing 11.12 g levulinic acid, 5.44 g formic acid, 99.43 g sulfuric acid, 139.61 g $H_2O$, and trace amounts of several unknown impurities The flask was equipped with a thermocouple and a short path distillation apparatus with a condenser chilled to 1° C. with recirculating coolant. The distillation system was evacuated down to 40 Torr and before the kettle was heated to 45° C. The distillate was exhibited a head temperature between 31-33° C. Distillate was allowed to come overhead until the head temperature dropped below 28° C., at which point the distillation kettle was cooled to 25° C. the pressure increased to atmospheric pressure, and samples were taken from the kettle as well as distillation recovery flask. After sampling, the kettle was re-evacuated to 40 Torr and heated this time to 55° C. The procedure of distilling till the head temp falls, sampling, and redistilling at an elevated temperature was repeated until no more formic acid could be observed in the distillation kettle.

TABLE 20

Analysis of distillate and kettle samples taken during the distillation described in Example 140.

| Cut | Kettle Temp | Sample | Mass (g) | % LA | % FA | % $H_2SO_4$ | g LA | g FA | g $H_2SO_4$ | % FA of Charge | % LA of Charge |
|---|---|---|---|---|---|---|---|---|---|---|---|
| 1 | 65° C. | Distillate | 87.42 | — | 4.46 | — | — | 3.90 | — | 77.8 | 0.00 |
|   |        | Kettle | 168.18 | 6.00 | 0.48 | 55.0 | 10.09 | 0.81 | 92.50 | 16.16 | 89.73 |
| 2 | 75° C. | Distillate | 96.40 | 0.10 | 4.58 | — | 0.10 | 4.41 | — | 88.16 | 0.87 |
|   |        | Kettle | 159.20 | 6.49 | 0.28 | 59.3 | 10.33 | 0.45 | 91.73 | 8.97 | 91.86 |
| 3 | 80° C. | Distillate | 100.46 | 0.10 | 4.55 | — | 0.103 | 4.57 | — | 91.19 | 0.91 |
|   |        | Kettle | 155.14 | 6.68 | 0.23 | 59.7 | 10.36 | 0.36 | 89.83 | 7.19 | 92.16 |
| 4 | 85° C. | Distillate | 102.72 | 0.10 | 4.50 | — | 0.10 | 4.62 | — | 92.21 | 0.92 |
|   |        | Kettle | 152.88 | 6.59 | 0.25 | 60.6 | 10.07 | 0.39 | 89.78 | 7.69 | 89.60 |
| 5 | 90° C. | Distillate | 108.84 | 0.11 | 4.45 | — | 0.12 | 4.85 | — | 96.82 | 1.04 |
|   |        | Kettle | 146.76 | 6.96 | 0.00 | 63.5 | 9.87 | 0.00 | 90.04 | 0.00 | 87.77 |

Example 141: Vacuum Distillation of Formic Acid from a Mixture of Formic Acid, Levulinic Acid, Sulfuric Acid, Water, and Unknown Impurities with Continuous Addition of $H_2O$ To a 500 mL 4 neck round bottom flask equipped with a magnetic stir bar was charged 249.27 g of a solution containing 10.87 g levulinic acid, 5.31 g formic acid, 97.13 g sulfuric acid, 136.38 g $H_2O$, and trace amounts of several unknown impurities. The flask was equipped with a thermocouple, an addition funnel charged with 124.28 g DI $H_2O$, and a short path distillation apparatus with a condenser cooled to 1° C. with recirculating coolant. The pressure of the system was reduced to 40 Torr before a heating mantle set to 45° C. was activated. When the solution in the flask reached approximately 42° C., distillate was observed. The head temperature fluctuated around 31-32° C. during distillation. When the distillate began to drip into the collection flask, $H_2O$ from the addition funnel was added dropwise at roughly the same rate as the distillate was being removed. When all the $H_2O$ from the addition funnel had been added, the pressure of the system was raised to atmospheric pressure and the system was cooled. Samples of the reaction flask mixture and distillate were taken, and the addition funnel was charged with more $H_2O$. The process of distilling with dropwise addition of $H_2O$ was continued until formic acid was no longer detected in the distillation flask.

TABLE 21

Analyses of distillate and kettle samples throughout distillation described in Example 141.

| Cut | Mass H$_2$O Added (g) | Sample | Mass (g) | % LA | % FA | % H$_2$SO$_4$ | g LA | g FA | g H$_2$SO$_4$ | % FA of Charge | % LA of Charge |
|---|---|---|---|---|---|---|---|---|---|---|---|
| 1 | 124.28 | Distillate | 93.88 | 0.06 | 2.53 | — | 0.06 | 2.38 | — | 44.72 | 0.51 |
|   |   | Kettle | 276.48 | 3.80 | 0.95 | 54.1 | 10.51 | 2.63 | 149.58 | 49.43 | 96.69 |
| 2 | 48.62 | Distillate | 45.76 | 0.03 | 1.15 | — | 0.01 | 0.53 | — | 54.62 | 0.11 |
|   |   | Kettle | 269.46 | 3.72 | 0.67 | 49.1 | 10.41 | 1.81 | 132.30 | 34.08 | 95.74 |
| 3 | 51.14 | Distillate | 46.63 | 0.02 | 0.79 | — | 0.01 | 0.37 | — | 61.54 | 0.06 |
|   |   | Kettle | 263.48 | 3.66 | 0.52 | 31.3 | 10.37 | 1.38 | 82.47 | 25.93 | 95.34 |
| 4 | 47.25 | Distillate | 40.43 | 0.01 | 0.55 | — | 0.00 | 0.22 | — | 65.71 | 0.04 |
|   |   | Kettle | 279.62 | 3.74 | 0.44 | 42.9 | 11.48 | 1.22 | 119.96 | 22.89 | 105.57 |
| 5 | 47.86 | Distillate | 50.02 | 0.01 | 0.46 | — | 0.00 | 0.23 | — | 70.00 | 0.04 |
|   |   | Kettle | 244.88 | 3.72 | 0.34 | 44.0 | 10.34 | 0.84 | 107.75 | 15.85 | 95.08 |
| 6 | 48.63 | Distillate | 32.22 | 0.01 | 0.40 | — | 0.00 | 0.13 | — | 72.41 | 0.02 |
|   |   | Kettle | 246.85 | 3.47 | 0.25 | 45.9 | 10.13 | 0.61 | 112.40 | 11.43 | 93.19 |
| 7 | 101.4 | Distillate | 103.28 | 0.00 | 0.27 | — | 0.00 | 0.28 | — | 77.66 | 0.04 |
|   |   | Kettle | 236.03 | 3.55 | 0.15 | 40.7 | 10.19 | 0.35 | 99.67 | 6.57 | 93.70 |
| 8 | 96.82 | Distillate | 88.51 | 0.01 | 0.16 | — | 0.01 | 0.14 | — | 80.24 | 0.05 |
|   |   | Kettle | 239.65 | 3.38 | 0.09 | 43.1 | 10.08 | 0.22 | 105.54 | 4.06 | 92.68 |
| 9 | 97.74 | Distillate | 98.88 | 0.00 | 0.09 | — | 0.00 | 0.09 | — | 81.92 | 0.01 |
|   |   | Kettle | 229.68 | 3.51 | 0.00 | 44.8 | 10.23 | 0.00 | 109.71 | 0.00 | 94.10 |

Levulinic Acid Partition Coefficients

Examples 142-174

To a vial were added 5 g of CSTR hydrolysate material that had been filtered through 1 um glass fiber filter disc, spiked with LA (1.9% formic acid, 8 wt % levulinic acid, 50 wt. % sulfuric acid, and 40.1 wt. % water) and 5 g of organic solvent. The vial was capped and the mixture was shaken mechanically for 0.5 minutes. The layers were separated by centrifugation for 5 minutes and each layer was isolated for weight determination. The sulfuric acid in the organic layer was determined by potentiometric auto-titration with potassium hydroxide/methanol as titrant.

The partition coefficient of levulinic acid in this system was calculated according to:

$$\text{Partition Coefficient} = \frac{m_{LA,s}/m_s}{m_{LA,a}/m_a}$$

where $m_{LA,s}$ is the mass of levulinic acid in the organic solvent phase, ms is the total mass of the organic solvent phase, $m_{LA,a}$ is the mass of the levulinic acid in the aqueous phase, and $m_a$ is the total mass of the aqueous phase. The aqueous phase is pipette out of the mixture is weight. Ms is then calculated by difference, $m_{LA,a}$ is measured by HPLC and $m_{LA,s}$ is calculated by difference. The partition coefficient of formic acid was calculated in a similar fashion.

| | Organic Solvent | LA Partition Coefficient | Formic Acid Partition Coefficient | % Sulfuric acid in organic phase | NOTES |
|---|---|---|---|---|---|
| 142 | Methyl isoamyl ketone | 0.38 | 0.63 | 0.447 | |
| 143 | Methyl isobutyl ketone | 0.67 | 0.82 | NR | |
| 144 | Diisobutyl ketone | 0.1 | 0.15 | NR | |
| 145 | Acetophenone | 0.65 | 1.03 | 4.2 | |
| 146 | Cyclohexanone | 2.26 | 3.05 | 3.01 | Required an additional 2.44 g of water to induce layer separation |
| 147 | Isophorone | 1.91 | 1.95 | 16.9 | |
| 148 | Neopentyl alcohol | 2.01 | 9.61 | 21.2 | Required an additional 0.45 g of water to induce layer separation |
| 149 | Isoamyl alcohol | 2.33 | 6.91 | 19 | Required an additional 6 wt % water to induce layer separation |
| 150 | n-hexanol | 0.93 | 7.23 | 19.9 | |
| 151 | n-heptanol | 0.78 | 8.00 | 22.9 | |
| 152 | 2-ethyl hexanol | 0.5 | 12.3 | 12.8 | |
| 153 | n-octanol | 0.59 | 3.79 | NR | |
| 154 | 1-nonanol | 0.59 | 4.62 | NR | |

-continued

| | Organic Solvent | LA Partition Coefficient | Formic Acid Partition Coefficient | % Sulfuric acid in organic phase | NOTES |
|---|---|---|---|---|---|
| 155 | 1-undecanol | 0.55 | 7.94 | 16 | |
| 156 | Phenol | 3.94 | 0.57 | 1.02 | |
| 157 | 4-methoxyphenol | 1.77 | | 6.1 | |
| 158 | Guaiacol | 0.72 | 0.31 | 0.11 | |
| 159 | 2-sec butyl phenol | 1.88 | 0.25 | 0.042 | |
| 160 | Nonyl phenol | 0.26 | 0.14 | NR | |
| 161 | Methylene chloride | 0.23 | 0.14 | NR | |
| 162 | Methyl isobutyl carbinol | 1.04 | 2.73 | 20.7 | |
| 163 | Anisole | 0.19 | 3.20 | NR | |
| 164 | Ethylene glycol di-n-butyl ether | 0.2 | 0.71 | 0.22 | |
| 165 | Castor oil | 0.04 | 0.37 | 0.75 | |
| 166 | m-cresol | 1.14 | 4.27 | 0.51 | |
| 167 | p-cresol | 1.06 | 3.86 | 0.9 | |
| 168 | o-cresol | 0.9 | 3.98 | 0.28 | |
| 169 | Cresol mix from Aldrich* | 2.17 | 0.40 | 0.64 | |
| 170 | 60/40 m-cresol/p-cresol | 2.38 | 0.45 | 0.7 | |
| 171 | 75/25 m-cresol/p-cresol | 2.29 | 0.41 | 0.57 | |
| 172 | Diethyl carbonate | 0.26 | 0.62 | 0.04 | |
| 173 | Methyl salicylate | 0.08 | 0.13 | Below detection limit | |
| 174 | 2,4-dimethylphenol | 1.97 | 0.39 | 0.22 | |

NR = Not reported
*Aldrich MSDS indicates an 80% mixture of cresol isomers and 20% phenol. GC/MS indicates the mixture to be 80% cresol isomers and 20% 2,4-dimethylphenol.

Example 175: Formic Acid Separation from MIAK by Distillation

To a 1 L round bottom flask equipped with variac-controlled electric heating mantle, thermocouple, magnetic stir bar, pressure sensor, 1-inch×18-inch vacuum-jacketed glass column packed with wire gauze packing, and magnetic bucket-type reflux control head was added 76.0 g of formic acid and 76.0 g MIAK. The still was controlled at 200 torr for a duration of 100 minutes and a reflux ratio of 6:1 reflux:collect. Bottom flask temperature ranged from 77.1° C. to 101.5° C. while the overhead temperature ranged from 60.1° C. to 61.1° C. Three fractions were collected: Fraction 1, 13.8 g, 89.187% formic acid by HPLC, Fraction 2, 18.2 g, 88.842% formic acid by HPLC, Fraction 3, 26.4 g, 88.944% formic acid by HPLC, Residual bottoms, 76.7 g, 3.261% formic acid by HPLC.

Example 176: Formic Acid Separation from MIBK by Distillation

To a 1 L round bottom flask equipped with variac-controlled electric heating mantle, thermocouple, magnetic stir bar, pressure sensor, 1-inch×18-inch vacuum-jacketed glass column packed with wire gauze packing, and magnetic bucket-type reflux control head was added 63.47 g of formic acid and 641.55 g MIBK. The still was operated at 763 torr for a duration of 260 minutes and a reflux ratio of 6:1 reflux:collect. Bottom flask temperature ranged from 115.3° C. to 116.5° C. while the overhead temperature ranged from 97.1° C. to 114.7° C. Several fractions were collected:

| Fraction | Mass (g) | % FA by HPLC |
|---|---|---|
| 1 | 14.72 | 13.925 |
| 2 | 33.38 | 12.949 |
| 3 | 38.06 | 12.267 |
| 4 | 74.97 | 11.097 |
| 5 | 44.87 | 10.152 |
| 6 | 103.8 | 8.889 |
| 7 | 68.06 | 7.64 |
| 8 | 15.47 | 6.755 |
| Bottoms | 300.77 | 5.267 |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A process to prepare levulinic acid comprising the steps:
   a) heating an aqueous solution of a mineral acid to about 60° C. to about 110° C. in a reactor, wherein the reactor is a batch reactor, wherein the reactor is a batch reactor;
   b) continuously adding an aqueous mixture of sugars, selected from monosaccharides, polysaccharides, and mixtures thereof, to the heated aqueous acid of step a) in the batch reactor over a period of from about 0.1 to about 40 hours to form a reaction mixture including levulinic acid and solids, c) filtering the solids from the reaction mixture, optionally after cooling;
d) adding a water immiscible liquid to the filtered reaction mixture so that the reaction mixture forms first and second layers, wherein greater than 90% of the mineral acid is in the first layer and greater than 90% of the water immiscible liquid is in the second layer;
e) recovering levulinic acid and optionally formic acid from the second layer; and
f) recycling the first layer back to the reactor,
wherein the mineral acid percentage by weight is from about 20 to about 80 percent of the reaction mixture; and wherein the water immiscible liquid is selected from the group consisting of methyl isoamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, guaiacol, 2-sec butyl phenol, nonyl phenol, methylene chloride, methyl isobutyl carbinol, anisol, ethylene glycol di-n-butyl ether, castor oil, m-cresol, p-cresol, o-cresol, cresol mixtures, diethyl carbonate, methyl salicylate, 2,4-dimethyl phenol, and mixtures thereof.

2. The process of claim 1, wherein the mineral acid is sulfuric acid ($H_2SO_4$), hydrochloric acid (HCl), hydrobromic acid (HBr), hydroiodic acid (HI), or combinations thereof.

3. The process of claim 1, wherein the sugars are selected from high fructose corn syrup, a mixture of at least two different sugars, sucrose, an aqueous mixture comprising fructose, an aqueous mixture comprising fructose and glucose, an aqueous mixture comprising hydroxymethylfurfural, an aqueous solution of fructose and hydroxymethylfurfural, an aqueous mixture of glucose, an aqueous mixture of maltose, an aqueous mixture of inulin, an aqueous mixture of polysaccharides, or mixtures thereof.

4. The process of claim 1, wherein the aqueous mixture comprises fructose and the levulinic acid is produced in greater than about 65% molar yield.

5. The process of claim 1, wherein the aqueous mixture comprises glucose and the levulinic acid is produced in greater than about 45% molar yield.

6. The process of claim 1, wherein the mineral acid percentage by weight is from about 20 to about 50 percent of the reaction mixture.

7. The process of claim 1, wherein the reaction mixture is heated for an additional period of time from about 0.1 hour to about 20 hours at a temperature range of from about 25° C. to about 110° C.

8. The process of claim 1, further comprising heating the first layer from about 120° C. to about 180° C. for a period of time.

9. The process of claim 1, further comprising cooling the first layer to below 100° C.

10. The process of claim 1, wherein ratio of the mass of levulinic acid to the mass of dry solids is greater than 1:1.

11. The process of claim 1, wherein less than 5 weight percent of dry char is produced relative to the entire weight of the reaction mixture.

12. The process of claim 1, wherein the first layer is heated for a period of time sufficient to convert greater than 90% of any glucose into levulinic acid.

13. The process of claim 1, wherein the cresol mixtures are selected from 60/40 m-cresol/p-cresol and 75/25 m-cresol/p-cresol.

14. The process of claim 1, wherein the solids that are formed do not adhere to glass, Teflon or metal surfaces.

15. The process of claim 12, wherein the metal surface is a hastelloy metal surface, alloy 20 metal surface, alloy 2205 metal surface, AL6XN metal surface or zirconium metal surface.

16. The process of claim 1, wherein the steps a) and b) are collectively reaction steps, the step c) is a solids filtration step, treating the filtered reaction mixture with the water immiscible solvent to form a water immiscible layer and a raffinate is an extraction step for extracting levulinic acid into the water immiscible solvent and wherein recovering levulinic acid and optionally formic acid from the second layer comprises a distillation step, wherein the mixture comprising levulinic acid is subjected to the steps of reaction, solids filtration, extraction and distillation, wherein the quantity of water, mineral acid, sugars and addition times can be varied, such that the water, mineral acid, the water immiscible solvent and optionally levulinic acid is recycled.

17. An industrial process to prepare levulinic acid comprising the integrated steps of reaction, solids filtration, extraction, distillation, and recycling of claim 16.

* * * * *